US008697029B2

(12) United States Patent
Anker et al.

(10) Patent No.: US 8,697,029 B2
(45) Date of Patent: Apr. 15, 2014

(54) MODULATED PHYSICAL AND CHEMICAL SENSORS

(75) Inventors: Jeffrey Anker, Ann Arbor, MI (US); Caleb Behrend, Los Angeles, CA (US); Raoul Kopelman, Ann Arbor, MI (US); Brandon McNaughton, Ypsilanti, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1755 days.

(21) Appl. No.: 11/169,977

(22) Filed: Jun. 29, 2005

(65) Prior Publication Data

US 2006/0008924 A1 Jan. 12, 2006

Related U.S. Application Data

(63) Continuation-in-part of application No. 10/419,033, filed on Apr. 18, 2003, now abandoned.

(60) Provisional application No. 60/373,492, filed on Apr. 18, 2002.

(51) Int. Cl.
*A61K 51/00* (2006.01)
*A61M 36/14* (2006.01)

(52) U.S. Cl.
USPC .......................................... 424/1.11; 424/1.65

(58) Field of Classification Search
USPC .............................................. 424/1.65
See application file for complete search history.

(56) References Cited

U.S. PATENT DOCUMENTS

| 3,676,679 | A | | 7/1972 | Waters |
|---|---|---|---|---|
| 4,778,758 | A | | 10/1988 | Ericsson et al. |
| 5,171,534 | A | | 12/1992 | Smith et al. |
| 5,232,839 | A | | 8/1993 | Eden et al. |
| 5,252,493 | A | | 10/1993 | Fujiwara et al. |
| 5,293,210 | A | | 3/1994 | Berndt |
| 5,336,600 | A | | 8/1994 | Monget |
| 5,374,527 | A | | 12/1994 | Grossman |
| 5,434,056 | A | | 7/1995 | Monget et al. |
| 5,516,670 | A | | 5/1996 | Kuehnle et al. ............... 435/459 |
| 5,534,527 | A | | 7/1996 | Black et al. |
| 5,593,854 | A | | 1/1997 | Berndt |
| 5,716,798 | A | | 2/1998 | Monthony et al. |
| 5,770,388 | A | | 6/1998 | Vorpahl |
| 5,770,440 | A | | 6/1998 | Berndt |
| 5,814,474 | A | | 9/1998 | Berndt |
| 5,888,760 | A | | 3/1999 | Godsey et al. |
| 5,910,300 | A | | 6/1999 | Tournier et al. ............... 424/9.34 |
| 5,998,224 | A | | 12/1999 | Rohr et al. |
| 5,998,517 | A | | 12/1999 | Gentle, Jr. et al. |
| 6,002,817 | A | | 12/1999 | Kopelman et al. ............... 385/12 |
| 6,027,946 | A | * | 2/2000 | Weitschies et al. ............ 436/526 |
| 6,096,272 | A | | 8/2000 | Clark et al. |
| 6,107,102 | A | | 8/2000 | Ferrari .......................... 436/518 |
| 6,143,558 | A | * | 11/2000 | Kopelman et al. ............ 435/325 |
| 6,159,686 | A | | 12/2000 | Kardos et al. ..................... 435/6 |
| 6,275,031 | B1 | | 8/2001 | Simmonds |
| 6,372,485 | B1 | | 4/2002 | Clark et al. |
| 6,395,506 | B1 | | 5/2002 | Pitner et al. |
| 6,437,563 | B1 | | 8/2002 | Simmonds et al. |
| 6,518,747 | B2 | | 2/2003 | Sager et al. |
| 6,586,259 | B1 | | 7/2003 | Mahan et al. |
| 6,596,532 | B1 | | 7/2003 | Hyman et al. |
| 6,597,176 | B2 | | 7/2003 | Simmonds et al. |
| 6,632,655 | B1 | | 10/2003 | Mehta et al. |
| 6,660,381 | B2 | * | 12/2003 | Halas et al. ..................... 428/403 |
| 6,777,226 | B2 | | 8/2004 | Jeffrey et al. |
| 6,780,581 | B2 | | 8/2004 | Vesey et al. |
| 6,825,655 | B2 | | 11/2004 | Minchole et al. |
| 6,900,030 | B2 | | 5/2005 | Pitner et al. |
| 6,927,570 | B2 | | 8/2005 | Simmonds et al. |
| 7,115,384 | B2 | | 10/2006 | Clark et al. |
| 7,183,073 | B2 | | 2/2007 | Hyman et al. |
| 7,323,139 | B2 | | 1/2008 | LaBorde et al. |
| 7,341,841 | B2 | | 3/2008 | Metzger et al. |
| 7,547,554 | B2 | | 6/2009 | Odefey |
| 7,564,245 | B2 | | 7/2009 | Lee |
| 7,575,934 | B2 | | 8/2009 | Atwood |
| 7,691,600 | B2 | | 4/2010 | Mercader Badia et al. |
| 2002/0150914 | A1 | | 10/2002 | Andersen et al. |
| 2003/0012693 | A1 | | 1/2003 | Otillar et al. |
| 2003/0076087 | A1 | | 4/2003 | Minchole et al. |

(Continued)

FOREIGN PATENT DOCUMENTS

WO     WO-00/67037 A2     11/2000
WO     WO-01/14591 A1     3/2001

(Continued)

OTHER PUBLICATIONS

Anker et al. (Applied Physics Letters 2003, 82, 1102-1104).*
Behrend et al. (Applied Physics Letters 2004, 84, 154-156).*
Metzger (Nature 1966, 212, 176-177).*
Horvath et al. (Czech. J. Phys. 1993, 43, 671-681).*
Kashevsky (J. Phys. D: Appl. Phys. 2001, 34, 518-524).*
Shine et al. (Rheol. Acta 1987, 26, 152-161).*
Melle et al. (Phys. Rev. E 2000, 61, 4111-4117).*
Taylor et al., "Real-time molecular and cellular analysis: the new frontier of drug discovery," Current Opinion in Biotechnology. Feb. 2001; 12(1):75 81)
Wagnieres et al., "In vivo fluorescence spectroscopy and imaging for oncological applications," Photochemistry and Photobiology. 1998; 68(5):603 632).

(Continued)

*Primary Examiner* — Michael G Hartley
*Assistant Examiner* — Melissa Perreira
(74) *Attorney, Agent, or Firm* — Marshall, Gerstein & Borun LLP

(57) ABSTRACT

The present invention relates to modulated (e.g., magnetically modulated) chemical sensors. In particular, the present invention relates to particles comprising fluorescent indicator dyes and methods of using such particles. Magnetic fields and/or Brownian motion modulate an optical property of the particle to distinguish it from background signals. The present invention thus provides improved methods of detecting a wide variety of analytes in fluids, fluid samples, cells and tissues.

15 Claims, 40 Drawing Sheets

(56) References Cited

U.S. PATENT DOCUMENTS

| | | |
|---|---|---|
| 2003/0124516 A1 | 7/2003 | Chung et al. |
| 2003/0169032 A1 | 9/2003 | Minchole et al. |
| 2004/0033627 A1 | 2/2004 | Aytur et al. |
| 2004/0058458 A1 | 3/2004 | Anker et al. |
| 2005/0048672 A1 | 3/2005 | Luxton et al. |
| 2006/0008924 A1 | 1/2006 | Anker et al. |
| 2006/0057578 A1 | 3/2006 | Willner et al. |
| 2006/0160171 A1 | 7/2006 | Bachur et al. |
| 2006/0210987 A1 | 9/2006 | Gleich |
| 2007/0020720 A1 | 1/2007 | Colin et al. |
| 2007/0037225 A1 | 2/2007 | Metzger et al. |
| 2007/0205767 A1 | 9/2007 | Xu et al. |
| 2008/0220411 A1 | 9/2008 | McNaughton et al. |
| 2009/0085557 A1 | 4/2009 | Krozer et al. |
| 2009/0136953 A1 | 5/2009 | Gold et al. |
| 2009/0269854 A1 | 10/2009 | Kageyama |
| 2010/0033158 A1 | 2/2010 | Dittmer et al. |
| 2010/0068755 A1 | 3/2010 | Walsh et al. |
| 2010/0072994 A1 | 3/2010 | Lee et al. |
| 2010/0129857 A1 | 5/2010 | Walsh et al. |

FOREIGN PATENT DOCUMENTS

| | | |
|---|---|---|
| WO | WO-03/019188 A1 | 3/2003 |
| WO | WO-2006/104700 A1 | 10/2006 |
| WO | WO-2007/120095 A1 | 10/2007 |
| WO | WO-2008/075285 A1 | 6/2008 |
| WO | WO-2009/037636 A1 | 3/2009 |
| WO | WO-2010/026551 A1 | 3/2010 |
| WO | WO-2010/041178 A1 | 4/2010 |
| WO | WO-2010/048511 A1 | 4/2010 |

OTHER PUBLICATIONS

Nie and Emery, "Probing Single Molecules and Single Nanoparticles by Surface-Enhanced Raman Scattering," Science. 1997; 275(5303): 1102 1106.
Kneipp et al., "Surface-Enhanced Raman Spectroscopy in Single Living Cells Using Gold Nanoparticles," Applied Spectroscopy. Feb. 2002; 56(2):150-154.
Mayer et al., "Measurement of the Fluorescence Lifetime in Scattering Media by Frequency-Domain Photon Migration," Applied Optics. 1999; 38: 4930-4938.
Valberg and Butler, "Magnetic particle motions within living cells. Physical theory and techniques," Biophysical Journal. Oct. 1897; 52(4):537 550.
Bornhop et al., "Advance in contrast agents, reporters, and detection," Journal of Biomedical Optics. 2001; 6(2):106 115.
Jain, "Understanding barriers to drug delivery: high resolution in vivo imaging is key," Clinical Cancer Research. 1999; 5(7): 1605 1606.
Moller et al., "Ultrafine particles cause cytoskeletal dysfunctions in macrophages," Toxicology and Applied Pharmacology. Aug. 2002; 182(3):197 207.
Jiang et al., "A lost-wax approach to monodisperse colloids and their crystals," Science. 291:453-457 (2001).
Richads Kortum and Sevickmuraca, "Quantitative Optical Spectroscopy for Tissue Diagnosis," Annual Review of Physical Chemistry, 47:555-606 (1996).
Crick, "The Physical Properties of Cytoplasm. A Study by Means of the Magnetic Particle Method. Part II. Theoretical Treatment," Strangeways Research Laboratory, Cambridge, 505-532 (1950).
Crick, et al., "The Physical Properties of Cytoplasm a Study by Means of the Magnetic Particle Method—Part I Experimental," Strangeways Research Laboratory, 37-80 (1949).
Agayan et al., "Optical Manipulation of Metal-Silica Hybrid Nanoparticles," *Proceedings of SPIE*, 5514:502-513 (2004).
Astalan et al., "Biomolecular Reactions Studied Using Changes in Brownian Rotation Dynamics of Magnetic Particles," *Biosensors and Bioelectronics*, 19:945-951 (2004).
Bao et al., "Cell and Molecular Mechanics of Biological Materials," *Nat. Mat.*, 2:715-725 (2003).

Behrend et al., "Microheology with Modulated Optical Nanoprobes (MOONs)," *J. Magnetism and Magnetic Mats.*, 293:663-670 (2005).
Bhiladvala et al., "Effect of Fluids on the $Q$ Factor and Resonance Frequency of Oscillating Micrometer and Nanometer Scale Beams," *Phys. Rev. E*, 69:36307-1-36307-5 (2004).
Biswal et al., "Micromixing with Linked Chains of Paramagnetic Particles," *Anal. Chem.*, 76:6448-6455 (2004).
Cebers, "Dynamics of an Active Magentic Particle in a Rotating Magentic Field," *Phys. Rev. E.*, 73:021505-1-021505-5 (2006).
Connolly et al., "Experimental Evaluation of the Magnetic Properties of Commerically Available Magnetic Microspheres," *Bio-Medical Materials and Engineering*, 15:421-431 (2005).
Ekinci et al., "Nanoelectromechnical Systems," *Review of Scientific Instruments*, 76:061101-1-061101-12 (2005).
Elfwing et al., "Observing Growth and Division of Large Numbers of Individual Bacteria by Image Analysis," *Applied and Environmental Microbiology*, 70(2):675-678 (2004).
Fennimore et al., "Rotational Actuators based on Carbon Nanotubes," *Nature*, 424:408-410 (2003).
Gitterman et al., "Order and Choas: Are They Contradictory or Complementary?" *Eur. J. Phys.*, 23:119-122 (2002).
Gu et al., "Using Biofunicational Magnetic Nanoparticles to Capture Gram-Negative Bacteria at an Ultra-Low Concentration," *Chemical Communications*, 15:1966-1967 (2003).
Hafeli et al., "Characterization of Magnetic Particles and Microspheres and Their Magnetophoretic Mobility Using a Digital Microscopy Method," *European Cells and Materials*, 3:24-27 (2002).
Haukanes et al., "Application of Magnetic Beads in Bioassays," *Bio-Technology*, 11:60-63 (1993).
Hulteen et al., "Nanosphere Lithography: A Materials General Fabrication Process for Periodic Particle Array Surfaces," *J. Vac. Sol. Technol. A.*, 13:1553-1558 (1995).
Ilic et al., "Virus Detection Using Nanoelectromechanical Devices," *Appl. Phys. Lett.*, 85:26042606 (2004).
Ilic et al., "Single Cell Detection with Micromechanical Oscillators," *J. Vacuum Sci. & Tech. B: Microelectronics and Nanometer Structures*, 19:2825-2828 (2001).
Ishiyama et al., "Swimming of Magnetic Micro-Machines under a Very Wide-Range of Reynolds Number Conditions," *IEEE Trans. Magn.*, 37(4):2868-2870 (2001).
Korneva et al., "Carbon Nanotubes Loaded with Magnetic Particles," *Nano Lett.*, 5:879-884 (2005).
Kurlyandskaya et al., "Magnetic Dynabeads Detection by Sensitive Element Based on Giant Magnetoimpedance," *Biosensors and Bioelectronics*, 20:1611-1616 (2005).
Lapointe et al., "Statis and Dynamic Properties of Magnetic Nanowires in Nematic Fluids," *J. Appl. Phys.*, 97:10 (2005).
Lu et al., "Nanophotonic Crescent Moon Structures with Sharp Edge for Ultrasensitive Biomolecular Detection by Local Electromagnetic Field Enhancement Effect," *Nano Lett*, 5:119-124 (2005).
McNaughton et al. "Sudden Breakdown in Linear Response of a Rotationally Driven Magnetic Microparticle and Application to Physical and Chemical Microsensing" (J. Phys. Chem. B, 110 (38), pp. 18958-18964 (2006).
McNaughton et al., "Fabrication of Uniform Half-Shell Magnetic Nanoparticles and Microspheres with Applications as Magnetically Modulated Optical Nanoprobes," arXiv:cond-mat/0506418v1, pp. 1-6 (2005).
McNaughton et al., "Physiochemical Microparticle Sensors Based on Nonlinear Magnetic Oscillations," *Sensors and Actuators B.*, 121:330-340 (2007).
Merkt et al., "Capped Colloids as Light-Mills in Optical Traps," arXiv:cond-mat/0605463v1, pp. 1-10 (2006).
Newman et al., "Motions of a Magnetic Particle in a Viscous Medium," *J. Appl. Phys.*, 39:5566-5569 (1968).
Nozawa et al., "Smart Control of Monodisperse Stöber Silica Particles: Effect of Reactant Addition Rate on Growth Process," *Langmuir*, 21:1516-1523 (2005).
Olsvik et al., "Magnetic Separation Techniques in Diagnostic Microbiology," *Clinical Microbiology Reviews*, 7:43-54 (1994).

(56) References Cited

OTHER PUBLICATIONS

Paul et al., "Stochastic Dynamics of Nanoscale Mechanical Oscillators Immersed in a Viscous Fluid," *Phys. Rev. Lett.*, 92:235501-1-235501-4 (2004).

Petkus et al., "Detection of FITC-Cortisol via Modulated Supraparticle Lighthouses," *Anal. Chem.*, 78:1405-1411 (2006).

Puig-de-Morales et al., "Measurement of Cell Microrheology by Magnetic Twisting Cytometry with Frequency Domain Demodulation," *J. Appl. Physiol.*, 91:1152-1159 (2001).

Purcell et al., "Life at Low Reynolds Number," *Am. J. Phys.*, 45:3-11 (1977).

Rife et al., "Design and Performance of GMR Sensors for the Detection of Magnetic Microbeads in Biosensors," *Sensors and Actuators A.*, 107:209-218 (2003).

Shankar et al.,"Experimental Determination of the Kinematic Viscosity of Glycerol-Water Mixtures," *Proc. R. Soc. Lond. A.*, 444:573-581 (1994).

Shelton et al., "Nonlinear Motion of Optically Torqued Nanorods," *Phys. Rev. E.*, 71:036204-1-036204-8 (2005).

Shen et al., "In situ Detection of Single Micron-Sized Magnetic Beads using Magnetic Tunnel Junction Sensors," *Appl. Phys. Letts.*, 86:253901-1-253901-3 (2005).

Stober et al., "Controlled Growth of Monodisperse Silica Spheres in the Micron Size Range," *J. Coll. Interface Sci.*, 26:62-69 (1968).

Verbridge et al., "High Quality Factor Resonance at Room Temperature with Nanostrings Under High Tensile Stress," *J. Appl. Phys.*, 99:124304-1-124304-8 (2006).

Vignola et al., "Effect of Viscous Loss on Mechanical Resonators Designed for Mass Detection," *Appl. Phys. Lett.*, 88:041921-1-041921-3 (2006).

Waigh, "Microrheology of Complex Fluids," *Rep. Prog. Phys.*, 68:685-742 (2005).

Yamazaki et al., "Three-Dimensional Analysis of Swimming Properties of a Spiral-Type Magnetic Micro-Machine," *Sensors and Actuators A.*, 105:103-108 (2003).

Zhao et al., "A Rapid Bioassay for Single Bacterial Cell Quantitation Using Bioconjugated Nanoparticles," *PNAS*, 101:15027-15032 (2004).

\* cited by examiner

Fluorescence excitation (A) and emission (B) spectra of various endogenous tissue fluorophores. Spectral shapes are shown for the best relative excitation/emission conditions (derived from Richards-Kortum and Sevick-Muraca (8), Wolfbeis (11) and Bottiroli et al. (78)).

From Wagnieres; Star, and Wilson 1998

Figure 3
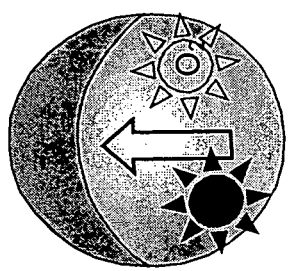
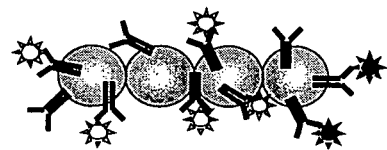
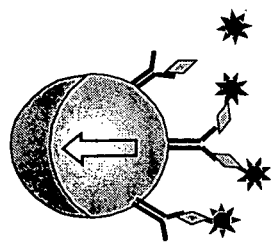
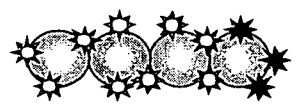

Bright field

Magnetophoretically Modulated Particles Inside a Nanobottle

Modulated Probes Inside Nanobottles

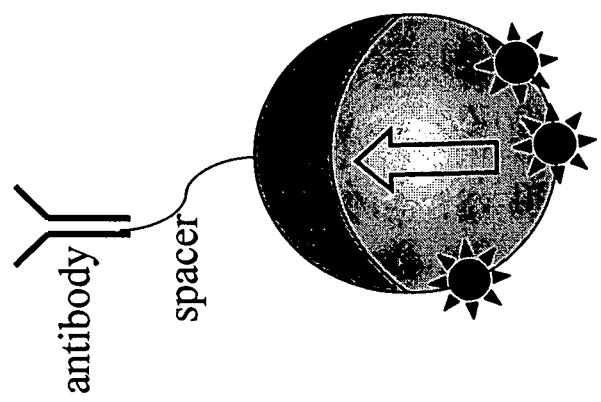
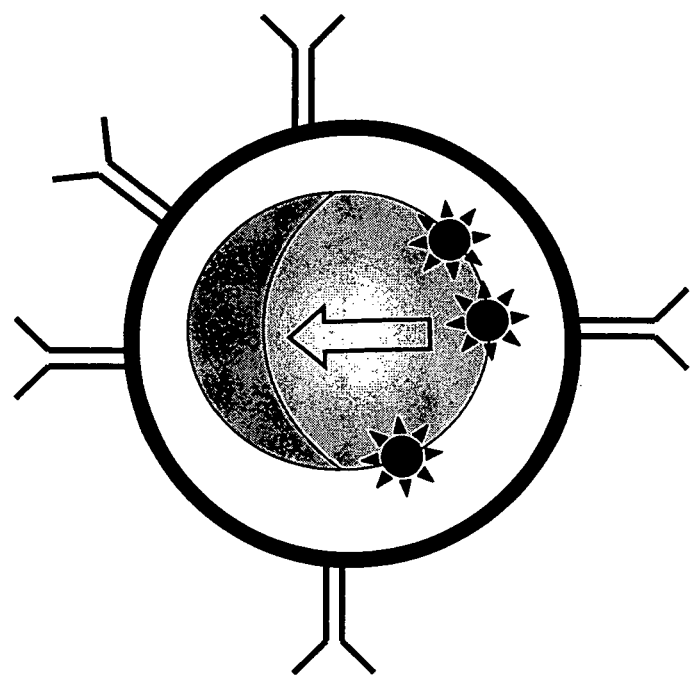
Figure 23

Gradient sensitive probe molecules

MODULATED PHYSICAL AND CHEMICAL SENSORS

This application is a continuation in part of copending application Ser. No. 10/419,033, filed Apr. 18, 2003, which claims priority to provisional patent application Ser. No. 60/373,492, filed Apr. 18, 2002.

This invention was made with government support under contract C007013 awarded by the National Institutes of Health and Grant 9900434 awarded by the National Science Foundation. The Government has certain rights in the invention.

FIELD OF THE INVENTION

The present invention relates to modulated (e.g., magnetically modulated) chemical sensors. In particular, the present invention relates to particles comprising fluorescent indicator dyes and methods of using such particles.

BACKGROUND

Fluorescence is the most sensitive molecular detection and chemical imaging method available today. It is used to image even single molecules, in real time, with high spatial and spectral resolution, at ambient conditions, and with little perturbation. It also facilitates the detection and identification of pathogens, development of drugs, and other biomedical applications. Fluorescent dyes are commonly used to study intracellular chemical concentration changes, to measure immunochemical concentrations in a sample, to tag molecules on the surface of cells and in tissues, and in fundamental research on protein folding mechanisms. Nevertheless, typical background fluorescence from sample and instrument optics makes detecting and distinguishing low levels of fluorescence and small changes in fluorescence a challenging endeavor. Background fluorescence has hampered use of fluorescence measurement techniques in all areas and has fuelled development of red-exciting dyes, two photon excitation sources, chemiluminescent dyes, and innovative schemes and expensive equipment to bring background noise down to manageable levels.

It is an ultimate goal of medicine and biology to determine how cells function, and what effect drugs and other exogenous stimuli may have on them. Towards this goal, one must measure the chemical composition of cells in various conditions and environments (Taylor et al., Current Opinion in Biotechnology. 2001 February; 12(1):75-81). Chemicals of interest include pH that affects enzyme reactions; sodium, potassium, calcium, chloride ions and nitric oxide that are important in neuron signaling and osmosis; oxygen, carbon dioxide, ethanol, and glucose that are important in respiration; reactive oxygen species that are important for aging and photodynamic therapy; in addition physical characteristic such as temperature may also be measured. Biological macromolecules such as DNA, RNA, carbohydrates, and neurotransmitter proteins may also be detected. It is important to be able to detect multiple analytes at the same location at the same time in order to fully understand any physiological responses. It is also useful to detect at specific locations since analyte concentrations are often inhomogeneous.

In medical and biochemical research, when the domain of the sample is reduced to micrometer regimes, e.g. living cells or their subcompartments, the real-time measurement of chemical and physical parameters with high spatial resolution and negligible perturbation of the sample becomes extremely challenging. A traditional strength of chemical sensors (optical, electrochemical, etc.) is the minimization of chemical interference between sensor and sample, achieved with the use of inert, "biofriendly" matrices or interfaces. However, when it comes to penetrating individual live cells, even the introduction of a sub-micron sensor tip can cause biological damage and resultant biochemical consequences. In contrast, individual molecular probes (free sensing dyes) are physically small enough but usually suffer from chemical interference between probe and cellular components.

Perhaps the easiest way to measure cells' compositions is to grind up cells into a puree and analyze the puree's composition using electrochemical sensors, titration with indicator dyes, electrophoresis, or other means. However, blending the cells kills them, and makes it difficult to follow processes that may happen to living cells. In addition, grinding and blending the cells together makes it difficult to analyze different parts of a cell separately.

Microelectrodes and electrodes can measure chemical concentrations in living cells or in biological tissue, but they have a number of problems. Inserting the probe into the cell is invasive, and may kill the cell or affect how it functions. A reference electrode is required to make electrical measurements and proper placement and calibration of the reference electrode complicates the process. In addition, each microelectrode can only measure concentrations near the tip of the probe, so a single probe cannot show the spatial distribution of chemicals in a cell. In principle, multiple probes could be inserted to determine chemical concentrations at many points, however, each additional probe is successively more invasive, and most cells are too small to take more than one or two probes.

To form an image showing the distribution of chemical species in a cell, it is now a common practice to inject fluorescent indicator dyes into cells. The intensity, peak wavelength, polarization anisotropy, or lifetime of the dye fluorescence indicates chemical concentrations. Unfortunately, many fluorescent indicator dyes suffer from a number of problems. Many intensity indicator dyes (intensity is the most commonly used dye property) lack an internal reference so it is impossible to tell whether a strong intensity is due to a high analyte concentration or a large amount of dye.

Another problem with free dye is that the cellular environment can affect the fluorescence. Cellular proteins often quench dye fluorescence, affecting readings unpredictably. The dye may preferentially adhere to certain structures in a cell, making readings unrepresentative. In addition, the dye may be sequestered from the cell making readings for non-ratiometric probes change in time. Another problem with free dyes is that they may affect cell function or may poison the cell. Since each free dye interacts with a cell in its own way, the interaction needs to be studied for each type of dye and cell to ensure an accurate reading.

However, most fluorescent indicator dyes have broad excitation and emission peaks that limit the number of different dyes that can be detected without having some of the fluorescence from the different dyes overlap. This limits the number of analytes that can be detected independently at any given time.

Thus, improved methods for studying cells and intracellular analytes are needed. Such improved methods should be amenable to monitoring the cell at more than one location and should have minimal toxicity.

SUMMARY OF THE INVENTION

The present invention relates to modulated (e.g., magnetically modulated) chemical sensors. In particular, the present invention relates to particles comprising fluorescent indicator dyes and methods of using such particles.

Accordingly, in some embodiments, the present invention provides a composition comprising a half-shell probe with arches, the probe comprising a matrix and a metal half-shell coated on the surface of the matrix; the metal half-shell further comprising arch-shaped cusps. In some embodiments, the probe further comprises a label (e.g., embedded or attached to the surface). In some embodiments, the metal is magnetic.

In further embodiments, the present invention provides a method, comprising: providing a plurality of probes comprising a matrix coated with a metal half-shell; a device configured for the detection of different fluxes of light generated from the probes in different probe orientations; and a sample suspected of comprising an analyte object of interest; and contacting the sample with the probes under conditions such that the analyte object binds to the plurality of probes; and detecting the different fluxes of light with the device to generate modulated probe signal and unmodulated background signal. In some embodiments, the probes comprise a matrix and metal half-shell. In some embodiments, the probes further comprise a label (e.g., an indicator dye) comprising a labeling particle attached to the probes. In some embodiments, the method further comprises the step of separating the modulated signal from unmodulated background signal. In some embodiments, the method further comprises the step of identifying the analyte object based on the level of modulated probe signal. In some embodiments, the sample is the inside of a cell, a tissue, a bodily fluid, a surface, or a cellular homogenate. In some embodiments, the different orientations comprises orientation in the direction of a magnetic field. In other embodiments, the different orientations comprises orientation by Brownian motion. In some embodiments, the analyte object is a bacteria, a virus, a fungus, a protein or a nucleic acid.

The present invention additionally provides a method of producing uniform magnetic half-shell particles comprising: providing uniform particles; a substrate; and a device configured to vapor deposit magnetic materials onto the substrate; depositing a layer of the particles onto the substrate; and depositing magnetic materials onto the particles using the device. In some embodiments, the plurality of particles have a coefficient of variation in particle radius of less that 20% and preferably less than 2%. In some embodiments, the substrate comprises a flexible material (e.g., film) wound onto a reel. The present invention also provides uniform magnetic particles generated by the method.

DESCRIPTION OF THE DRAWINGS

FIG. 3 shows a schematic of two types of MagMOONs where the fluorescent dye is used in different ways. (a) Metal-capped MagMOONs (i) for oxygen sensing in cells and tissues; (ii) for an immunoassay. (b) non-spherical MagMOONs (i) for oxygen sensing in cells and tissues; (ii) for an immunoassay.

FIG. 14A shows two methods of making disc shaped particles by crushing spherical particles between two flat sheets. FIGS. 14B and 14C show two methods of making elliptical disc shaped particles: by rolling a rolling pin over spherical particles (14B); and by pressing spherical particles between two co-rotating shafts (14C).

FIG. 23 shows a schematic of probes with antibodies attached to the outside of the nanobottle utilized in some embodiments of the present invention.

GENERAL DESCRIPTION OF THE INVENTION

Figure 1:
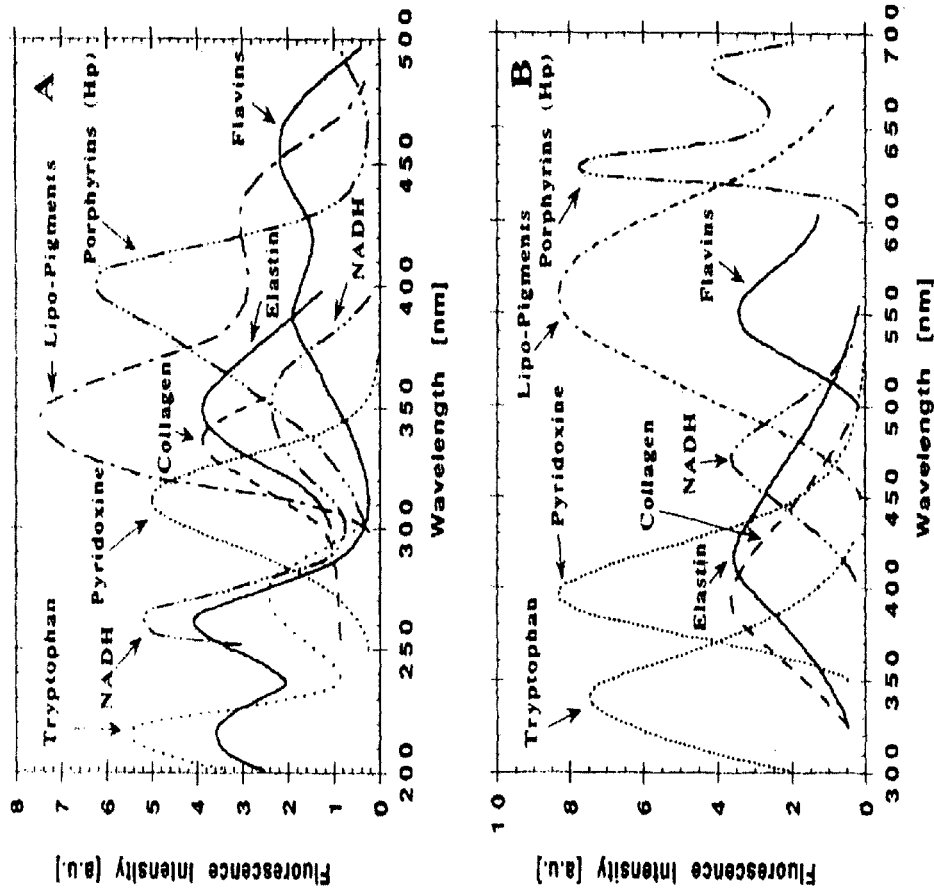
FIG. 1 shows excitation and emission spectra of molecules commonly found in cells.

The present invention relates to modulated (e.g., magnetically modulated) chemical sensors. In particular, the present invention relates to particles comprising labels (e.g., molecular tags or fluorescent indicator dyes) and methods of using such particles. The magnetically modulated or randomly moving chemical sensors of the present invention provide improved methods and compositions for sensing metabolic changes within cells. The chemical sensors of the present invention solve many of the problems of currently available methods for detecting changes within cells. The magnetically modulated or randomly moving chemical sensors of the present invention also provide improved methods and compositions for sensing minute quantities of biological macromolecules such as DNA and disease marking proteins in samples such as biological fluids and cell homogenates.

One significant problem of introducing fluorescent dyes into cells is the problem of background intracellular fluorescence. For example, cells contain naturally fluorescent chemicals that can obscure the signal of interest: one cannot tell if a fluorescent signal comes from the indicator dye, or the background unless one knows how large the background is. However, background is variable among cells and can change in time.

Fluorescence intensity measures the product of the amount of dye and the fluorescence per dye molecule. The fluorescence per molecule of an intensity based sensor dye indicates the concentration of analytes in the dye's environment. Most fluorescent indicator dyes, however, cannot distinguish between a chemical environment affecting the fluorescence per molecule, and dye concentration affecting the observed signal: many weakly fluorescent molecules could give the same total intensity as few strongly emitting molecules. There are a few ways of determining chemical concentrations based on fluorescence independent of the concentration of dye present. One way is to use ratiometric indicator dyes, which have two spectral peaks where the ratio of the two peak intensities depends on the chemical environment. The ratio of two peaks is independent of dye concentration and incident light intensity because these influence the intensity of both peaks equally.

Similarly, some indicator dyes have fluorescent lifetimes that vary with chemical concentration. Lifetime is useful because it is intrinsically ratiometric (e.g., the ratio of measured lifetimes, $\tau_0/\tau_1$, or the average lifetime measured should be independent of dye concentration).

Another way to make ratiometric measurements is to inject two different dyes into a cell, where one dye is sensitive to the chemical of interest, and the other is insensitive or relatively less sensitive and is used to normalize for dye concentration and incident light intensity. Compared to using a single ratiometric dye, using two dyes has the advantage that there are many more dyes to choose from, but has the disadvantage that the problems of each dye may be compounded, for instance, if the two dyes adhere to different cellular structures, or are sequestered from the cell at different rates, or bleach at different rates, quench each other, or are quenched differently by oxygen or different proteins, or poison the cell differently, then ratiometric readings may compound these errors.

Many of the disadvantages of free dye can be overcome by encapsulating dyes in inert polymer nanospheres as (e.g., PEBBLEs, See e.g., U.S. Pat. No. 6,143,558, herein incorporated by reference). PEBBLES (Probes Encapsulated By Biologically Localized Embedding) usually range in size from 20 nm to 2 µm, and can contain multiple dyes inside them as well as coatings and antibodies on the outside. The dyes may be either physically trapped inside pores in the polymer matrix, or chemically bound to the matrix. Pores in the polymer matrix are large enough to allow chemical species of interest to diffuse into the PEBBLES, but small enough to prevent large proteins from entering, or large physically trapped dye molecules from escaping.

Advantages of PEBBLEs include that the polymer capsule is inert, and is not toxic to the cell, nor does it react with anything in a cell. Proteins cannot quench dyes in PEBBLES, as the pores are too small to let the proteins in. As a result, there are few interactions between dye and cell. In addition, all PEBBLES should behave the same way inside a cell, regardless of the type of dye they have inside them since the chemical composition of the matrix is unchanged by the presence of dye, while the dye is unable to escape and react with the cell. pH, oxygen, sodium, calcium, potassium, chloride and glucose sensing PEBBLEs have been generated. Ratiometric PEBBLEs have been shown to be insensitive to proteins that usually quench free dye.

PEBBLES may contain a number of components in addition to dyes. For instance, antibodies can be attached to the outside of PEBBLES to deliver them to specific sites; ionophores and enzymes can be added to PEBBLES to make them sensitive to more chemical species; magnetic particles may be added to guide particles to places of interest, and for purposes described in this patent; reactive groups can be added to the PEBBLES so that they can react with other particles to form hybrid particles.

Many different dyes can be added to the same PEBBLE, allowing simultaneous measurement of different chemical species, and ratiometric measurement if one spectral peak is independent of analyte concentration. Nonetheless, the number of analytes that can be measured simultaneously is usually limited by the spectral overlap between dyes. In addition, traditional PEBBLEs are only accurate in samples with little intrinsic background (although sometimes dyes can be chosen which excite at places where there is little background expected).

There are many types of background that may interfere with fluorescent signal analysis. External sources include stray room light that enters the system, filters and optics in measurement instruments that fluoresce, excitation sources that are not entirely cut off using filters, and offsets in electronics. These external backgrounds can be overcome by using better equipment, by working in a dark room, by doing careful background subtraction with non-fluorescent samples having similar optical properties and shapes, and by using identical lens configurations. Such background subtraction requires preparation of a second reference sample, and switching between samples. Imprecise background subtraction, electronic drifts, and 1/f (flicker) noise limit the most sensitive fluorescent measurements. However, autofluorescence is usually more of a problem than external backgrounds or flicker noise.

In contrast to external background signals, cell autofluorescence is much more difficult to deal with, since it varies from cell to cell, varies spatially within a cell, and may change in time especially if conditions change in or around the cell (as most experiments require). Cell autofluorescence may come from structural components of a cell such as collagen and elastin, molecules involved in cellular metabolism such as NADH and flavins, and other sources. Such autofluorescence can emit over the entire visible spectrum (FIG. 1; Wagnieres et al., Photochemistry and Photobiology. 1998; 68(5):03-632), with fluorescence lifetimes from 0.28 ns (Richards-Kortum and Sevickmuraca 1996). In addition, plant cells contain chlorophyll and phycobilin, proteins that fluoresce very strongly. Autofluorescence is even more problematic in thick samples, as they contain many cells that all autofluorescence. Confocal techniques can eliminate much out-of-focus light, but the technique rejects much of the desired signal in the process. Thick tissue also suffers from scattering and absorption, distorting both images and spectra.

Since it is difficult to predict how large the background from a cell or tissue should be relative to the fluorescence of an indicator dye, a great deal of effort goes into finding ways of avoiding the background. Most of these methods involve using dyes that don't excite or emit light at common autofluorescence frequencies or timescales (or choosing the sample to fit the dye).

One way to reduce background fluorescence is to use dyes that excite at long wavelengths where autofluorescence from cells is usually small. However, long wavelength exciting dyes form just a small subset of possible dyes, and dyes that are passed up because they excite at shorter wavelengths may have advantages. Possible advantages include better chemical selectivity, more appropriate sensitivity or dynamic ranges, a ratiometric peak, high quantum efficiency and absorptivity, more photostability, and cheap and easy production. In addition, fewer analytes can be detected independently (without overlap in excitation or emission spectra) if the excitation and emission bandwidths are limited to the visible and near infrared frequencies.

A similar background problem exists for lifetime dyes. Although lifetime is intrinsically ratiometric (the lifetime is independent of the dye concentration), most fluorescent dyes have picosecond to nanosecond lifetimes (the same as most cell autofluorescence), making it difficult to distinguish the dye from the cell background. Progress has been made on making indicator dyes with microsecond and millisecond lifetimes, which can easily be distinguished from autofluorescence, however only a few long-lived indicator dyes have been synthesized to date, and these usually have small absorption cross-sections and low quantum efficiencies.

Some crystals and molecules can convert multiple photons into single higher frequency photons. Fluorescent dyes or photodynamic dyes to up-converting phosphors and exciting the dyes with up-converted light from the phosphors (U.S. Pat. No. 6,159,686, herein incorporated by reference). Since cells contain few natural up-converting dyes, the phosphors are practically the only source of high frequency light, and the dyes attached to the phosphors are excited far more readily than more distant naturally fluorescent molecules in the cell. As a result, most of the background is eliminated. However, the method is new and relatively untested. The quantum efficiency of most up-converters is low, so the signal from the particles is weak.

Another way to avoid background is to use chemiluminescent dyes. Chemiluminescent dyes emit light as they react, and do not require any excitation source. Since they do not require an excitation source, the chemiluminescence is virtually background free. However, very few dyes are known to undergo chemiluminescence, these react with only a few specific chemicals, and the dyes are usually used up as they react. Chemiluminescent dyes emit less than one photon per molecule (4-5 orders of magnitude) less than fluorescent dyes, and require expensive equipment and long exposure times to detect.

Raman Spectroscopy has many advantages over fluorescence spectroscopy. At room temperature, Raman spectra are much sharper than fluorescence spectra, allowing better identification of proteins and determination of their local states. In addition, molecules under Raman excitation bleach far less readily than molecules that are fluorescing. The main problem with Raman spectroscopy is that Raman signals are approximately $10^{14}$ times weaker than fluorescent signals, so Raman signals are often drowned out by background fluorescence. Proteins adsorbed onto the surface of certain metal nanoparticles have a surface enhanced Raman signal $10^{14}$-$10^{15}$ times greater than signal in solution, making the Raman signal similar in magnitude to fluorescence (Nie and Emery Science. 1997; 275(5303): 1102-1106). Recently, surface enhanced Raman spectroscopy (SERS) was used to identify and image Raman signals from native DNA, RNA, phenylanine, tyrosine, and other molecules adsorbed onto gold nanoparticles within a single cell (Kneipp et al., Applied Spectroscopy. 2002 February; 56(2):150-154).

Changes in biochemistry are both symptoms and causes of disease. Measuring chemical concentrations in thick tissue is extremely useful for clinical diagnosis and research. However, it is more difficult to make fluorescence measurements in thick tissues than in cells. Scattering and absorption can distort the emission spectrum from a dye by absorbing some frequencies more than others. Methods are being formulated to account for scattering and absorption in order to reconstruct emission spectra and lifetimes (Mayer et al., Applied Optics. 1999; 38: 4930-4938). However, these methods cannot account for autofluorescence. Autofluorescence from a thick sample is much larger than from single thin cells since it comes from many cells. In addition, scattering and absorption attenuate light from fluorophores buried in tissue, further decreasing the signal strength relative to the autofluorescence. These difficulties prevent all but a few fluorescent chemical probes from being used in thick tissue, although the autofluorescence itself can help to detect atherosclerosis and neoplasia (Richards-Kortum and Sevickmuraca, Annual Review of Physical Chemistry. 1996; 47:555-606).

MRI can measure pH of tissues, and oxygenation of the blood. However, most other analytes cannot be measured using MRI, the resolution may be insufficient for certain experiments, and the equipment is expensive. Other methods of determining chemical concentrations in thick tissue include microelectrodes and optical fibers, however theses are invasive, may be difficult to place in certain regions, and can only measure concentrations where they are placed, not over a large region in order to form an image.

Attaching antibodies to fluorescent microparticles to guide them to selected sites on cells and in tissues may help in the early diagnosis and treatment of cancer (Bornhop et al., Journal of Biomedical Optics. 2001; 6(2):106-115). Failure to diagnose cancers early often seriously decreases chances of survival. In addition, many treatments rely on delivering drugs containing microspheres to the tumor. However, it is difficult to determine where exactly the particles localize. Fluorescence may help in this endeavor (Jain, Clinical Cancer Research. 1999; 5(7): 1605-1606).

Detecting multiple analyte signals at the same location is another goal the sensor community has struggled with. To do so using fluorescence, one has to be able to distinguish the fluorescence from each indicator dye. Fluorescence is most easily distinguished if the excitation or emission spectra of the dyes do not overlap. However, since most dyes have broad spectra, it becomes challenging to find a combination of dyes that both have the desired sensing properties, and have spectra that do not overlap. Detecting more than two chemicals ratiometrically requires much care and effort.

Even if two dyes have spectral peaks that overlap, as long as their shapes are different, it is possible to calculate how much of the observed spectrum was created by each dye using deconvolution algorithms. However, the result from deconvolution is sensitive to background signal strength. In addition, the process requires measurement at many wavelengths.

One can distinguish between dyes with similar spectra on the basis of their fluorescent lifetimes provided that their lifetimes are significantly different. However, this is difficult to do unless one of the dyes has a lifetime of several microseconds or more, which is rare. In principle, one could distinguish between different types of dyes with overlapping fluorescence on the basis of their photostability, saturation intensity, or temperature sensitivity. However, in practice these distinctions are often small and are difficult to measure controllably.

Fluorescence correlation spectroscopy is a means to measure diffusion coefficients. As molecules diffuse in and out of view (by Brownian motion), the number of molecules in view changes, causing fluctuations in the observed fluorescence intensity. Molecules or particles with rapid diffusion constants cause rapid fluctuations in intensity; molecules with slow diffusion constants cause slow fluctuations in intensity. By analyzing the autocorrelation function of the intensity fluctuations, it is possible to determine diffusion constants for molecules or particles. If there is more than one species present, fluorescence lifetime and color filtering can be used to distinguish between different species.

Early detection of disease and pathogens requires efficient detection of minute quantities of DNA/RNA, hormones, peptide, protein or complex carbohydrate in fluids isolated from affected organisms using non- or minimally-invasive techniques, e.g., sputum, mucous, serum or whole blood. As the number of available antibodies increases every year, more pathogens, diseases, and proteins can be detected in immunoassays. In many ways, fluorescent dyes are ideal immunoassay labels. Hundreds of fluorescent dyes are cheaply available and emit intense signals. Typically each fluorescent molecule can emit tens of thousands to hundreds of thousands of photons before photodestruction. However, background fluorescence from biological samples and instrument optics limits the sensitivity of traditional fluorescent immunoassays. Removing background fluorescence requires extensive washing that is time consuming, adds complexity to the instrument, and is imperfect in real-world applications. Consequently, exotic labeling schemes requiring expensive, highly sensitive equipment, and often complicated procedures have to be developed. For highly sensitive detection, radiolabeled, chemiluminescent, and lifetime discriminating fluorescent systems are gaining prevalence.

Numerous immuoassay formats exist. In a sandwich-type assay, molecular recognition elements (e.g., antibodies) are attached to a solid surface. A biological sample is applied to the surface to bind the analytes (e.g., antigens) to the surface bound antibodies. The analytes are also tagged with a fluorescent, chemiluminescent, or radioactive dye. Then, the surface is washed several times to flush away excess dye and autofluorescent compounds. The amount of dye that remains attached is measured to quantify the amount of analyte in solution. Similarly, in a competitive assay, the tags compete with the analyte for binding sites on the surface: they label any binding sites to which the analyte does not attach.

Radioactive tags are often used as a replacement for fluorescent dyes. The tags employ material that spontaneously undergoes alpha, beta or gamma decay and the amount of radiation emitted is measured to determine analyte concentration. An advantage of radio-tags over fluorescent dyes is the minimal natural background radiation that interferes with readings. However, the tags are difficult to work with and must be prepared on site, especially if they have short half-lives. Conversely, if they have long half-lives, long detection times may be required to obtain a good signal. It is also difficult to produce high-density arrays for high throughput radio-immunoassays because the radiation from one assay can easily leak into a neighboring detector.

Magnetic microparticles may be used as a replacement for dyes to tag analytes or unoccupied binding spaces in sandwich or competitive type assays. Magnetic permeability, resistance of Giant Magnetoresistive (GMR) films, Magnetic Resonance Imaging (MRI), and AFM cantilevers have all been used to detect magnetic particles attached to a surface. Magnetic detection offers the advantage over fluorescent detection that biological samples do not produce magnetic background signals. GMR and AFM cantilever sensors have the highest sensitivity, being able to detect single 2.8 µm magnetic particle bindings. However, they have a limited dynamic range and it is difficult to detect submicron particles, since the magnetic moment of the particles decreases with volume. MRI and magnetic permeability have a large dynamic range, but low sensitivity compared with fluorescence. MRI is expensive and magnetic susceptibility measurements also depend on particle position. All these methods reduce selectivity and dynamic range compared to fluorescent sensors because one non-specific binding event between a particle and the surface will attach the particle with the same measured response as multiple specific binding events between the same particle and surface. In addition, most currently available magnetic microspheres have significant variation in magnetic content for different microspheres in the same batch, making it difficult to count low numbers of particles. In contrast to fluorescent dyes, magnetic tags are difficult to distinguish, so only one experiment may be performed at a time.

Cells and proteins attached to magnetic particles may be magnetically pulled from suspension and washed to remove excess fluorescent dye and autofluorescent components of the sample. The analytes can subsequently be evaluated using standard fluorescence or other techniques. Some 30 companies produce magnetic microspheres for cell separation and immunoassay applications (e.g., Magnetic Microsphere). Although the magnetic separation techniques are effective, uncoupled magnetic separation and optical evaluation make instruments unnecessarily complex. The separation takes time, especially for sub-micron particles with small magnetic moments. In addition, the technique cannot be used within cells or tissues and is no help at overcoming instrument fluorescence and electronic background signals.

Techniques exist to measure translational diffusion of fluorescent particles in cells and solution. However, no effective technique exists to measure reorientation rate of single particles in the 40-5 µm range. Moller et al. (Moller et al., Toxicology and Applied Pharmacology. 2002 August; 182 (3):197-207) calculated bulk rotational viscosity (and active forces within a cell pulling on phagosomes) by measuring the amount of time it takes for the magnetic vector from 1.8 µm magnetic particles to rotate inside macrophages: it was found that certain drugs affected the rigidity of the cytoplasm, and that ingestion of small particulates of different types of materials affected the viscosity of the macrophages. However, a million macrophages and 10 µg of magnetic material were used to get this global measurement. Thus this method requires expensive sensitive equipment that lacks the sensitivity and resolution to measure rotational viscosity in single cells or to track the particles' locations, or to correlate viscosities to any chemical changes inside the phagosome or cytoplasm.

The present invention is able to overcome many of these problems by providing magnetically modulated optical nanoprobes (MagMOONs) and/or by providing systems for successfully employing detection of particles based on Brownian motion. The MagMOON principle enables sensitive detection of any optical signal (e.g., fluorescent signal) from a MagMOON. The fluorescent signal may come from an indicator dye that measures concentrations of ions, oxygen, or glucose around the particle as shown in FIG. 3, or from a PEBBLE attached to the MagMOON. Alternatively, the signal may come from a fluorescent dye that binds to antigens that bind to the outside of antibody-coated MagMOONs in a sandwich immunoassay as shown in FIG. 3. Alternatively, the blinking signal may come from particles that change their modulation characteristics when they bind to a substrate (for example by blinking when they bind). The fluorescent signal may even be a signal from surface enhanced Raman spectroscopy of molecules adsorbed directly on to the MagMOON surface. The fluorescent signal may be an analyte indicator, a cell label, or an internal roving light source. The MagMOON may be used in fluid samples, cell, and tissues. It may be used in microwell arrays, or flow cytometers.

In other embodiments, the present invention provides Brownian modulated optical nanoprobes (Brownian MOONs). Brownian MOONs are modulated by Brownian motion. In some embodiments, MagMOONs in the absence of a magnetic field or other modulation act as Brownian MOONs.

DEFINITIONS

To facilitate understanding of the invention, a number of terms are defined below.

As used herein, the term "MagMOON" refers to "magnetically modulated optical nanoprobes." MagMOONs are micro- and nano-particles that have optical properties (fluorescence excitation and emission spectra, fluorescence polarization, fluorescence lifetime and anisotropy, Raman spectra, and optical absorption, reflection, and scattering) that are modulated by magnetic field orientation or magnetic field gradient.

As used herein, the term "label" refers to any particle or molecule that can be used to provide a detectable (preferably quantifiable) effect. In some embodiments, labels utilized in the present invention detect a change in the, polarization, position, fluorescent, reflective, scattering or absorptive properties of the probes of the present invention. In some embodiments, the label comprises indicator dyes, enzymes, molecular recognition elements capable of synergistic sensing mechanisms and non-perturbative measurements, as well as fluorescent quantum dots and reflective gold and silver nanoparticles. In some embodiments, the label is integral to the probe. In other embodiments, it is attached to the surface of a probe (e.g., a "labeling particle"). In some embodiments, the label is an "indicator dye." In some embodiments, the label is a "molecular tag." In some embodiments, labels attach to the probes in the presence of analyte (e.g., fluorescently labeled antibodies attach to the probes in the presence of antigen bound to the probe). In some embodiments, the label is a native intracellular Raman active molecule.

As used herein, the term "molecular tag" refers to a label that binds selectively to specific proteins. Molecular tags may be used to tag MagMOONs or other particles in the presence of analyte. Alternatively, MagMOONs may serve as molecular tags by binding to specific locations in cells and tissues.

As used herein, the term "labeling particle" refers to a particle attached to a MagMOON or Brownian particles that serves as a label. The particle may be attached using any suitable method including, but not limited to, covalent attachment, adsorption, or embedded (e.g., "embedded sub-nanometer particles").

As used herein, the term "untethered probe" refers to a probe configured to be suspended in a sample and optically interrogated without physical links (e.g., wires or optical fibers) to the outside of the sample.

As used herein the term label refers to any agent or inherent property of a composition that provided a detectable signal. Examples include, but are not limited to, indicator dyes, combinations of indicator dyes, ionophores, and enzymes configured to create sensitivity to new analytes and inherent photon detectability based on physical properties (e.g., shape, composition) of a probe.

As used herein, the term "a sensing agent" refers to a label configured to produce a detectable response when exposed to an analyte in its environment.

As used herein, the term "indicator dye" refers to any dye that changes an optical characteristic in response to a concentration of analyte in its environment. Optical characteristics include, but are not limited to, fluorescence intensity, position of a spectral peak, fluorescence lifetime and anisotropy, fluorescence polarization, and Raman spectral shape and intensity. In some preferred embodiments, indicator dyes are fluorescence indicator dyes. The dyes may excite in the ultraviolet, visible, or infrared. The dyes may detect the analyte directly, or in combination with ionophores, enzymes, other fluorophores or fluorescence quenchers.

As used herein, the term "spectral intensity" refers to an optical signal at one or more than one spectral wavelength. Optical signals include but are not limited to fluorescence, absorbance, reflection, and Raman spectral signals.

As used herein, the term "magnetic probe" refers to any probe that is capable of being altered in a magnetic field. In some embodiments, the probes are permanently magnetized. In other embodiments, the probes are magnetized only in the presence of an external magnetic field.

As used herein, the term "magnetically modulated" refers to a signal that is controlled and changed by a changing magnetic field orientation or gradient. The invention is not limited by the modulation waveform. The magnetic field may rotate continuously in one direction, or alternate direction. It may rotate a complete circle, or a small angle. It may rotate at a constant rate, or a changing rate, or may rotate rapidly to a particular orientation, pause while data is collected, and then rotate rapidly to a new orientation.

As used herein, the term "gradient sensing probes" refers to probes that are modulated by magnetic field gradients. In some embodiments, particles are pulled back and forth by magnetic field gradients and the fluorescent signal at one location fluctuates on and off as the particles pass in and out of view. In some embodiments, gradient sensing probes contain FRET donor and acceptor molecules that provide a change in fluorescence signal in response to small changes in molecule (e.g., a DNA molecule) tension which tension is modulated by magnetic field gradients.

As used herein, the term "orienting agent" refers to all means of physically altering a probe in order to allow the probe to be oriented in a magnetic field, including but not limited to, the use of magnetic probes, the embedding of magnetic material in a non-magnetic probe, or the vapor deposition of magnetic material onto probes.

As used herein, the term "a device configured for the detection of said labels" refers to any device suitable for detection of a signal from labels that are in communication with the magnetic probes of the present invention. In some embodiments, the device includes an orienting component configured to rotate the magnetic probes and a detection component configured to detect a signal from the label (e.g., a fluorescent indicator dye).

As used herein, the term "nanobottle shell" refers to a shell of material that is suitable for encapsulating a plurality of probes of the present invention. In preferred embodiments, the pores in the nanobottle allow for the flow of small molecule analytes, but do not allow for the flow of the probes. Nanobottles may be composed of any suitable material, including, but not limited to, those disclosed below.

As used herein, the term "gradient sensing probes" refers to probes that are sensitive to small changes in molecule tension. In some embodiments, gradient sensing probes contain FRET donor and acceptor molecules that provide a change in fluorescence signal in response to small changes in molecule (e.g., a DNA molecule) tension.

As used herein, the term "sub-nanometer particle" refers to a particle that is smaller than a nanometer in diameter and is capable of being embedded into a probe of the present invention (e.g., by rolling as disclosed herein).

As used herein, the term "instructions for using said probes to detect an analyte in a sample" includes instructions for using the probes contained in the kit for the detection of any suitable "analyte." In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination. Additional information is available at the Internet web page of the U.S. FDA.

The phrase "exogenous cellular stimulus" means a stimulus exogenous to a cell that is capable of stimulating the cell. By "stimulating the cell" is meant that the status of the intracellular analytes of the cell is changed (e.g., the concentration is changed). Such stimuli include, but are not limited to a variety of noxious, pathogenic and trophic stimuli. In one embodiment, the stimulus is a toxic agent (or "toxicant"). In another embodiment, the toxic agent is a biological toxin.

As used herein, the term "biological macromolecule" refers to large molecules (e.g., polymers) typically found in living organisms. Examples include, but are not limited to, proteins, nucleic acids, lipids, and carbohydrates.

As used herein, the term "molecular recognition element" refers to any molecule or atom capable of detecting a "biological macromolecule." In some embodiments, molecular recognition elements detect biological macromolecules present in or attached to the surface of intact cells or tissue. In other embodiments, molecular recognition elements detect biological macromolecules in vitro. In some embodiments, molecular recognition elements are antibodies.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, $F(ab')_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, $F(ab')_2$ fragments, and Fab expression libraries; and single chain antibodies.

The term "epitope" as used herein refers to that portion of an antigen that makes contact with a particular immunoglobulin. When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

As used herein, the term "analyte" includes any substance within a cell. Analytes of particular interest include (but are not limited to) intracellular ions (i.e. $H^+$, $Na^+$, $K^+$, $Ca^{++}$, $Zn^{++}Cl^-$,), as well as oxygen and glucose, as well as "biological macromolecules." However, analytes can also exist outside of cells (e.g., in a test tube).

The term "chemical reaction" means reactions involving chemical reactants, such as inorganic compounds.

The term "microorganism" as used herein means an organism too small to be observed with the unaided eye and includes, but is not limited to bacteria, viruses, protozoans, fungi, and ciliates.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

A "solvent" is a liquid substance capable of dissolving or dispersing one or more other substances. It is not intended that the present invention be limited by the nature of the solvent used.

As used herein, the term "polymer" refers to material comprised of repeating subunits. Examples of polymers include, but are not limited to polyacrylamide and poly(vinyl chloride), poly(vinyl chloride) carboxylated, and poly(vinyl chloride-co-vinyl acetate co-vinyl) alcohols.

As used herein, the term "polymerization" encompasses any process that results in the conversion of small molecular monomers into larger molecules consisting of repeated units. Typically, polymerization involves chemical crosslinking of monomers to one another.

As used herein, the term "sol-gel" refers to preparations composed of porous metal oxide glass structures. Such structures can have biological or other material entrapped within the porous structures. The phrase "sol-gel matrices" refers to the structures comprising the porous metal oxide glass with or without entrapped material. The term "sol-gel material" refers to any material prepared by the sol-gel process including the glass material itself and any entrapped material within the porous structure of the glass. As used herein, the term "sol-gel method" refers to any method that results in the production of porous metal oxide glass. In some embodiments, "sol-gel method" refers to such methods conducted under mild temperature conditions. The terms "sol-gel glass" and "metal oxide glass" refer to glass material prepared by the sol-gel method and include inorganic material or mixed organic/inorganic material. The materials used to produce the glass can include, but are not limited to, aluminates, aluminosilicates, titanates, ormosils (organically modified silanes), and other metal oxides.

As used herein, the term "liposome" refers to artificially produced spherical lipid complexes that can be induced to segregate out of aqueous media. The terms "liposome" and "vesicle" are used interchangeably herein.

As used the term "absorption" refers, in one sense, to the absorption of light. Light is absorbed if it is not reflected from or transmitted through a sample. Samples that appear colored have selectively absorbed all wavelengths of white light except for those corresponding to the visible colors that are seen.

As used herein, the term "spectrum" refers to the distribution of electromagnetic energies arranged in order of wavelength.

As used the term "visible spectrum" refers to light radiation that contains wavelengths from approximately 360 nm to approximately 800 nm.

As used herein, the term "ultraviolet spectrum" refers to radiation with wavelengths less than that of visible light (i.e., less than approximately 360 nm) but greater than that of X-rays (i.e., greater than approximately 0.1 nm).

As used herein, the term "infrared spectrum" refers to radiation with wavelengths of greater 800 nm.

As used herein, the term "analyte object" refers to an object within a sample that will induce an effective change in resistance to rotation for a particle upon binding to the particle. Examples include, but are not limited to viruses, eukaryotic cells, prokaryotic cells, fungus, subcellular organelles, cytoskeleton, macromolecules, and molecules (e.g., proteins or nucleic acids)."

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DESCRIPTION OF THE INVENTION

The present invention provides MagMOON and Brownian MOON particles containing labels (e.g., fluorescent indicator dyes) to measure local chemical concentrations and magnetic material to move the particles and modulate the fluorescent signal. In some preferred embodiments, these particles orient in an external magnetic field, and rotate in response to a rotating magnetic field or undergo random motion. They are also made to preferentially excite and emit fluorescence in certain directions (e.g. the North side of the particle) by coating one side of the particle (e.g., with aluminum), or bleaching one side of an opaque particle, or making non-spherical particles. When they rotate, a faced observer sees their fluorescence blink on and off, as their light emitting sections) come and go from view. Lock-in amplifiers or software analysis of a time series of images or spectra separate this blinking signal from steady background fluorescence and from noise at other frequencies. The probes can measure chemical concentrations in samples with high background signals such as thick biological tissue, plant cells and most cells that are excited with ultraviolet light. They are also insensitive to stray room light, internal instrumental reflections, and other background. The present invention also provides particles for the independent measurement of multiple chemical species by utilizing chemical sensors that blink at a different frequencies or phases or if one type of sensor is optically polarized while others are directionally emitting. In another embodiment, particles are pulled back and forth by magnetic field gradients and the fluorescent signal at one location fluctuates on and off as the particles pass in and out of view. Methods of producing non-spherical and hybrid particles are also disclosed.

The present invention also provides methods of utilizing the Mag and Brownian MOON particles for a variety of applications including, but not limited to, intracellular sensing, immunoassays, drug screening, and immuno-analysis of tissues such as biopsy tissue, and measurements of rotational microviscosity, rolling traction, biomechanical rotations, and particle binding.

I. MagMOONs

In some embodiments, the present invention provides fluorescently labeled magnetic particles. In preferred embodiments, the particles are designed such that the signal blinks in a magnetic field. The below description provides exemplary MagMOONs and methods of generating them. One skilled in art recognizes that the particles of the present invention may be generated using any suitable method.

A. Particles

The particles of the present invention may be formulated of any suitable material. In some embodiments, probes include, but are not limited to, permanent magnetic probes that blink once per revolution, non-spherical opaque probes that blink twice per revolution, polarized probes that rotate their polarization, and magnetophoretic probes that respond to field gradients not field direction. In some embodiments, the probes are smaller than 5 µm, and more preferably, small than 1 µm. Exemplary, non-limiting probes with magnetically controllable signal intensity are described below.

i. Capped Permanent Magnet Probes

In some embodiments, permanent magnetic probes that blink once per revolution are produced by coating or capping one hemisphere of a magnetic particle with an opaque or reflective layer such as aluminum or gold.

Figure 5:
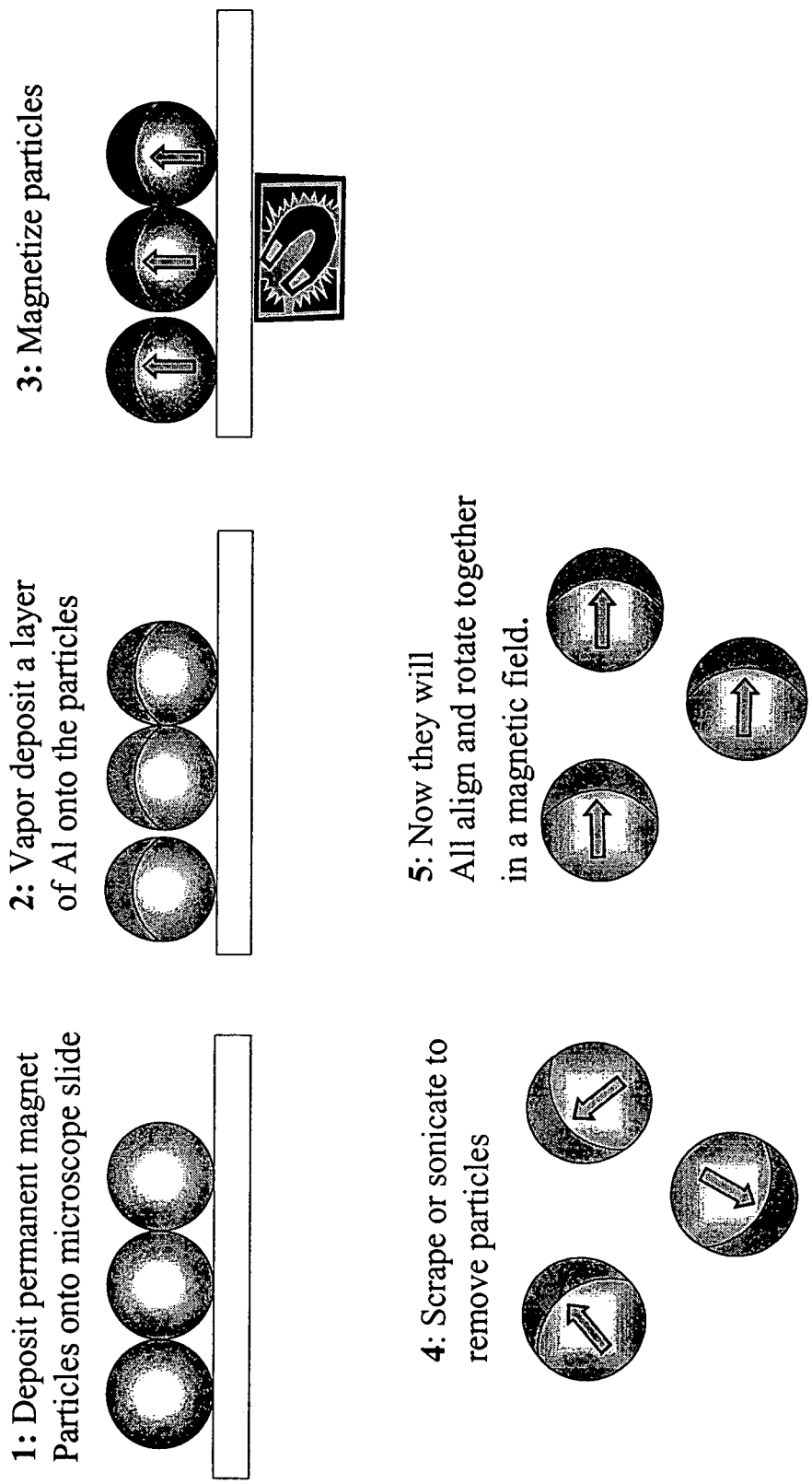
FIG. 5 shows a schematic of an illustrative process used in some embodiments of the present invention to make fluorescent magnetically aligned directionally emitting particles by attaching PEBBLES to the outside of metal-capped particles.

For example, in some embodiments, a preferentially emitting particle is generated by vapor deposit of a thin layer of aluminum onto one side of the particle (See e.g., FIG. 5). The particles described in FIG. 5 were generated by coating 4 µm polystyrene microspheres containing chromium dioxide (Spherotech) with vapor deposited aluminum and sputtered gold. The microspheres are magnetized so that their north side is uncoated. The aluminum absorbs or reflects light entering or exiting one hemisphere; the minimum thickness of aluminum that is opaque to visible light is around 20 nm. When in solution, the particles orient in an external magnetic field, and depending on their orientation, more or less light will reach the observer. By rotating the field, the particles are made to rotate, and appear to blink as the light emitting side comes in and out of view (FIG. 2).

In some embodiments, a monolayer of particles is applied to a surface (e.g., a microscope slide) and left to dry. The microscope slide is then placed in a vapor deposition chamber in vacuum, and a thin layer of metal deposited on one side of the particles. The particles are then magnetized so that the capped side lies at a fixed angle to the magnetic dipole (e.g., the coated side is the magnetic south pole of the particle). The capped magnetic particles are then removed by sonication. In some embodiments, fluorescent particles are attached to the metal-capped magnetic particles. In other embodiments, fluorescent dye is embedded inside the magnetic particle itself.

Figure 2:
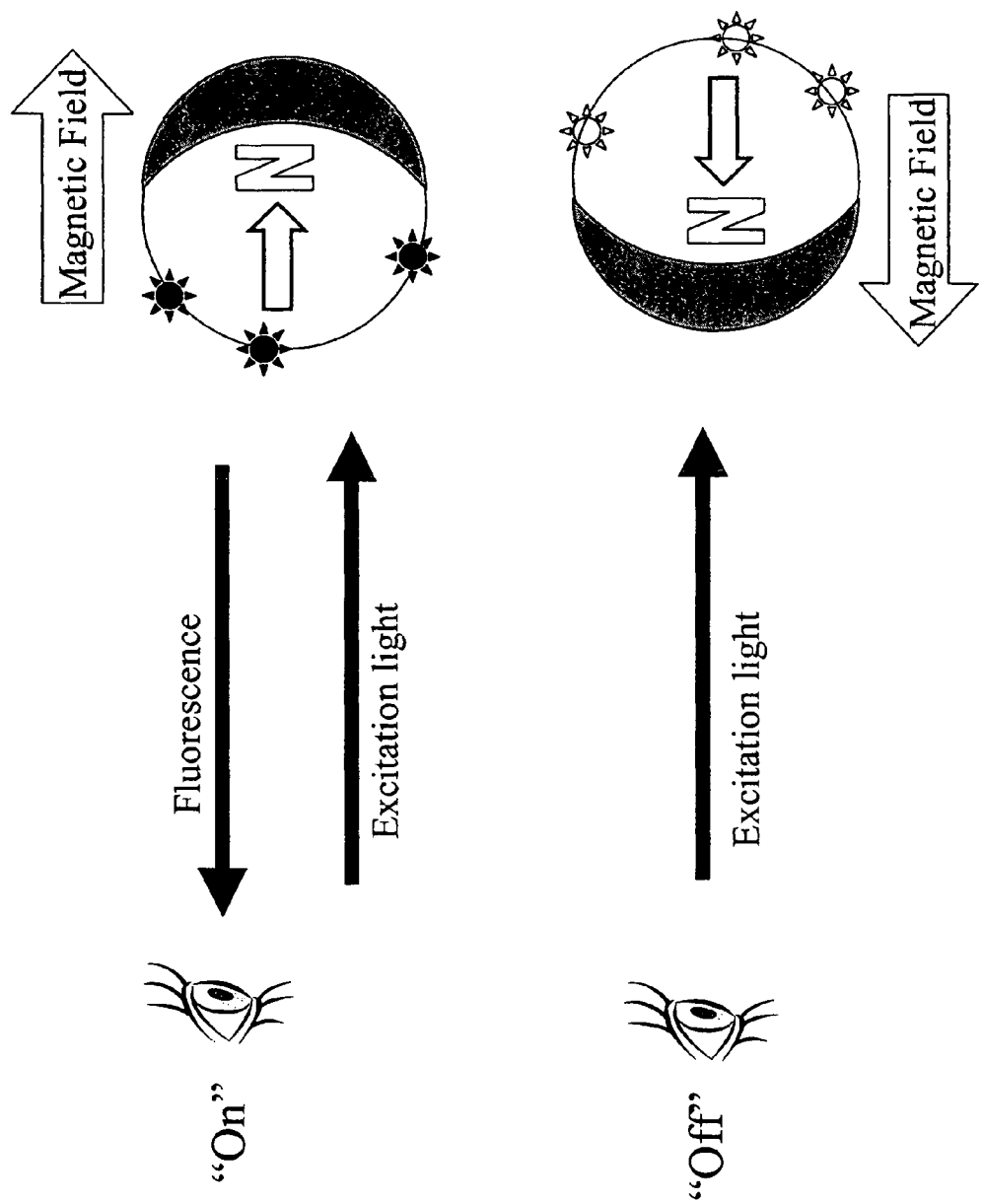
FIG. 2 shows a schematic of how metal-capped permanent magnetic particles are made to blink as they rotate in a magnetic field.
Figure 6:
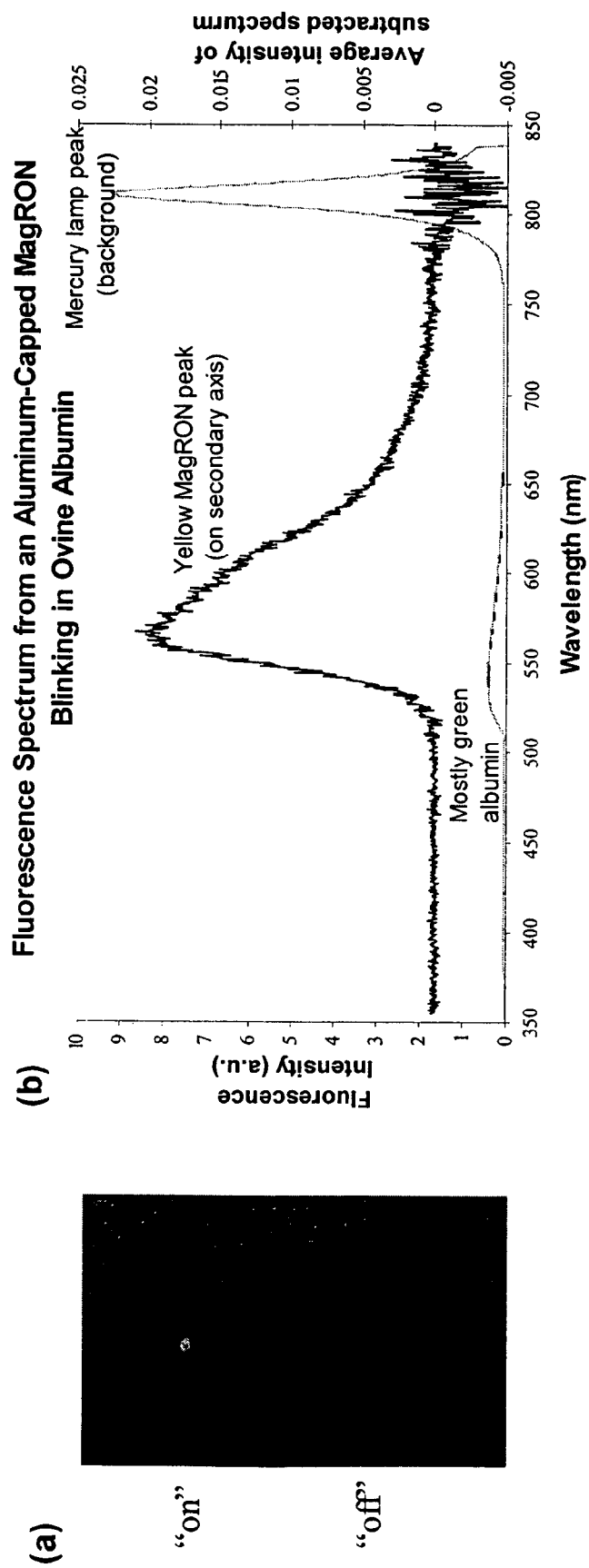
FIG. 6 shows a graph of aluminum coated MagMOON blinking in ovine albumin.

FIG. 2 demonstrates how such particles rotate and blink in a magnetic field. FIG. 3 shows fluorescence intensity time curves of aluminum capped MagMOONs rotating at two different frequencies. Experiments conducted during the course of development of the present invention (See e.g., FIGS. 6, 7, and 8) demonstrate that such particles can be detected in the presence of background fluorescence. FIGS. 6a and b illustrates how a yellow aluminum-capped MagMOON spectrum was separated from the 800 nm light leaking from the mercury lamp, and from the green fluorescence of ovine albumin. Aluminum-capped MagMOONs were dispersed in ovine albumin, a medium of similar viscosity to cellular cytoplasm, and a drop of the solution was placed on a microscope slide. A program written in labview controlled a stepper motor (through the parallel port) to rotate a magnet clockwise and anticlockwise 180 degrees, taking a spectrum after every rotation. 32 pairs of "ON" and "OFF" spectra were taken for metal capped MagMOONs, and the OFF spectra was subtracted from the ON spectra. The background mercury lamp peak decreased by a factor of ~2000 from an intensity of ~10 to +/-~0.05 (and a factor of ~5000 if spectral smoothing is used).

Figure 7:
FIG. 7 shows images from a sample with a) magnetic metal-capped probe's oriented "on," b) probes oriented "off," and c) the subtraction of "on"-"off."

FIG. 7 illustrates how images of MagMOONs can be separated from bright leaf autofluorescence. An ivy leaf was cut into thin sections with a razor. These sections were placed on a microscope slide, along with a few drops of aluminum capped MagMOON solution. A motor continuously rotated a magnet over the sample to cause the MagMOONs to blink. Blinking MagMOONs were easily distinguished from leaf fluorescence, and readily located by eye. Once a MagMOON was located, the microscope was focused onto it. The motor was then stopped, the magnet was rotated by hand to orient the particle "on." A CCD image was taken of the particle in the "on" orientation. The magnet was then rotated by hand to orient the particle "off," and another CCD image was taken. Software was used to subtract the two images in order to remove the background.

In some embodiments, a video or a series of images "on" and "off" is utilized to enhance the particle to background signal even further. For example, in some embodiments, such images of MagMOONs are used for very high contrast biopsies, or to map analytes in a cell or tissue.

Figure 8:
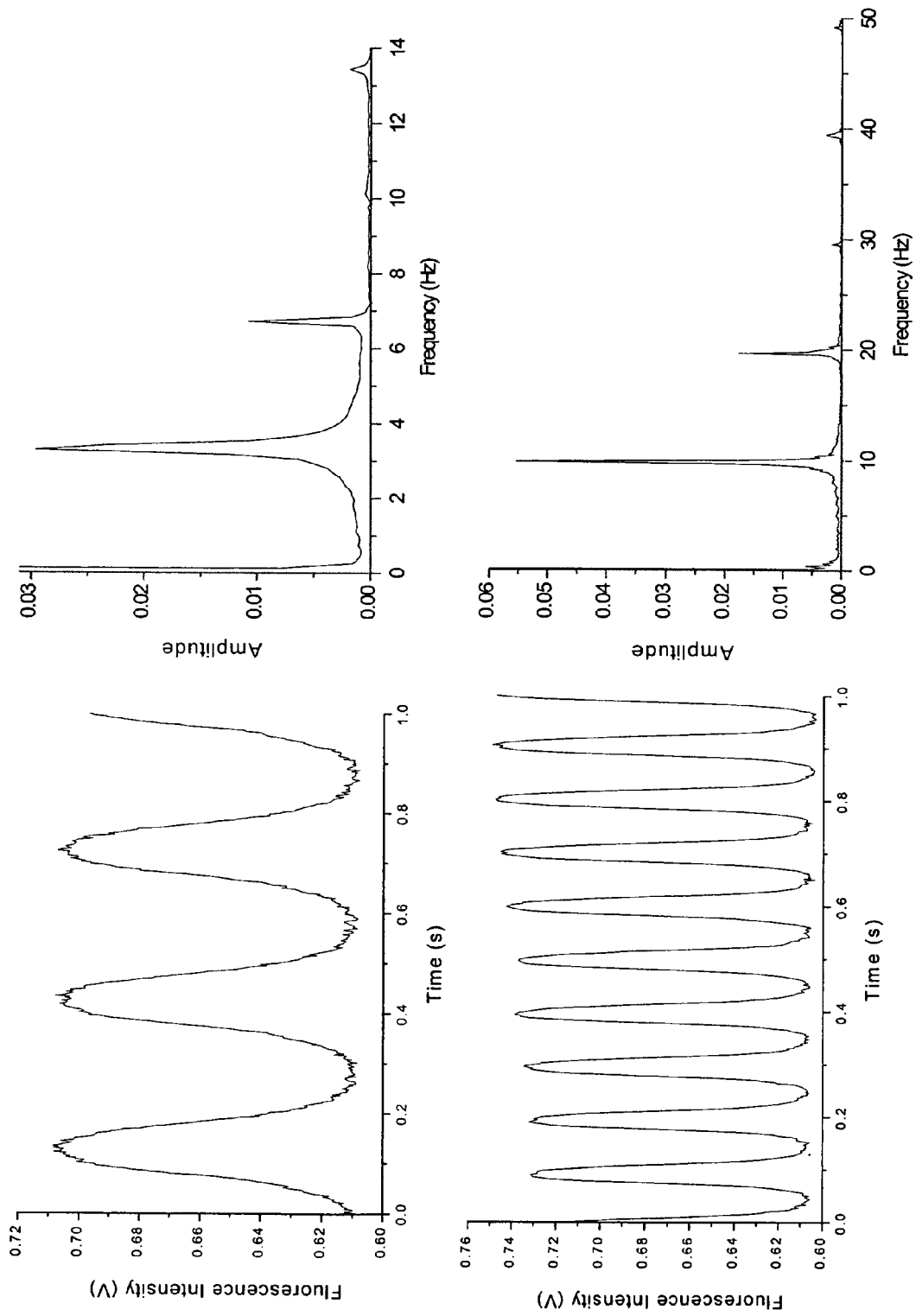
FIG. 8 shows the fluorescence intensity from a sample that contains rotating aluminum capped fluorescent permanent magnetic particles; intensity/time graph for particles rotating in a 3 Hz field; Fourier transform of intensity/time graph for particles rotating in a 3 Hz field; intensity/time graph for particles rotating in a 10 Hz field; Fourier transform of intensity/time graph for particles rotating in a 10 Hz field.

FIG. 8 shows an intensity vs. time graph for particles continuously rotated in a 10 Hz field and a Fourier transform of 10 seconds of the intensity/time curve shown. Although the blinking signal was only a tenth of the constant background signal, the signal at 10 Hz was 400 times the signal at 15 Hz (for a total enhancement of signal/background of 4000).

In other embodiments, an opaque particle with a fluorescent surface is made to emit more from one hemisphere by bleaching or quenching dyes in the other hemisphere. For example, in some embodiments, a preferentially emitting particle is generated by bleaching the particle. Particles are deposited immobilized on a flat surface, and intense ultraviolet light shines on them to bleach fluorescent molecules in or on the particle. The side under the light will be bleached more rapidly than the other side that is shadowed by the particle. Magnetic material is usually opaque, so if there is enough magnetic material, the particle is expected to be opaque.

In other embodiments, a non-magnetic particle are made magnetic by vapor depositing a magnetic material onto its surface. The procedure enables fine control over material composition and coating thickness. The half-shell particles produced are smoothly coated with controllable uniformity in amounts of magnetic material. The process is suitable for a wide range of particle sizes, shapes, and compositions, as well as for different material matrixes, providing a universal method of producing MagMOONs. Control over amount of deposited material solves the longstanding problem of creating magnetic micro and nanoparticles with uniform magnetic properties. Magnetic uniformity is especially important for single particle force and torque studies. A recent study of particles from 5 commercial companies demonstrated that the particles had variations in magnetic responsiveness varying between 30-80% from the average value (Häfeli et al., European Cells and Materials 3, 34 (2002).

Different batches of MagMOONs coated with varying amounts of magnetic material have a different maximum rotation rate, and each batch can be differentiated based on rotation rate. This signal differentiation enables simultaneous measurements from different populations of MagMOONs that sense different analytes.

In some further embodiments, vapor deposition of magnetic materials onto microspheres and nanospheres provides a method for controlling the particle geometry and the resulting properties. Experiments conducted during the course of development of the present invention demonstrated that the coercivity of polycrystalline cobalt was enhanced by the presence of polystyrene nanospheres and arch-like structures formed on the surface of the spheres during deposition. It is contemplated that the presence of these arches affects the magnetic properties of the cobalt film. Additionally, the lightning rod effect creates large electromagnetic field enhancements at the tips with applications for SERS (surface enhanced Raman spectroscopy) and for non-linear optical effects, similar to enhancements seen with prism shaped particles (Hulteen et al., J. Vac. Sci. Technol. A 13, 1553-1558 (1995)) and nanocrescents (Lu et al., Nano Lett. 5, 119 (2005). In other embodiments, MOONs are produced by continuous deposition onto a reel tape coated with microspheres.

ii. Non-Spherical Probes

In other embodiments, probes are made to differentially emit light by the generation of non-spherical probes. If a particle is opaque, and shaped like a rod or chain, it is expected to emit more light when the rod is parallel to the viewing plane than when it is perpendicular because there is more surface area exposed to light absorption. A rod shaped magnetic particle will automatically align with a strong magnetic field because of its shape; the magnetic material will make the probe somewhat opaque. Non-spherical probes have the added advantage over metal-capped probes that they can be separated from solution in strong magnetic fields without remagnetizing particles, or causing particles to aggregate. In some embodiments, probes are made more opaque by adding a strongly absorbing dye, or coating all or part of it with a thin layer of metal.

Figure 9:
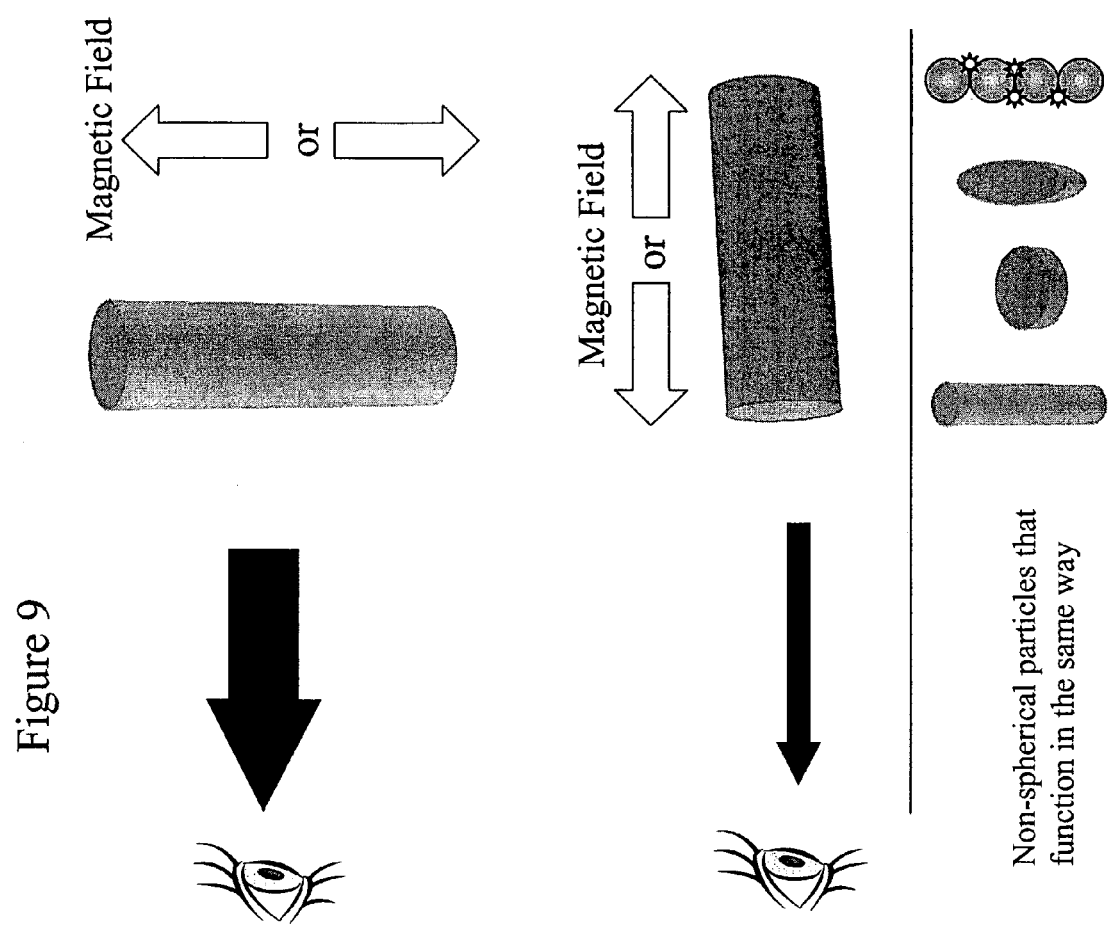
FIG. 9 shows a schematic of how opaque cylindrical particles are made to orient in a magnetic field and blink as they rotate and their surface area exposed to excitation and emission changes; inset: four different embodiments of opaque non-spherical magnetic particles.
Figure 10:
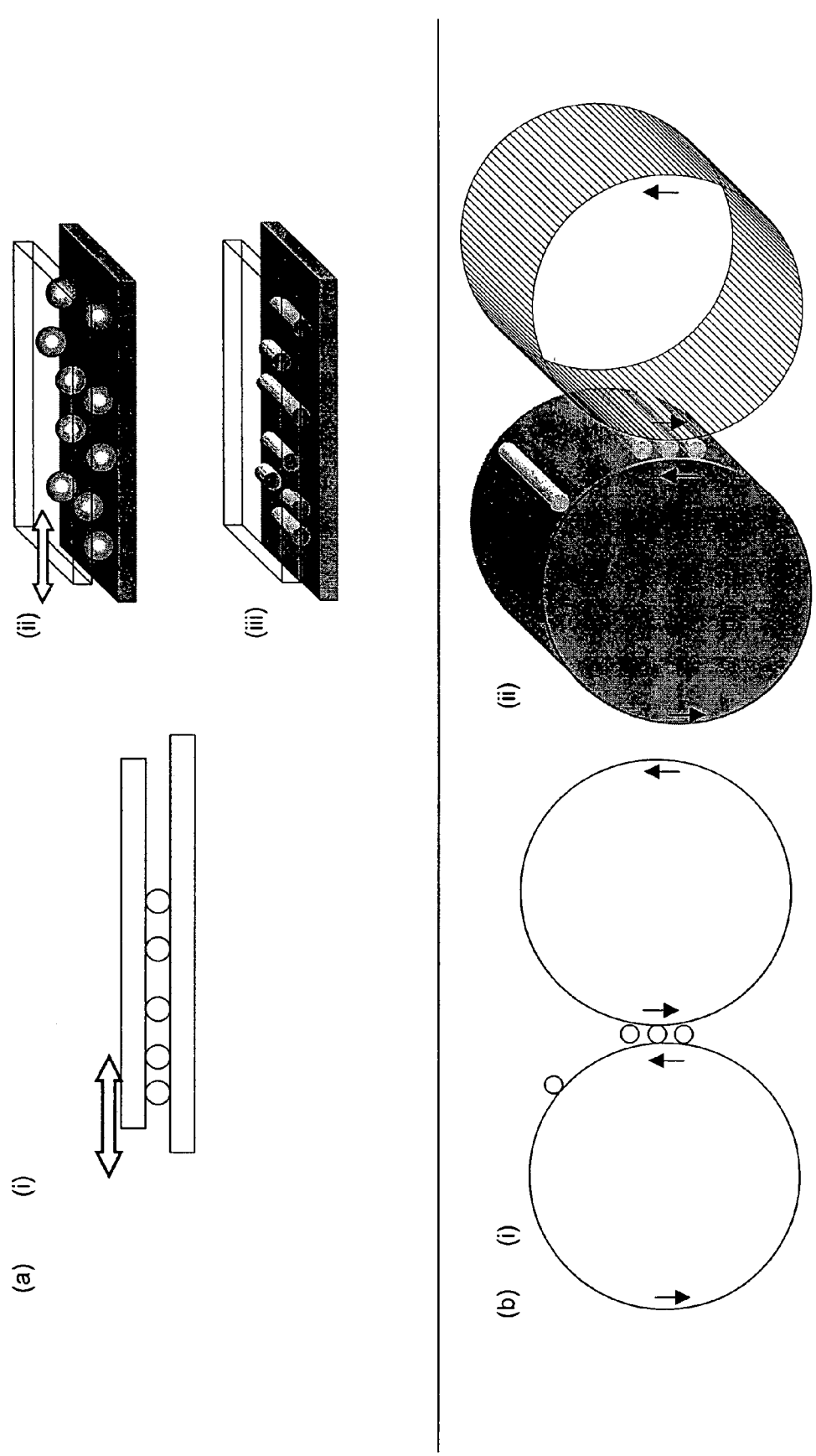
FIG. 10 shows a schematic of two illustrative methods of making cylindrical particles used in some embodiments of the present invention: a(i-iii) by rolling spherical between two flat surfaces; b(i-ii) by rolling between two counter-rotating shafts.
Figure 11:
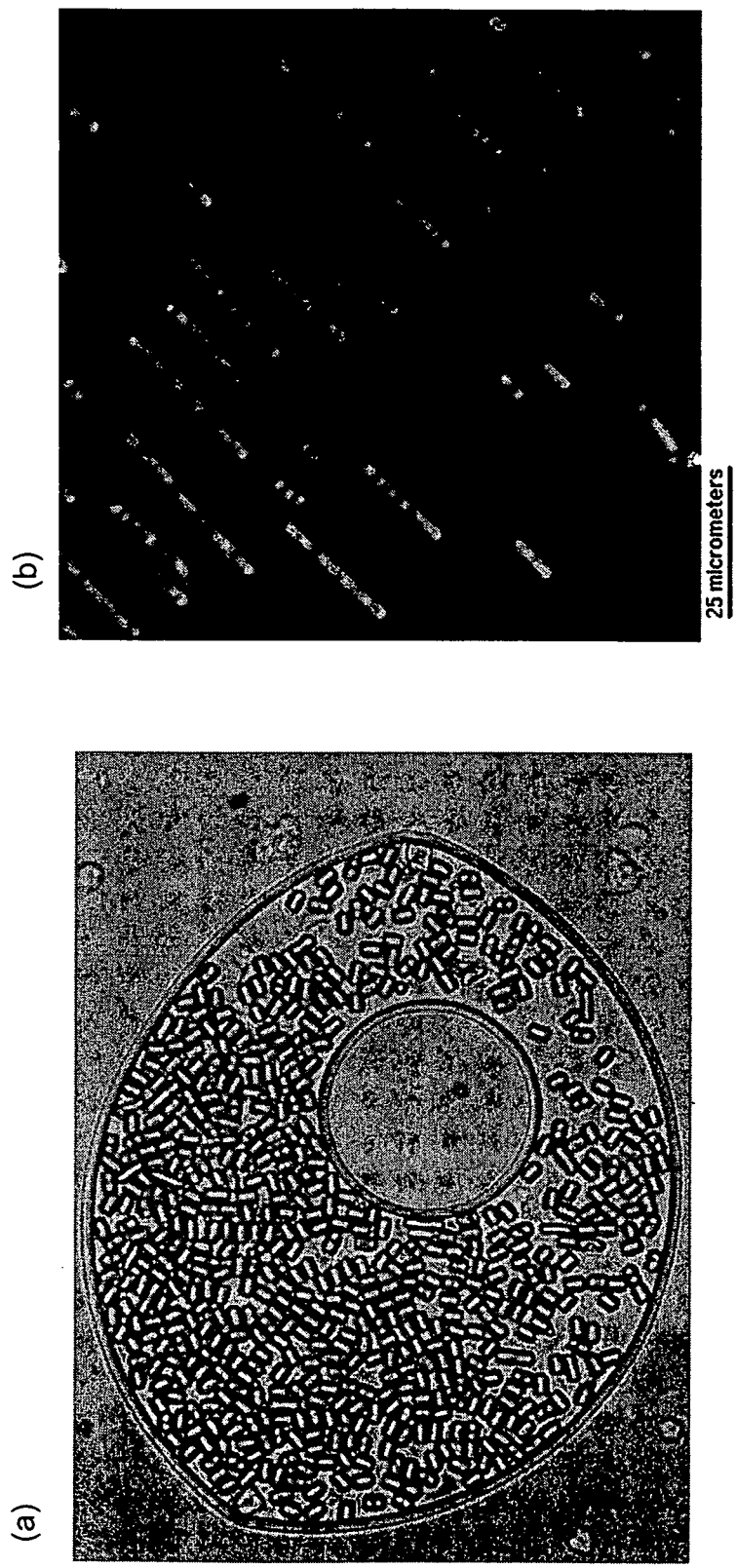
FIG. 11 shows images of particles rolled by hand between two microscope slides. (a) 3.4 µm polystyrene rolls in a droplet containing a soap bubble. (b) Multirolls of magnetic of 4 µm magnetic micropheres breaded with fluorescent decyl methacrylate nanospheres.
Figure 12:
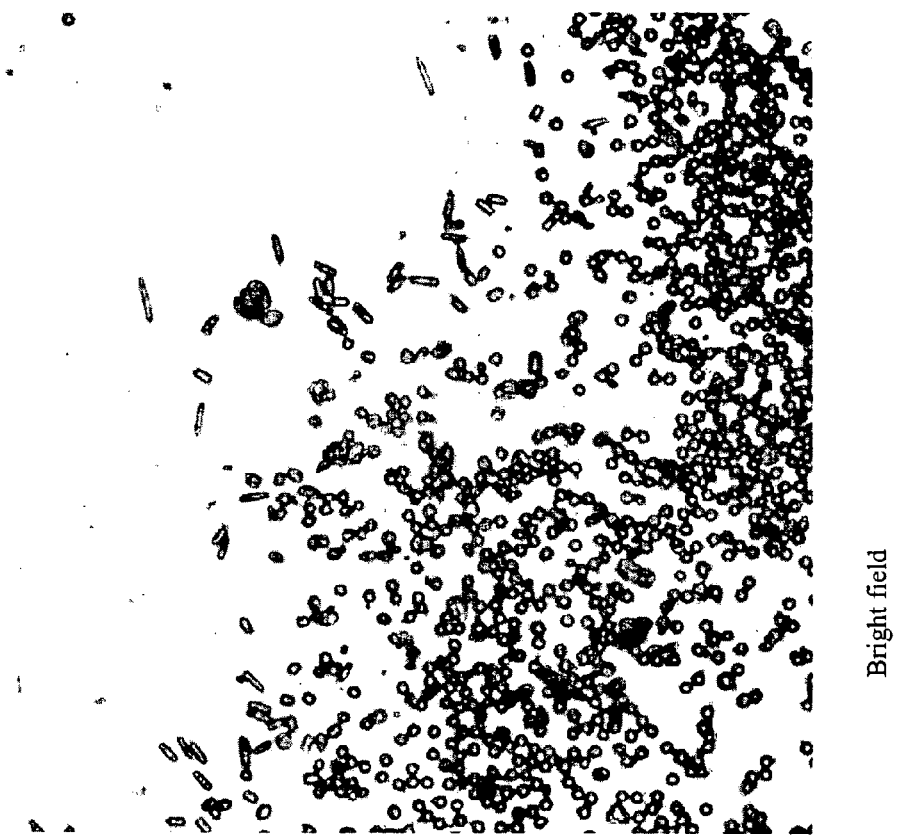
FIG. 12 shows an image of 4 µm fluorescent magnetic micropheres and cylindrical particles formed by rolling the spherical particles between two hand-held miniature electric motors; inset: fluorescent image of the same.
Figure 13:
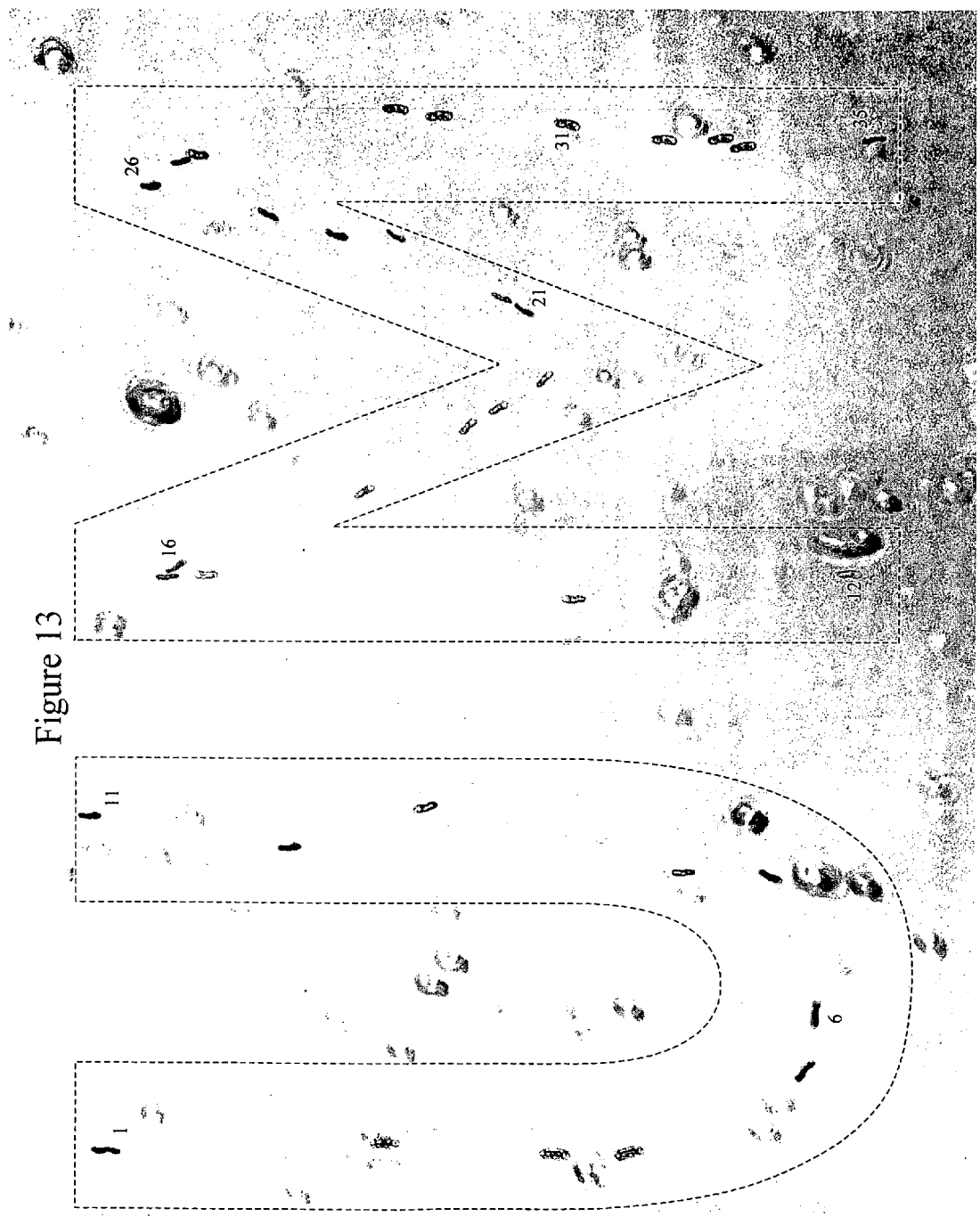
FIG. 13 shows a single magnetic roll that is positioned in a sequence of places to outline the letters UM. The particle was positioned with a 250 µm iron wire magnet that was removed from view prior to image acquisition. The particle was oriented in an external magnetic field. 35 separate images were taken of the particle in different positions and orientations, and these were overlaid in photoshop to form the image.
Figure 14:
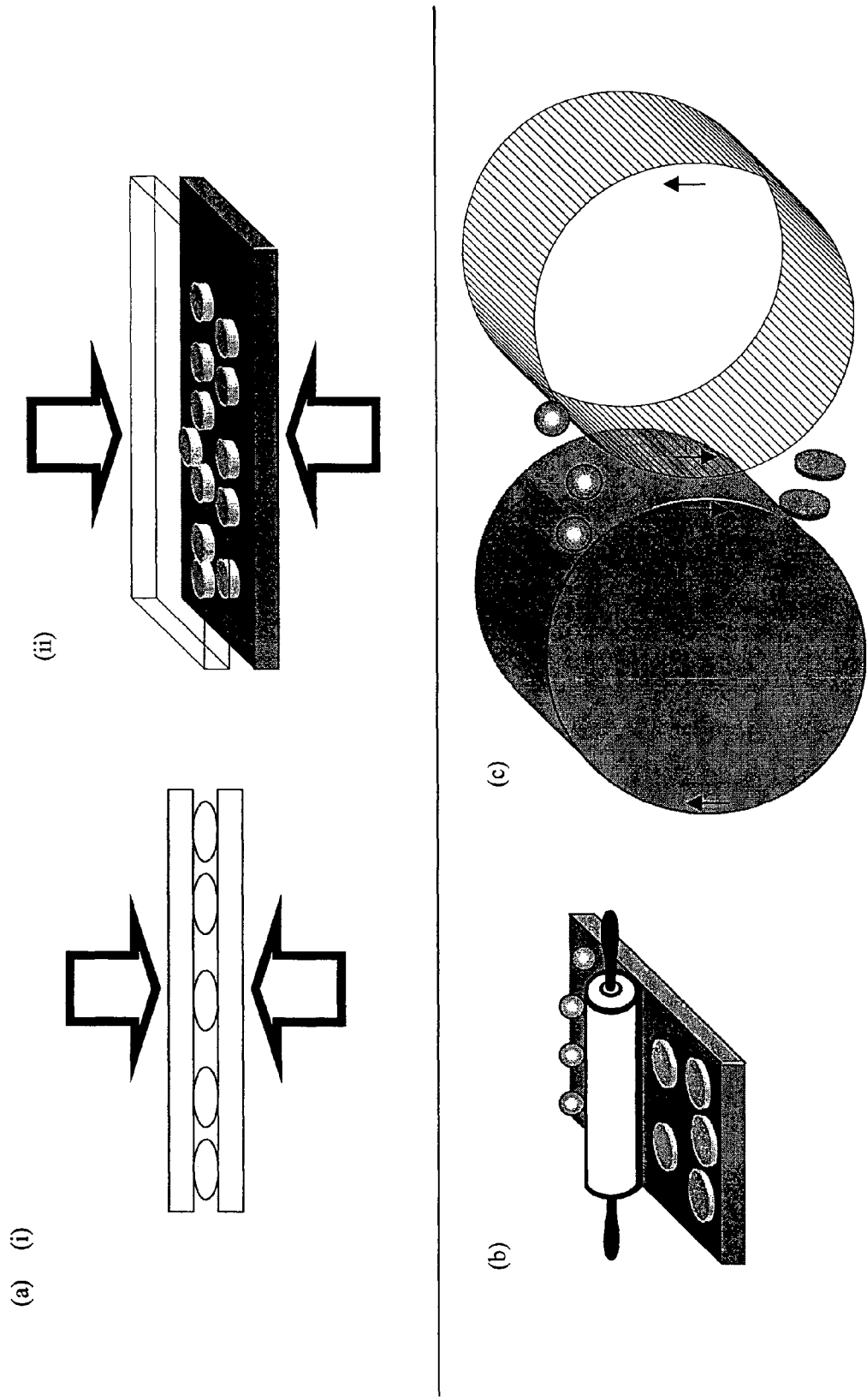
FIG. 14 shows schematics of methods of making aspherical particles utilized in some embodiments of the present invention.

There are a number of ways of making non-spherical particles. For example, in some embodiments, particles are made in non-spherical molds (Jiang et al., Science. 291:453-457). In other embodiments, particles are made by rolling between flat surfaces, or between two counter rotating cylinders (See e.g., Example 1 and FIGS. 10, 11 and 12). In still further embodiments, disk-shaped particles are made by crushing or rolling out already made particles (See e.g., Example 1 and FIG. 14). FIG. 9 shows a schematic of how non-spherical probes rotate in a magnetic field. FIG. 13 shows an image of a magnetic roll shaped particle positioned and aligned in magnetic fields.

Figure 15:
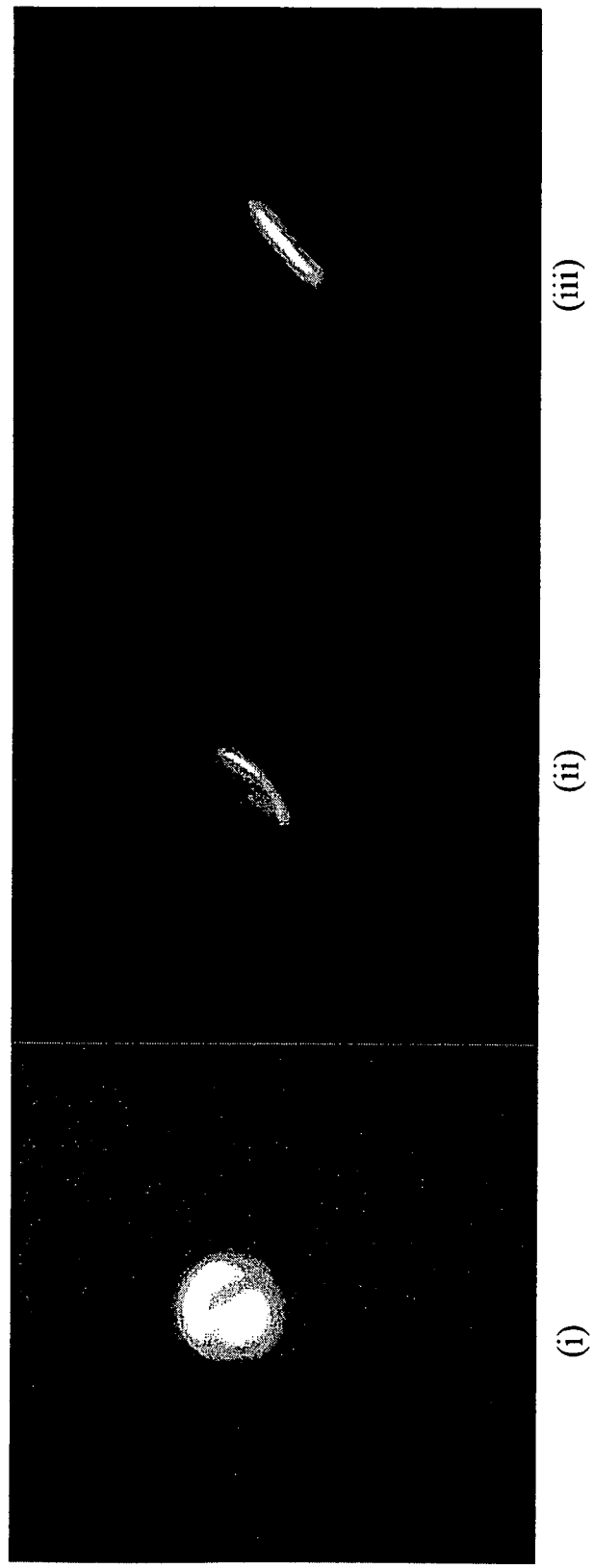
FIG. 15 shows magnetically implanted fluorescent polystyrene pancakes orienting and blinking in a rotating magnetic field.
Figure 16:
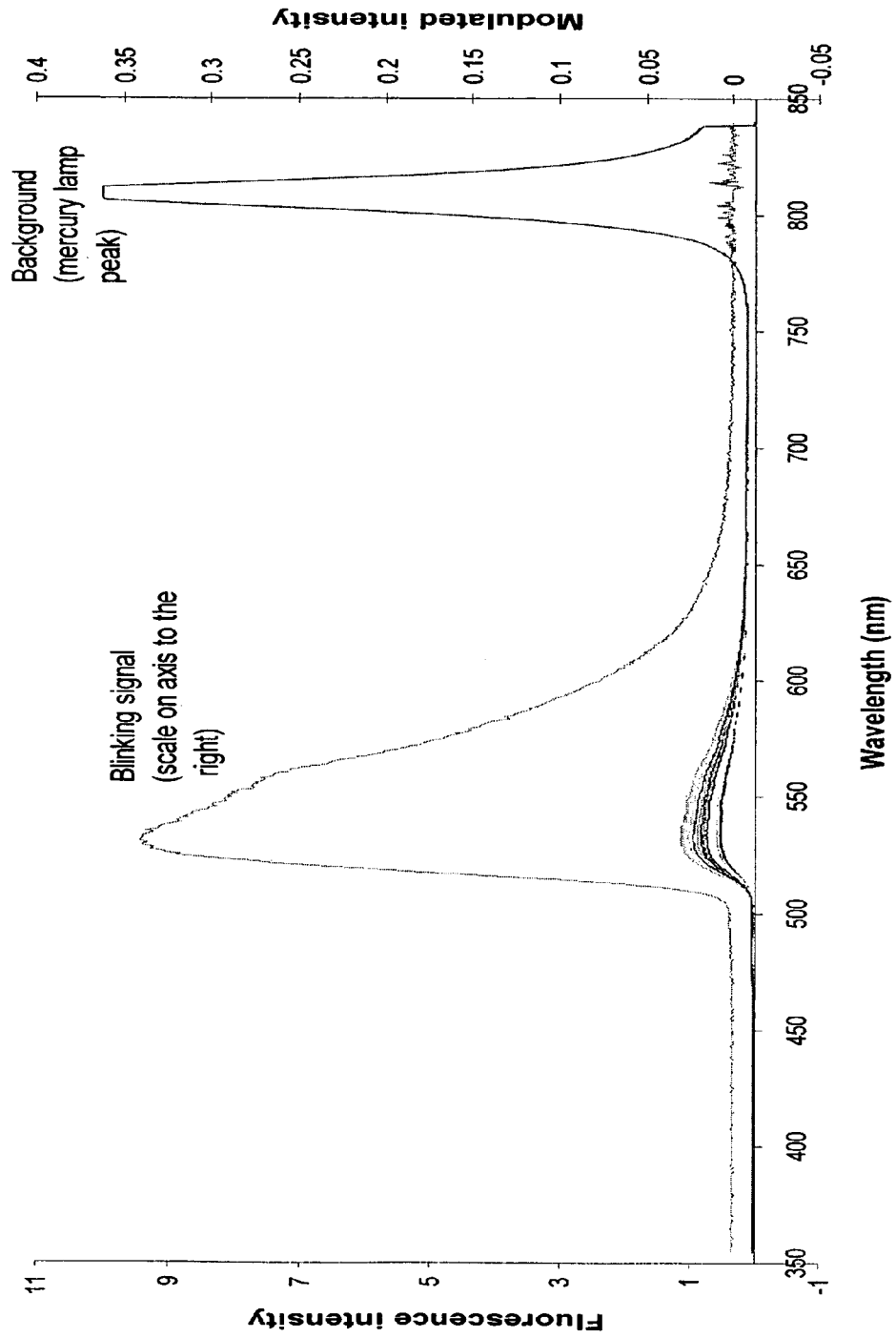
FIG. 16 shows spectra from oriented chains of particles in two different orientations, and the difference between the spectra in the two orientations.

In some embodiments, small fluorescent particles are imbedded into a magnetic particle, or alternatively, small magnetic particles are embedded into larger fluorescent particles (See e.g., Example 1 and FIG. 11b). FIG. 11b shows a fluorescence image of (formerly non-fluorescent) magnetic polymer multirolls that had been implanted with fluorescent decyl methacrylate PEBBLEs. FIG. 15 shows the rotation of a fluorescent disk shaped particle that has been embedded with small magnetic particles. FIG. 16 shows a graph of the fluorescence intensity of a blinking disk-shaped MagMOON.

iii. Chains

Figure 17:
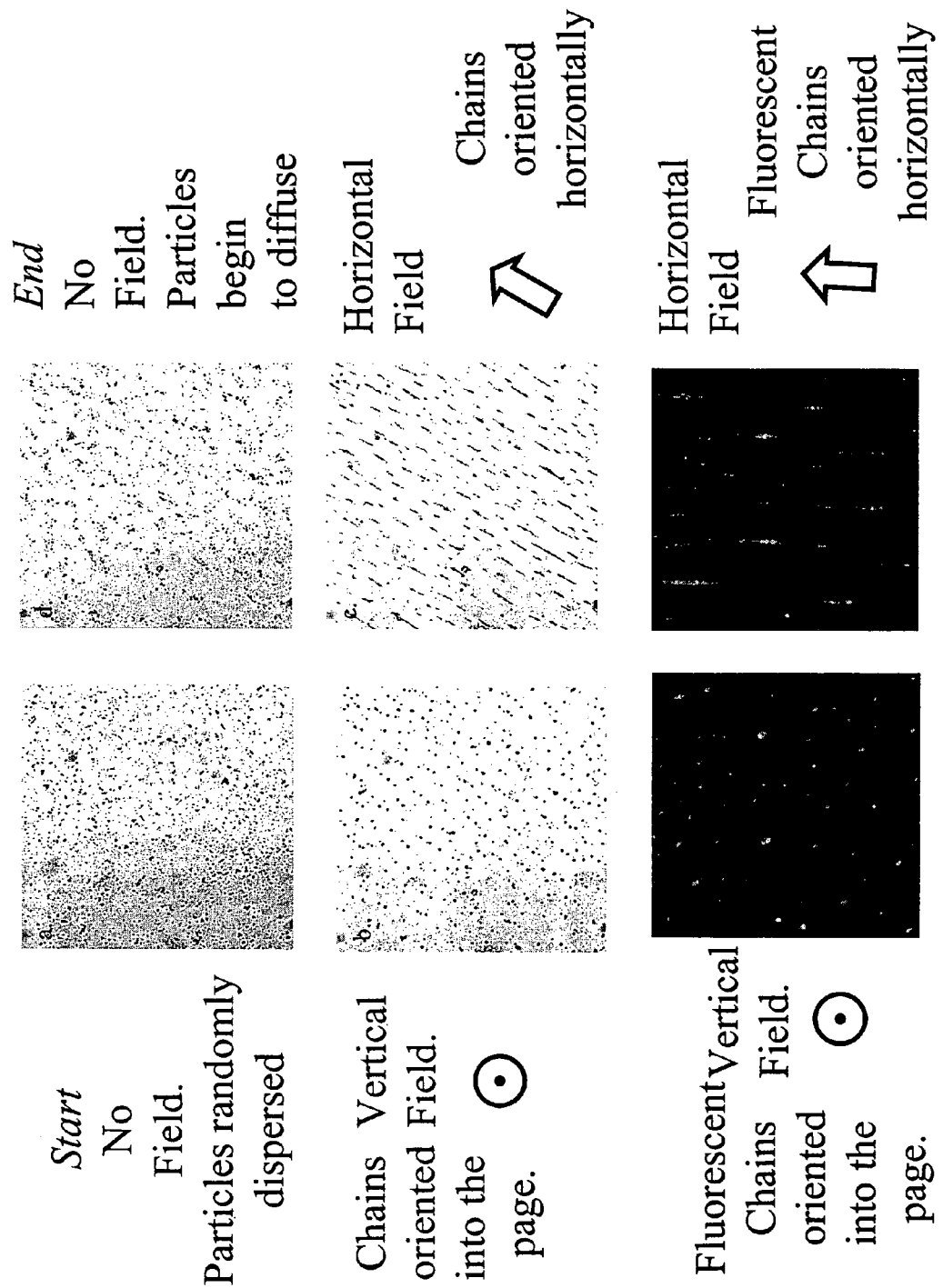
FIG. 17 shows images of superparamagnetic particles chained together and orienting in a magnetic field.
Figure 18:
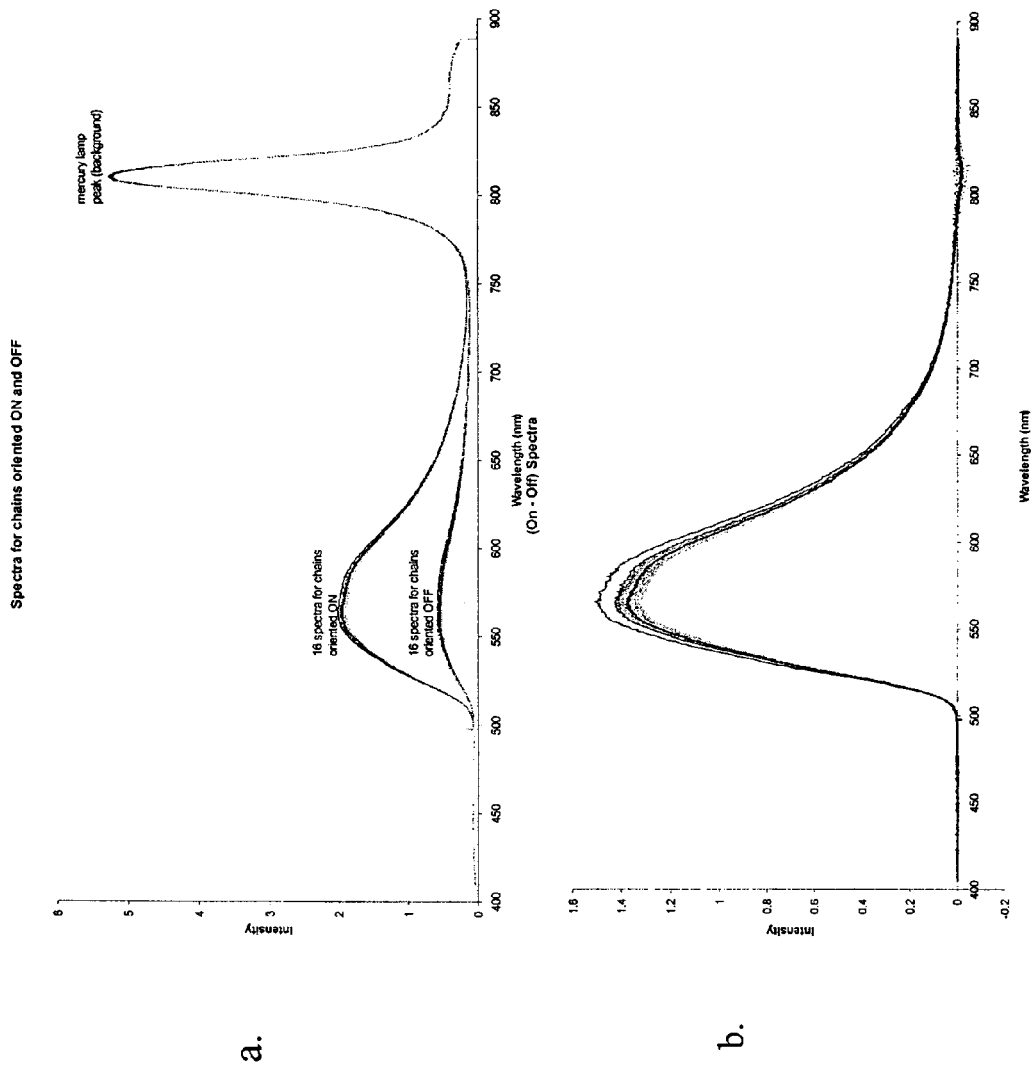
FIG. 18 shows spectra for chains oriented on and off.
Figure 19:
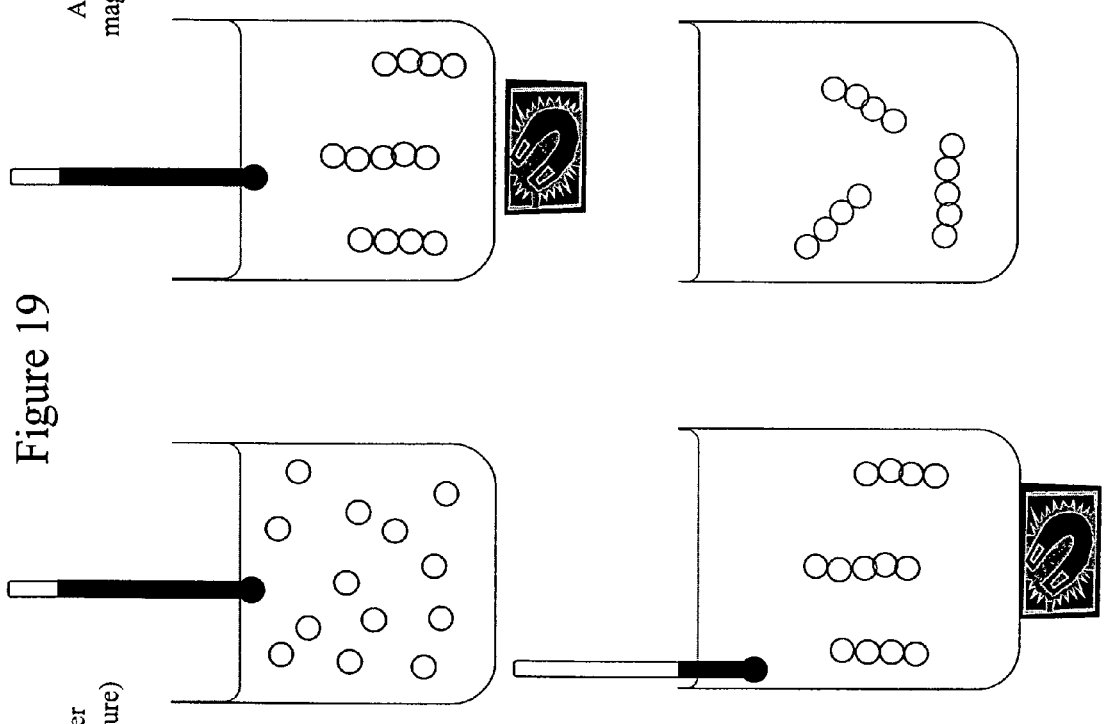
FIG. 19 shows a schematic of one method of the generation of chains of particles using hot water and a magnetic field utilized in some embodiments of the present invention.

In still further embodiments, chains of spherical MagMOONs are generated. These chains orient and blink the same way as other non-spherical probes. In some embodiments, chains of magnetic particles are spontaneously formed in a magnetic field. Such chains orient in the direction of the magnetic field (See e.g., FIG. 17). FIG. 18 shows spectra of chains oriented in two different directions. In other embodiments, permanently linked chains are generated by heating to above the glass transition state, applying a magnetic field, and then cooling (See e.g., FIG. 19).

In other embodiments, the chains are linked together only in the presence of chemical analyte, and the concentration of chains formed indicates the amount of analyte present. The amount of chain present is determined by any suitable method including, but not limited to, by measuring magnetically modulated fluorescence, transmission, or reflection.

iv. Polarized Probes

Figure 20:
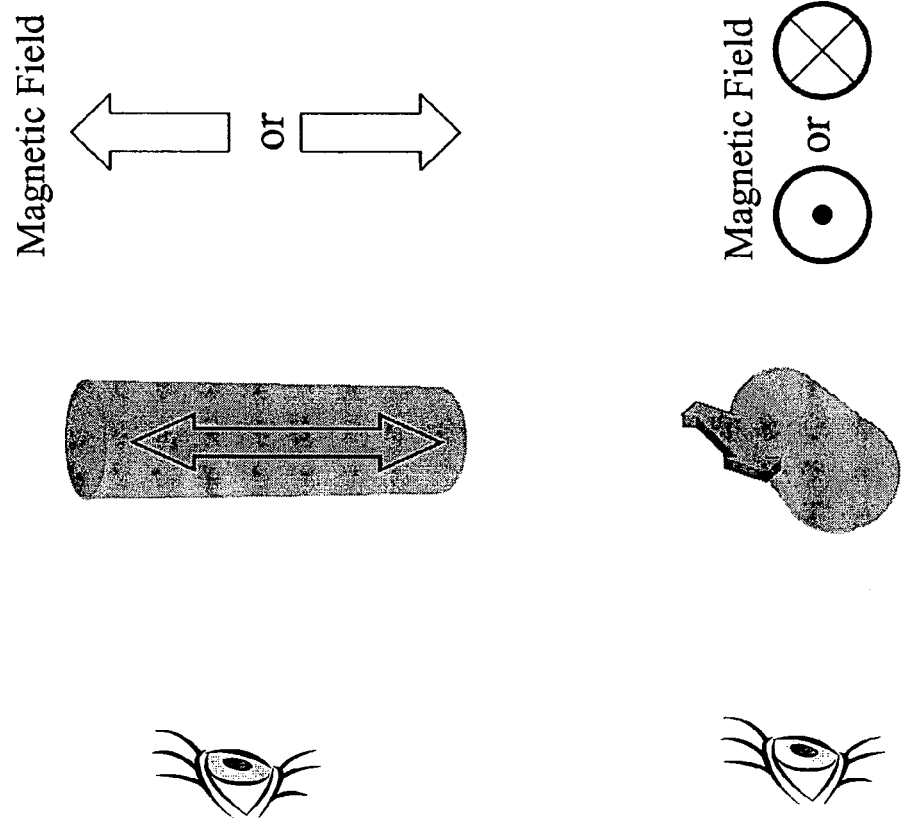
FIG. 20 illustrates how polarized particles are made to orient in a magnetic field and rotate the polarization of their fluorescence as they rotate.

In still further embodiments, polarized probes are made to rotate in a plane parallel to the polarization plane. The fluorescence in each polarization is separated using a polarizing prism, or the light in one polarization is examined by using a polarizer to filter out the other polarization. FIG. 20 shows how polarized probes are modulated in a magnetic field. None of other particles described above should change their fluorescence intensities if they rotate in this plane, unless they also happen to have polarized fluorescence.

Polarized probes can be formed in a number of ways. For example, in some embodiments, one polarization is bleached out. If the dye molecules are fixed inside the probe, then the unbleached dyes will not be able to reorient, and probes will retain a permanent polarization. Particles that are bleached retain their polarization for at least days after the bleaching. If the dyes are free to rotate, then the probe will not retain a permanent polarization, but if fixed particles can be polarized and added to the probe, then their polarized emission can be used to excite dyes that are free to rotate.

In other embodiments, polarized probes are formed by aligning dyes in the polymer by rolling. In yet other embodiments, polarized probes are generated by aligning polymer chains by rolling and then absorbing iodine that will orient with the chains and preferentially absorb one polarization. For example, in some embodiments, optical polarizing materials are made by aligning polymer chains by stretching the polymer film, and then adsorbing iodine onto the chains to orient and absorb light of one polarization. In still further embodiments, polarized probes are formed by coating a metal onto cylindrical particles with diameters less than the wavelength of light.

v. Gradient Sensitive Probe Molecules

Figure 24:
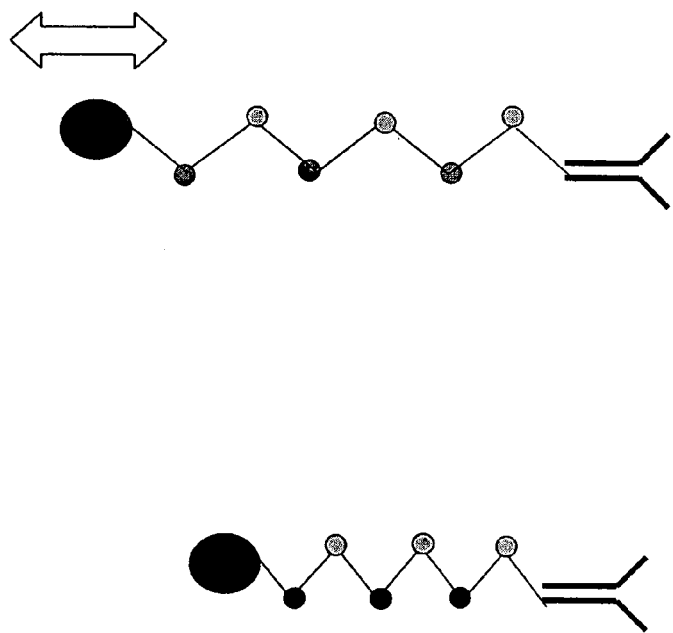
FIG. 24 shows a schematic of gradient sensitive probe molecules utilized in some embodiments of the present invention.
Figure 25:
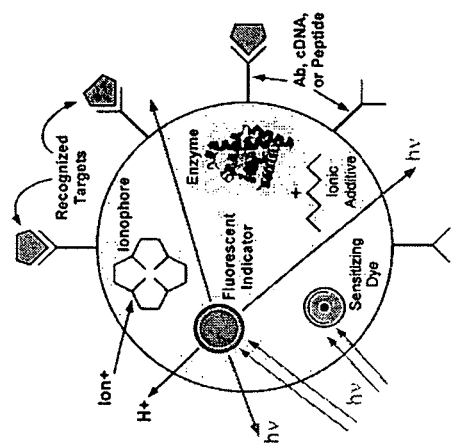
FIG. 25 shows a schematic PEBBLEs with multiple sensing functionalities utilized in some embodiments of the present invention.

In yet other embodiments, the present invention provides gradient sensitive probe molecules (See e.g., FIG. 24). Gradient sensitive MagMOONs respond to magnetic field gradients as opposed to orientations. In one embodiment, oscillating magnetic fields pull magnetic particles from side to side, and one measures the fluorescence intensity in every pixel of a digitized image. As the particles move back and forth, the fluorescence signal changes in every pixel through which the particle travels. If a particle is in one pixel during one image and another pixel in another image, the difference between the two images will be a positive value where the particle started and a negative value where the particle ended; any constant background will be subtracted out. By taking the absolute value, of the pixel variation, the particles that move are highlighted. If the particle retraces its steps in an oscillating field, then the signal from the particles can be amplified over particles that move randomly. In other embodiments, a continuous reading of particle fluorescence at any point is frequency filtered to find particles oscillating at the magnetic field frequency.

In another embodiment, FIG. 24 shows a MagMOON that blinks in an oscillating field gradient, but only if it is bound to a surface with an antibody bond. For example, in some embodiments, a flexible molecule (e.g., DNA) is labeled with donor (D) and acceptor (A) molecules. The molecule is then anchored (e.g., with an antibody). When D and A are close together, fluorescence resonance energy transfer (FRET) occurs. The molecule is pre-stretched with a magnetic field gradient so that the spectrum due to FRET is maximally sensitive to small changes in molecule tension. A small oscillating magnetic field gradient then causes the FRET signal to oscillate. The spectrum due to FRET modulates as the particles are stretched and compressed (or twisted and untwisted).

vi. Labeling Particles

In some embodiments of the present invention, labels (e.g., fluorescent indicator dyes) are incorporated into the MagMOON itself. In other embodiments, the above-described MagMOONs are modified by the attachment of labeling particles (e.g., PEBBLES, See e.g., U.S. Pat. No. 6,143,558, herein incorporated by reference). In such embodiments, the label comes from labeling particles attached to, or embedded in, a MagMOON. Such a hybrid allows the advantages of sensing and detecting, while simplifying the production of the magnetically responsive optically modulated component of the MagMOON.

B. Labels

The MagMOONs of the present invention further comprise a label for their detection. In some embodiments, the label is an indicator dye. The present invention is not limited to a particular fluorescent dye. Any dye that fluoresces, including those that fluoresce in the UV and IR ranges of the spectrum, is contemplated by the present invention. Commercial sources for dyes include, but are not limited to, Molecular Probes (Eugene, Oreg.), Sigma/Aldrich (St. Louis, Mo.), Alfa Aesar (Ward Hill, Mass.), and Exciton (Dayton, Ohio).

In some embodiments, multiple dyes are used to generate ratiometric indicator dyes, which have two spectral peaks where the ratio of the two peak intensities depends on the chemical environment. For example, in some embodiments, one dye is responsive to the chemical concentration to be sensed, and the other emits a constant signal.

A dye of interest is chosen that is sensitive to the analyte of interest. Dye properties such as excitation and emission spectral overlap with other dyes in the MagMOON, dynamic range, selectivity, photostability, quantum efficiency and cost are compared to find dyes best suited to the application. PEBBLEs enable use of dyes that would otherwise be toxic to cells, prevent interference from cellular proteins, and enable synergistic sensing mechanisms such as enzyme oxidation and ion correlation. MagMOONs further allow for the use of dyes that excite in the ultraviolet (where most dyes will excite, but autofluorescence is particularly problematic), and dyes with low quantum efficiency. In addition, spectral overlap is less of a concern because of multiplexing between distinguishable MagMOONs, and because a wider range of excitation wavelengths can be used The present invention is not limited to fluorescent labels. Any label that allows for the detection of particles oriented and moving in a magnetic field may be utilized. In other embodiments (e.g., RAMAN spectroscopy), the label is metal nanoparticles on the surface of the MagMOON. In other embodiments, metal coated MagMOONs are visualized using the methods of the present invention.

C. Nanobottles

In some embodiments, probes are encapsulated into nanobottles. A selectively porous polymer or lipid shell may be formed around any of the above particle types. Preferred shells for encapsulation are those that allow the particles to spin with a maximum rate dependent on the viscosity inside the shell, and independent of the environment outside the shell. In some embodiments, the shell is immobilized in a highly viscous environment, or attached to a rigid structure with antibodies, without preventing the internal particle from rotating in its compartment. It is preferable that the polymer shell be permeable to chemical species of interest, but impermeable to large proteins that may change the viscosity in the compartment. The nanobottles of the present invention are particularly useful for detecting small intracellular molecules.

In some embodiments, the shell is a liposome. Liposomes form spontaneously when a lipid is hydrated in the presence of water, and if magnetic particles are present, then some of the lipids may form containing the particle. Liposomes can be easily modified to become porous. Alternatively, in other embodiments, shells are formed by coating a polymer (e.g., polystyrene) around an intermediary layer and dissolving the intermediary layer. In still further embodiments, magnetic particles are formed inside porous shell by precipitating iron oxide inside the shells. In yet other embodiments, the nanobottle comprises a sol-gel.

Figure 21:
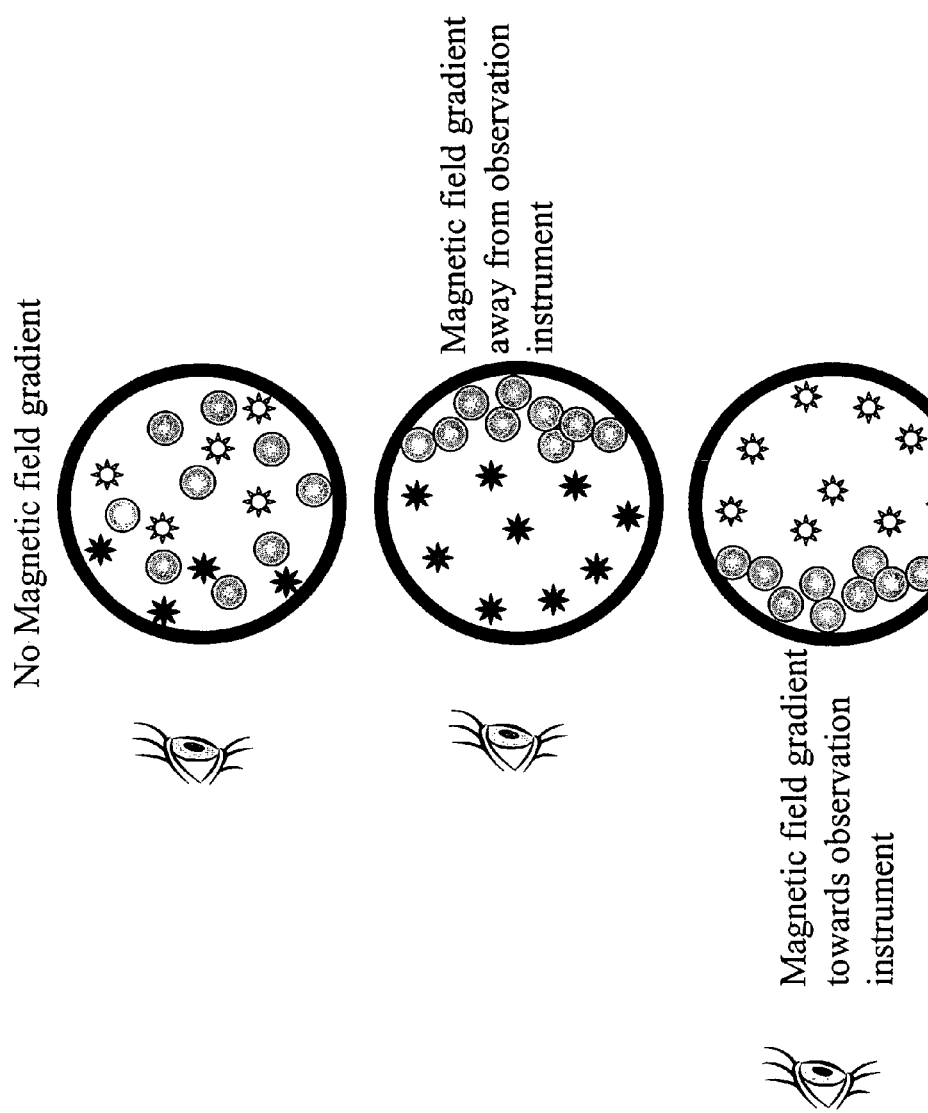
FIG. 21 shows a schematic of nanobottle-encapsulated magnetophoretic probes made to blink in response to field gradients not field direction utilized in some embodiments of the present invention.
Figure 22:
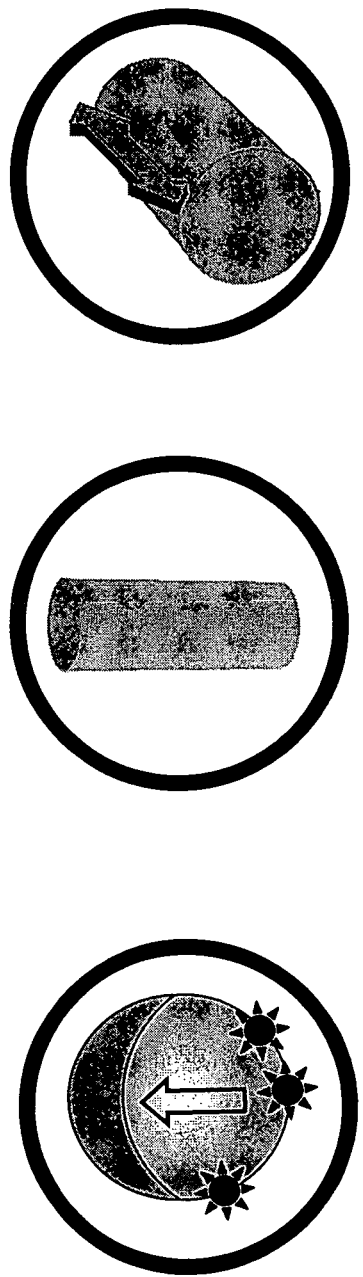
FIG. 22 shows a schematic of probes encapsulated in a nanobottle with controllable internal viscosity utilized in some embodiments of the present invention.

By varying the viscosity inside the compartment, particles are made with low viscosity that can spin rapidly in response to a rapidly rotating magnetic field (or oscillating field gradient), and particles with high viscosity compartments that respond only to more slowly changing fields (unless the viscosity outside is lower than inside and the whole nanobottle spins). Only the low viscosity particles can blink at high frequencies, whereas all particles can blink if the field changes slowly enough. Therefore, low and high viscosity particles are distinguished based on the maximum frequency that they will respond to for a given field strength. FIGS. 21 and 22 show schematics of modulated MagMOONs inside nanobottles.

In some embodiments, antibodies are attached to the outside of nanobottles, thus allowing targeting of the nanobottle to a specific cell, where the chemical sensor serves as a label (See e.g., FIG. 23). In other embodiments, oscillating magnetic filed gradients cause opaque magnetic particles within a nanobottle to move from one side of the capsule to the other, thereby masking and unmasking dye trapped within the particle, and causing the particle to blink (see FIG. 21).

D. Rotation of Particles

The present invention further provides methods for rotating the MagMOONs described above. Magnetic fields can cause particles to move in two ways. Magnetic particles translate to areas of highest magnetic field if placed in a magnetic field gradient. Magnetic particles will also orient to align with a magnetic field direction. Both translation and rotation can be used to modulate the signal from properly made probes. Magnetic particles that orient in a magnetic field will rotate in a rotating magnetic field. However, their maximum rate of rotation is limited by viscous drag. This drag depends on the viscosity of the sample and on the particles' shapes (Valberg and Butler, Biophysical Journal. 1987 October; 52(4):537-550). Magnetic particles can be rotated very rapidly in water, and still at a reasonable rate in many biological fluids. In vivo experiments in human lungs confirm this.

Magnetic particles will experience a force towards regions of high magnetic field strength. This force is proportional the gradient of the magnetic field at the location of the particle, and the volume of magnetic material in the particle. How rapidly the particle moves in response to the force depends on how large the force is, the hydrodynamic radius of the particle, and the viscosity of the environment. Field gradients have successfully been used to guide magnetic particles to the tail vein of a rat, and to move micron sized particles inside single cells. It is possible to adjust the magnetic field gradient in a region without significantly affecting the field direction.

A rotating magnetic field causes the probes to rotate. In some embodiments, rotating fields are generated by fixing a permanent magnet to a motor that spins when the motor is on. By increasing the rate of rotation of the motor, the particles rotate faster. In other embodiments, rotating fields are generated by two or three perpendicular solenoids fed by alternating electric fields out of phase. The rate of particle rotation adjusted by changing the frequency of the current in the solenoids. It is not necessary that the magnetic field rotate at a constant rate or in a constant direction. In some embodiments, where particles that can only rotate a small angle are utilized, small angles of magnetic field rotation increase signal to noise for the particles. In other embodiments, the rotation direction is changed periodically to avoid particles from translating and rolling on surfaces.

In some embodiments, particles for sensing multiple chemicals on different sensing particles are designed for independent sensing by designing chemical sensors that blinks at a different frequency or phase, or if one type of sensor is optically polarized while others are directionally emitting, or one type responds to field gradients while others respond to field orientations.

E. Brownian MOONs

MagMOONs experience two forces in a solution, a magnetic force used to orient the particle, and thermal forces trying to turn the particles in random orientations. In one preferred embodiment, the magnetic force is much larger than the thermal force, and the particle orientation is rigidly controlled by the magnetic field (in a strong field, very little magnetic material is required to make this true). However, as the magnetic field is weakened, and the amount of magnetic material in the particles decreases, the random Brownian force becomes more and more significant. In the limit of no external magnetic field, or no magnetic material, the particles are modulated solely by the Brownian rotation, and become "Brownian MOONs."

Brownian MOONs are suitable for use in applications similar to MagMOONs. The erratic blinking allows the probe signal to be separated from background, similar to magnetic modulation, only not requiring magnetic fields or magnetic material in the particle. In addition, the rate of the signal fluctuation is a simple and direct measure of local rotational viscosity, a fundamental property of materials. Measuring local rotational viscosity yields insights into materials research, cell function, and cell viability. It is extremely difficult to measure local rotational viscosities on these microscopic scales using any other method.

In some embodiments, metal-capped MagMOONs are magnetized through the equator of the half-shell rather than through the poles. When the MagMOON is oriented in an external magnetic field, the particle is free to rotate around the axis of the magnetic field as long as its moment remains parallel to the external magnetic field. Tracking its orientation around this axis reveals torques acting on the particle from Brownian fluctuations, fluid vorticity, gravitation, and other torques experienced by Brownian MOONs. The magnetic field forces the particle to rotate only around a single axis.

F. Production of MagMOONs

In some embodiments, MagMOONs are generated using a vapor deposition method. In some embodiments, MagMOONs are produced by coating a uniform half-shell of magnetic material (e.g., ferromagnetic cobalt) onto nanospheres and microspheres using ultra high vacuum (UHV) vapor deposition.

The use of top down deposition of magnetic materials solves the longstanding problem of non-uniformity in commercially made magnetic particles (usually produced using purely bottom up chemical synthesis). The control over material composition also increases the effective magnetic moment of the particles compared to iron oxide, and allows control over coercivity, With uniform magnetic particles, more accurate experiments can designed, so as to better probe microrheology and molecular interactions. Additionally, this fabrication technique finds use in the modification of solid state sensors into MagMOONs, by the simple step of depositing a ferromagnetic metal onto the surface of a sensor.

II. Uses of MagMOONs and Brownian MOONs

The Mag and Brownian MOONs of the present invention find use in a variety of applications requiring the detection of cellular analytes and large molecules in cells and tissues. The below description provides several non-limiting examples of applications.

A. Detection of Intracellular Analytes

In some embodiments, the present invention provides methods of detecting intracellular analytes and biological molecules. Fluorescence provides a highly sensitive way to detect the environment around molecules. Fluorescence is used in intracellular ion sensing, immunoassay studies, biopsies, single molecule studies, and other studies of importance to fundamental chemistry, cell research, pathogen function, and drug response. The use of MagMOONs or Brownian MOONs in such applications provides an increase, by orders of magnitude, of signal/noise. It also enables more dyes to be used in a wider range of samples, allow more dyes to be used simultaneously, and allows the detection of more analytes more rapidly in more situations. The methods of the present invention provide sensitivity similar to chemiluminescence and bioluminescence except much brighter, and thus more rapid and cheaper.

The present invention is not limited to the detection of a particular analyte. For example, to elucidate how cells respond to external stimuli, one can make MagMOONs or Brownian MOONs containing fluorescent indicator dyes that are sensitive to ions or oxygen concentrations. Exemplary small molecule intracellular analytes and suitable indicator dyes include, but are not limited to, those described in U.S. Pat. No. 6,143,558, herein incorporated by reference. The present invention is also not limited to a particular method of administering MagMOONs or Brownian MOONs to cells. In some embodiments, microinjection, gene gun, liposome delivery techniques, and magnetic transduction (See e.g., U.S. Pat. No. 5,516,670, herein incorporated by reference) are utilized.

In some embodiments, several analytes are detected through the sequential use of MagMOONs or Brownian MOONs containing different dyes. In some embodiments, due to the sensitive nature of detection utilizing MagMOONS or Brownian MOONs, dyes with low quantum efficiency, as well as UV and IR excited dyes are utilized. The methods of the present invention are suitable for use in a variety of samples, including, but not limited to, cells and tissues. The background minimization obtained with the use of Mag or Brownian MOONs allows for simple sample preparation, with limited purification and washing of samples required. In some embodiments, ratiometric detection is utilized (See e.g., Example 2 and FIGS. 28-29).

In some embodiments, multiplexed assays are utilized. Background elimination allows a wider range of dyes to be used, allowing more analytes to be detected simultaneously. In some embodiments, due to the increased signal/noise obtained with the methods of the present invention, dyes with overlapping peaks are used for multiplexing. In some further embodiments, more multiplexing is achieved by using both MagMOONs that blink once and twice per revolution. In additional embodiments, additional multiplexing is achieved by looking at individual color coded MagMOONS (e.g., Red: Green:Yellow ratio can indicate which type of MagMOON observed). Instead of looking at different chemicals simultaneously, one can use different dyes for the same chemical to extend the dynamic range, or increase selectivity by accounting for non-selective interactions.

Figure 26:
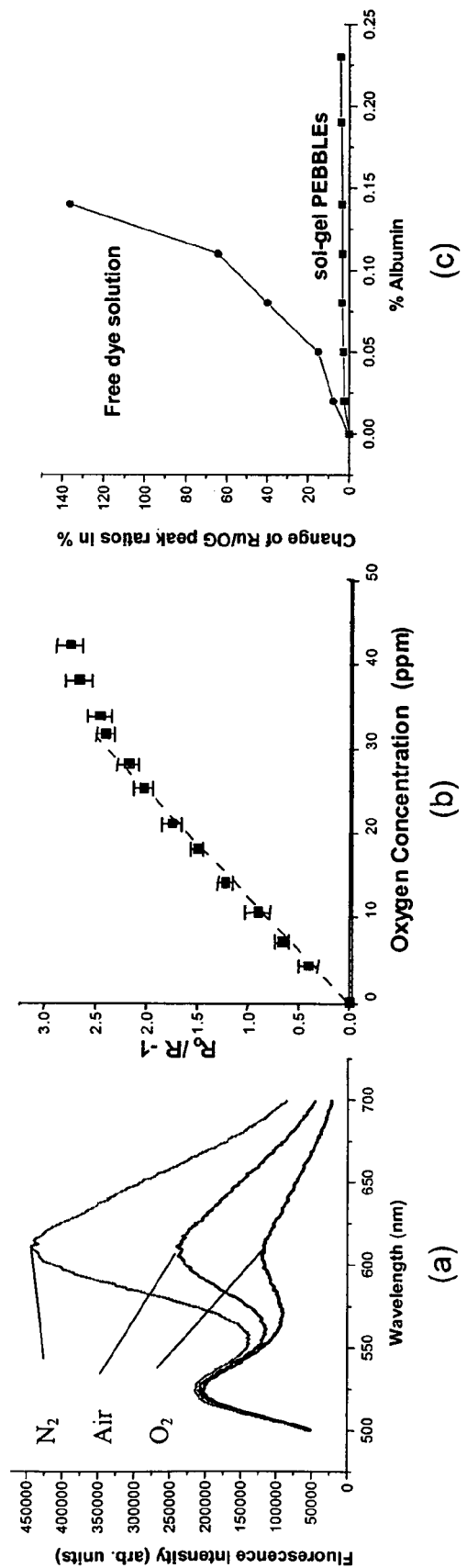
FIG. 26 shows measurements made with ratiometric oxygen sensing PEBBLEs.

In some embodiments, PEBBLE encapsulation is utilized, thus preventing the dye from poisoning the cell, and proteins in the cell from affecting the dye. Recent results indicate that PEBBLE formulations are non-toxic. FIG. 26a shows the spectrum for oxygen sol-gel PEBBLEs in solutions with different concentrations of dissolved oxygen. FIG. 26b shows a calibration curve for the oxygen sensors. In contrast to free ("naked") dye, the oxygen PEBBLEs show little interference from large proteins such as albumin as shown in FIG. 26 *c*)

In some embodiments, Surface Enhanced Raman Spectroscopy (SERS) is used to increase the Raman signal from certain molecules attached to silver and gold nanoparticles by ~$10^{16}$, enough to make them as bright as single fluorescent molecules. Raman spectroscopy provides detailed information about a molecule's environment due to the sharper lines obtained in Raman spectroscopy. Signals from Raman active molecules can be rapidly identified. In addition, Raman excited dyes photobleach very slowly. Recently, SERS was used to identify and image Raman signals from native DNA, RNA, phenylanine, tyrosine, and other molecules adsorbed onto gold nanoparticles within a single cell (Kneipp et al., Applied Spectroscopy. 2002 February; 56(2):150-154).

B. High Throughput Drug Screening

In some embodiments, the present invention provides methods of performing high-throughput drug screening using MagMOONs or Brownian MOONs (e.g., using the methods for intracellular analyte sensing and probes described above). The low background obtained with MOON technology allows sensitive detection of a panel of analytes to be detected in samples with large background fluorescence such as homogenates, cells, and tissues. A library of drug response curves can thereby be rapidly obtained.

Figure 27:
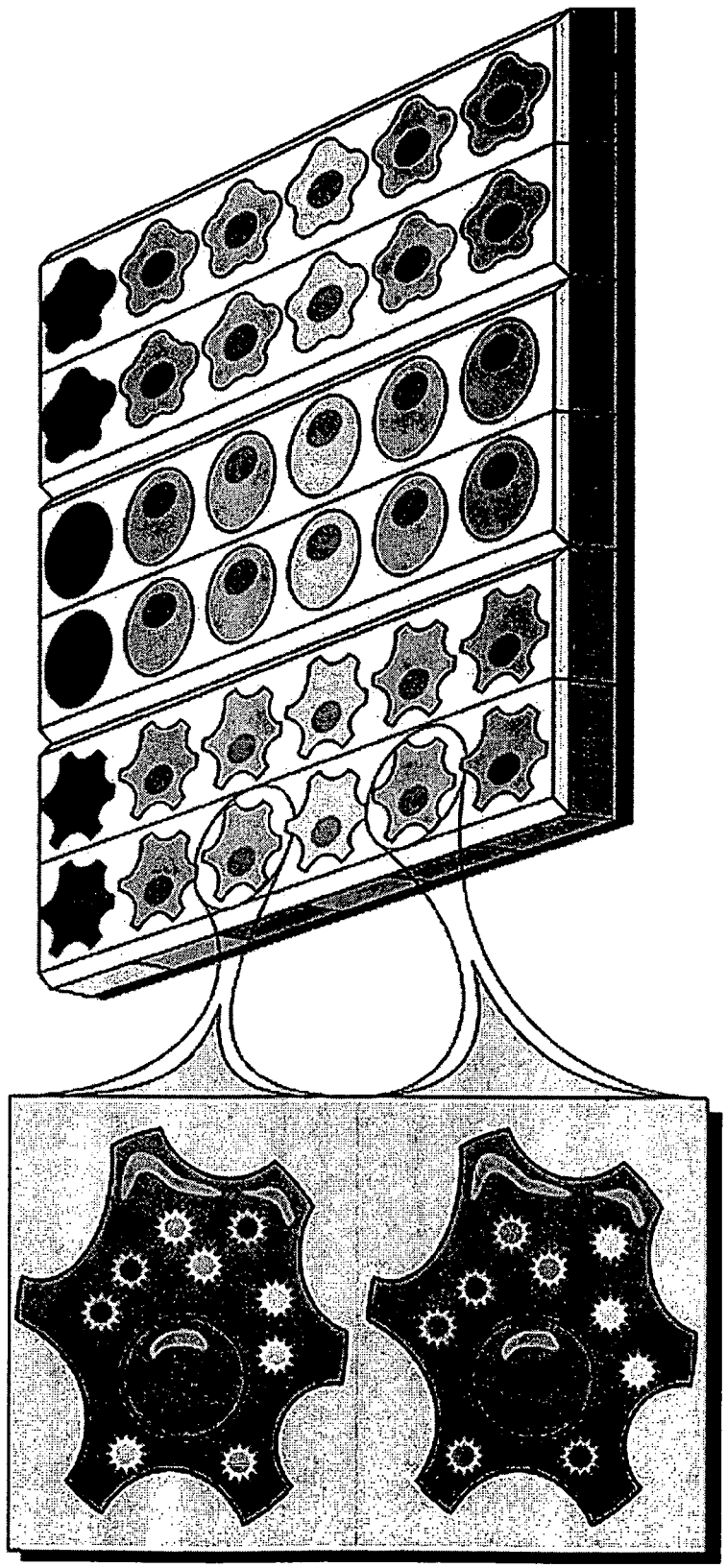
FIG. 27 shows a schematic of a high throughput drug screening/pathogen fingerprinting array using cells or tissues containing MagMOONs.

For example, in some embodiments, an array is used for pathogen fingerprinting based on cellular responses to various pathogens in combination with immunoassay detection. FIG. 27 shows a schematic of a high throughput drug screening/pathogen fingerprinting array using cells or tissues containing MagMOONs. In some embodiments, a 96 or 384 microwell plate is utilized. The samples may be cells (as shown), or tissues, or fluids.

For example, in some embodiments, multiplex detection is utilized to detect the effect of a panel of drugs on multiple cellular responses. Multiple MagMOONs or Brownian MOONs, or one type of MagMOON with multiple sensors, are introduced into a cell, homogenate, or tissue. Any suitable delivery method may be utilized including, but not limited to, liposomal delivery, gene gun, microinjection, and magnetic injection (particularly for the non-spherical/needle shaped MagMOONs). The sample is then contacted with the drug library or drug and the response in monitored (e.g., using the devices described below).

C. Portable Detection

In yet other embodiments, the present invention provides a portable assay system (e.g., immunoassay) that utilizes MagMOONs or Brownian MOONs. Immunoassays are becoming more prevalent and useful as more specific antibodies are found. A Mag or Brownian MOON immunoassay system provides a sensitive, flexible, rapid, robust, and inexpensive method for the detection of antigens. In some preferred embodiments, the immunoassay system is a portable unit for field work (e.g., for on-site pathogen testing). In other embodiments, the immunoassay system is a highly sensitive sensor for use in clinical diagnostics. In some embodiments, the immunoassay systems of the present invention include competitive and sandwich immunoassays.

The fluorescent immunoassay methods of the present invention provide several improvements over the chemiluminescent methods commonly used for immunoassay. For example, fluorescent dyes typically emit ~100,000 photons per molecule (as opposed to chemiluminescence which emits <1 photon per molecule). However, the signal/background is similar to chemiluminescence, allowing detection of smaller amounts of antigen and the use of more weakly fluorescing dyes. The methods of the present invention provide more rapid detection than chemiluminescence, which requires long exposure times to get good Signal/readout noise. In addition, washing steps are not critical because any unbound dye or contamination will be subtracted out as unmodulated background. The methods are robust and utilize standard electronic and optical components (See e.g., below description of devices). Background elimination allows a wider range of dyes to be used, allowing more analytes to be detected simultaneously. Even more multiplexing is achieved by using both MagMOONs that blink once and twice per revolution.

In some embodiments, additional multiplexing is achieved by detecting individual MagMOONs that are color coded (e.g. Red:Green:Yellow ratio can indicate which type of Mag-MOON is being detected). In some embodiments, a ratio dye in the particle is used to allow detection that is not affected by particle concentration and light intensity. A number of samples containing MagMOONs are placed in a microwell plate. Within each well, a number of individual blinking particles are located with software designed to look for blinking signals. Once located, the fluorescence at different excitation and/or emission wavelengths is determined by using a CCD with a filter wheel, or an array of sensors with different optical filters in front of them. For example, if the blue dye is used as an absolute reference, and ten gradations of red and green dyes are used, then there are 100 possible combinations of red and green dye possible. If another dye is added, another factor of 10 multiplexing is possible. Luminex Corp (Austin, Tex.) produces microspheres containing ten levels of each of two dyes allowing 100 analytes to be detected in one solution within a flow cytometer.

D. Biopsy Screening

In still additional embodiments, MagMOONs or Brownian MOONs are utilized in biopsy screening. Blinking particles that attach to specific cancer cells find use in biopsies where there is a low density of antigen, and fixing increases autofluorescence while masking potential binding sites. The ability of the methods of the present invention to eliminate background autofluorescence allow for their use in tissue samples for the detection of antigens associated with disease (e.g., cancer).

In some embodiments, the present invention provides biopsy test kits. In preferred embodiments, the kits include all of the components necessary for performing the immunoassay (e.g., MagMOONs, controls, buffers, etc.). In some embodiments, the test kits are approved for use as an in vitro diagnostic assay by the U.S. Food and Drug Administration (FDA).

E. Local Modulated Light Source

In some further embodiments, MagMOONs are used as a local modulated light source instead of a chemical probe per se. For example, in some embodiments, this source is used to measure absorption and fluorescence in the neighborhood of the particles. Such embodiments, find use in applications utilizing particles that are attached to specific regions of a cell (e.g., ion channels) using antibody coated probes.

F. Viscometer

In yet other embodiments, magMOONs and Brownian moons are used in the measurement of viscosity of solutions. The rotation rate of the MagMOONs depends on the frequency and waveform of the external magnetic field, the particle size and shape, and the fluid viscosity. For a given particle in a given field strength, the rotation rate is a measure of the rotational viscosity at the particle size scale. In homogeneous, Newtonian fluids, the microscopic rotational viscosity is equal to the bulk viscosity measurement independent of the method used; however for complex and heterogeneous fluids, viscosity measurements vary by orders of magnitude, depending on probe size and method used to probe. For example, if sieve like structures are present, probes smaller than the sieves experience a very different viscosity than particles larger than the sieve size; similarly for translation is impeded far more than rotation for probes in cavity structures including endosomes.

Compared to previous methods of measuring rotational micro and nano-viscosity using a laser trapped magnetic particle with an optical defect, metal-capped MagMOONs provide almost spherical-shaped particles, with bright and reproducible optical properties. In some preferred embodiments, particles with vapor deposited magnetic material have uniform and controllable magnetic properties, and can be easily made in a wide range of sizes.

In other embodiments, Brownian MOONs find use in the measurement of rotational viscosity. Bulk rotational viscosity (and active forces within a cell pulling on phagosomes) may be calculated by measuring the amount of time it takes for the magnetic vector from 1.8 μm magnetic particles to rotate inside macrophages. Certain drugs affect the rigidity of the cytoplasm and ingestion of small particulates of different types of materials affect the viscosity of the macrophages. However, in prior methods, a million macrophages and 10 μg of magnetic material were used to get a good reading. Thus, this method requires expensive sensitive equipment that lacks the sensitivity and resolution to measure rotational viscosity in single cells or to track the particles' locations, or to correlate viscosities to any chemical changes inside the phagosome or cytoplasm. In addition, it is difficult to make particles with uniform size and magnetic properties, making it difficult to probe viscosities at different sizes. In contrast, for Brownian MOONs, a wide selection of monodispersed particles is easily produced or commercially available, and even single nanometer sized particles are easily detected.

Rotational viscometers are commonly used in materials research and quality control. It is likely that rotational viscosity at the 50 nm-5 μm scale is an important parameter to measure for a large number of liquids, liquid crystals and polymeric materials.

Other methods of calculating viscosity include, but are not limited to, measuring the phase delay compared to the driving field for $\omega<\omega_{max}$, measuring the frequency of the slow rotation rate and fitting to the curve, measuring the maximum rocking rotation rate, or using different driving waveforms such as step function rotations and fields that oscillate +/−90°. Some use of the last two methods are more easily adapted to measure the viscosity and elasticity of the medium as a function of frequency.

Viscosity measurements and spectral modulation may also be made in flowing solution. Experiments conducted during the course of development of the present invention observed MagMOONs rotating and blinking in solutions of water that were evaporating and causing high local flow rates.

G. Particle Binding

In still further embodiments, MagMOONs and Brownian MOON probes find use in the measurement of particle (e.g., microorganism or biological molecule) binding to the probe. In some embodiments, MagMOON rotation rate is monitored over time in order to detect binding of molecules and particles to the MagMOON surface. As binding occurs, the maximum rotation rate of the particle changes (maximum rotation rate increases with the cube of the particle radius for spherical particles). This method allows detection of antibodies, viruses and bacteria that bind to the particle. The sensitivity to changes in MagMOON thickness increases for smaller MagMOONs, allowing tracking of individual binding events and measuring the increased drag from single binding events. In other embodiments, the method is used to measure particle swelling and dissolving.

In some embodiments, Brownian MOON rotation rate is monitored in time in order to detect binding of molecules and particles to the MOON surface. As binding occurs, the rotational diffusion rate of the particle increases (rotational diffusion rate increases with the cube of the particle radius for spherical particles). This method allows detection of antibodies, viruses and bacteria that bind to the particle. The sensitivity to changes in Brownian MOON thickness increases for smaller Brownian MOONs, allowing tracking of individual binding events and measuring the increased drag from single binding events. In other embodiments, the method is used to measure particle swelling and dissolving.

Based on current data with MagMOONs, maximum rotation rate can be measured to better than 0.25%, and because it is a temporal-based measurement, significantly higher sensitivity is possible. Using a 0.25% change in rotation rate for a 4 μm particle corresponds to being able to detect a 3.3 nm increase in diameter or 1.7 nm in radius. Smaller particles (which may be formed using vapor deposition of magnetic material) are more sensitive to binding: a 0.25% change for a 400 nm particle corresponds to a 2 Å change in thickness across the particle surface, and with a 50 nm particles, it is possible to see individual binding events for antibodies and measure the increased drag. In some embodiments, the technique is used for measuring drag of molecules in solution, detecting binding equilibrium for individual molecules and particles, and detecting binding with viruses and bacteria. In addition the effects of binding are amplified if the binding affects the way the MagMOON chemically interacts with the surrounding medium (in the most extreme case binding to a surface).

III. Devices

In some embodiments, the present invention provides devices for use in MagMOON detection. In preferred embodiments, the devices comprise a means for orienting particles in a magnetic field and a fluorescence detector. In some embodiments, the devices further comprise software for the analysis (e.g., demodulation) and presentation of the data. In some embodiments, the devices are compact and portable (e.g., portable immunoanalyzers).

A. Orienting Means

The devices of the present invention comprise an orienting means for rotating magnetic probes. In some embodiments, the orienting means is a magnet. The present invention is not limited to a particular magnet. Any suitable magnetic system that is able to rotate the MagMOONs of the present invention may be utilized. For example, in some embodiments, a permanent magnet is fixed to a motor and spins when the motor is on. By increasing the rate of rotation of the motor, the particles rotate faster. In other embodiments, two or three perpendicular solenoids fed by alternating electric fields 90 degrees out of phase are utilized. The rate of particle rotation adjusted by changing the frequency of the current in the solenoids.

B. Fluorescence Detection

The devices of the present invention further comprise a fluorescence detection apparatus. Any suitable excitation source may be utilized including, but not limited to, a laser, an LED, a mercury lamp, or any other source that generates enough intensity light at the excitation wavelength. Illumination may occur at any angle with respect to the detector and magnetic field. In some embodiments where multiplex detection is desired, devices are designed to simultaneously detect MagMOONs fluorescing at different frequencies. For example, in some embodiments, the device comprises a rotating filter wheel for detection of multiple wavelengths (See e.g., U.S. Pat. Nos. 5,171,534, 5,374,527; each of which is herein incorporated by reference). In other embodiments, multiple detectors are utilized (e.g., one detector per fluorescent dye). In still further embodiments, a diffraction grating is used to provide the entire spectrum of fluorescence from one line in the image. By moving the line across the image, a three-dimensional image with spectral intensity along the third axis is constructed.

C. Demodulation

In some embodiments, the device further comprises software or hardware for the demodulation of fluorescent signals.

The fluorescent signal from the sample may have several frequency components. For example, it may have a steady background from autofluorescence, a signal at 1 Hz due to heart beats, a signal at 20 Hz due to muscle activity, a signal at 120 Hz due to stray room light flickering, and a signal from the indicator particles at the frequency of magnetic field rotation. The characteristic frequencies of the background noise is determined by measuring the fluorescent signal in time in the absence of any magnetic fields. The frequency of magnetic field rotation is then chosen to avoid any spikes in the background frequency spectrum (e.g., by measuring multiple frequencies). There are a number of methods to extract the signal that is at the frequency of the magnetic field rotation. For instance, in some embodiments, the Fourier transform of the intensity/time curve is taken, the size of the signal is at that frequency is utilized. In other embodiments, electronic filters or lock in amplifiers are utilized to select the desired frequency.

In some embodiments, demodulation is performed by taking two images: one with the particles oriented so that their fluorescence is "on," and the other with fluorescence "off." By subtracting the "off" images from the "on" images, constant background signals are removed leaving only an image of blinking (or moving) particles as illustrated in FIG. 7. In other embodiments, the spectrum from modulated particles is demodulated by taking two spectra, one with the particles oriented "on," and the other with the particles oriented "off." By subtracting the "off" spectrum from the "on" spectrum, constant background signals are removed leaving only the spectrum of the blinking, or moving particles, as illustrated in FIG. 18.

In some embodiments, the background signal is utilized to provide information that is used in conjunction with information from magnetic probes. For example, autofluorescence from NADH may indicate metabolic activity. In other embodiments, fluorescence signal affected by blood pulses is measured by filtering signal intensities at the blood pulse rate.

D. Exemplary Devices

Figure 4:
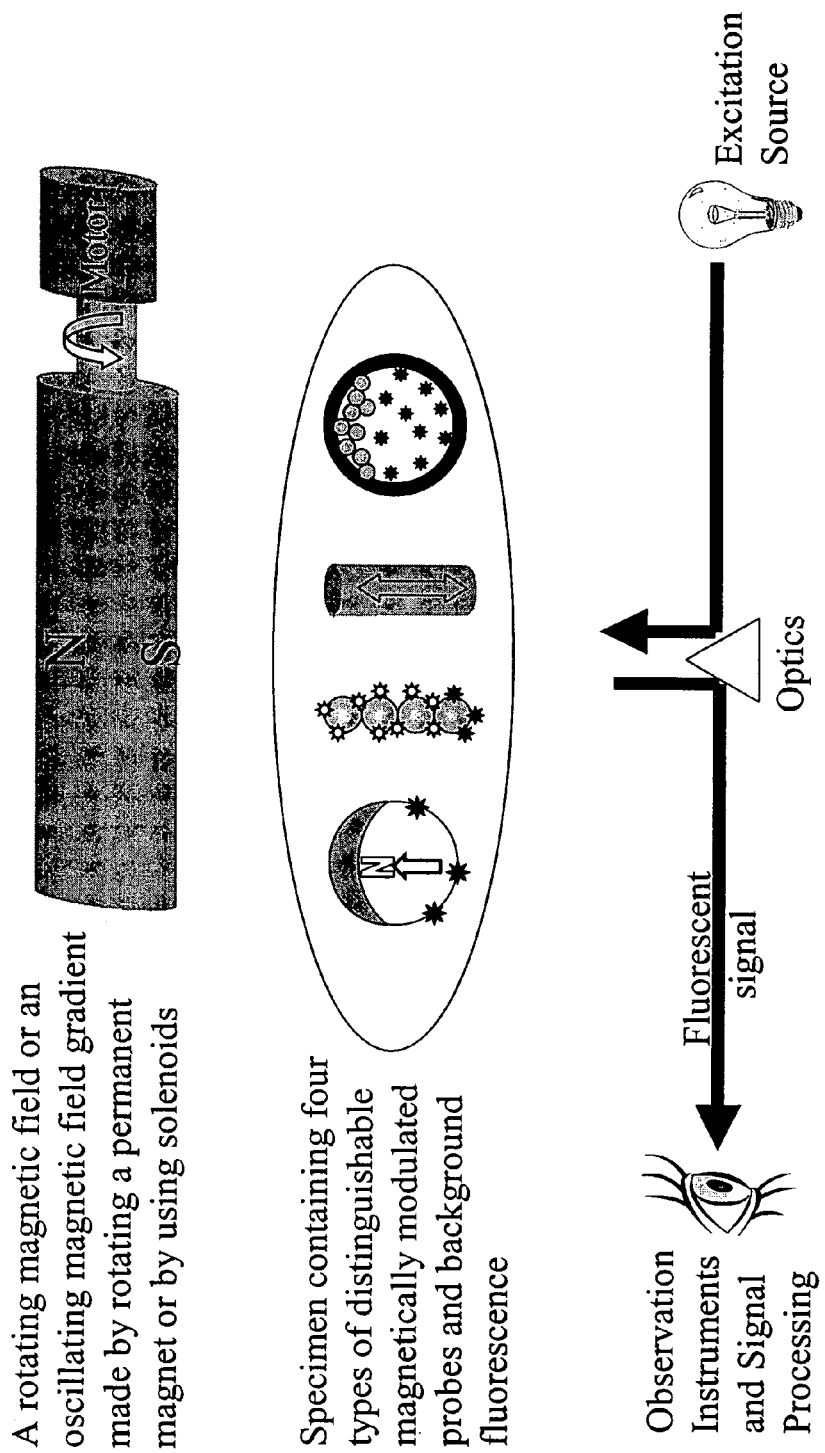
FIG. 4 shows a schematic of magnetic modulation and signal extraction utilized in some embodiments of the present invention.

FIG. 4 shows a schematic of an exemplary experimental setup useful in some embodiments of the present invention. A rotating magnetic field or oscillating magnetic field gradient modulates MagMOON fluorescence. A light source excites fluorescence in the sample, and the fluorescent signal is sent to a CCD, spectrometers, photodiodes, or other detection means. A lock-in amplifier, or software analysis of a series of images or spectra, is used to separate out and analyze the modulated components of the signal. Four distinguishable types of MagMOONs are shown in the figure, metal-capped permanent magnetic MagMOONs, non-spherical MagMOONs (that blink twice per revolution), polarized MagMOONs, and gradient sensitive MagMOONs in a nanobottle.

The present invention is not limited to a particular detection device. Indeed, the present invention contemplates that devices will be modified to better suit the particular application or environment that the device is utilized in. For example, in some embodiments, immunoassay analyzers are utilized that comprise a 96-well fluorescent plate reader modified to include magnets. In other embodiments, small, portable immunoassay analyzers are utilized. In other embodiments, a generic magnetic modulator is added to standard microscope and fluorimeter setups to detect blinking MagMOONs using simple software. In yet another embodiment, a means of magnetic modulation is added to a confocal laser microscope, and a lock-in amplifier (or other electronic filter) is linked to the detector in order to form images of blinking particles in a sample.

The present invention may also be used in flow cytometers where a liquid sample is broken into droplets that pass single file through a detection apparatus. The particles may be made to blink within the detector chamber to eliminate any interference between particle and background spectra. In one embodiment, a rapidly oscillating magnetic field rotates the particles within the detection chamber. In another embodiment, the particles rotate as they move past a series of permanent magnets that alternate in polarity.

EXPERIMENTAL

The following examples serve to illustrate certain preferred embodiments and aspects of the present invention and are not to be construed as limiting the scope thereof.

Example 1

Methods of Generating Non-Spherical Microparticles

This Example describes methods for the generation of aspherical microparticles from spherical microparticles.

Fluorescent polystyrene microspheres 3.4 µm in diameter were purchased from Bangs labs. Polystyrene microspheres containing ferromagnetic chromium dioxide 2 µm and 4.4 µm in diameter were purchased from Spherotech. Iron oxide nanoparticles were obtained from Magnox. Fluorescent decyl methacrylate and silica sol gel nanospheres were polymerized in our lab. Glass microscope slides were purchased from Fisher Scientific.

Polystryrene microspheres were deposited onto a microscope slide and the slide was clamped to a laser table. A second slide was placed on top to sandwich the particles. The top slide was then moved laterally while applying pressure with the fingers (FIG. 10a). With a low concentration of particles and small lateral motions, single particle rolls are formed, while with a high concentration of particles and large lateral motions, the rolls form together into multirolls. The rolling procedure was performed with microspheres that are either suspended in solution, or dry. The preferred procedure was to suspend the microspheres in ethanol and deposit them on a microscope slide to dry before rolling.

Disk-shaped microparticles are formed using a ¼" diameter glass tube with a metal pin through it to flatten deposited microspheres. This method is also used to form coupled disks and to flattened rolls and multirolls.

Smaller particles were implanted into larger particles by applying the small particles to the microscope slide before the larger microspheres were added. The smaller particles were implanted into the larger particle rolls or disks during the normal rolling or flattening procedure.

The processes were found to works wet or dry, with large concentrations of particles or small concentrations, with polystyrene particles, and magnetic polystyrene particles, and in the presence of small particles for implanting.

Rolls and multirolls of magnetic polystyrene particles implanted with fluorescent polystyrene, sol gel, and decyl methacrylate have been formed. FIG. 11b shows a CCD image of fluorescently breaded magnetic microspheres. Due to their magnetic shape anisotropy, these rolls align with external magnetic fields when placed in solution.

Fluorescent polystyrene pancakes have also been formed, and disks have been generated with implanted magnetic material. The magnetically implanted fluorescent disks align with external magnetic fields. These magnetically implanted disks were stable in water for at least five days.

Example 2

Generation of MagMOONs

Figure 28:
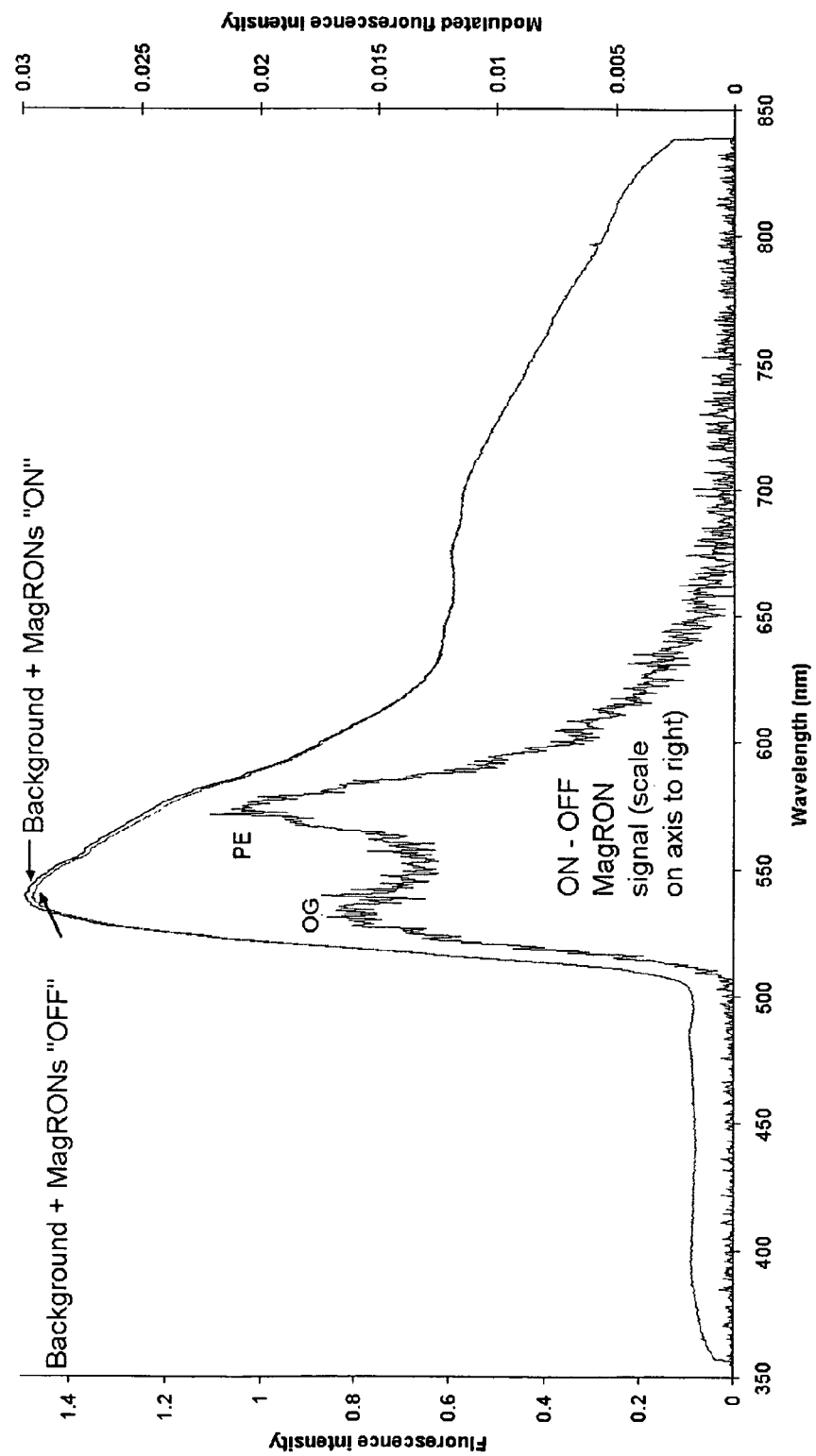
FIG. 28 shows gold-capped MagMOONs binding to Oregon-Green biotin and phycoertyrin-biotin.
Figure 29:
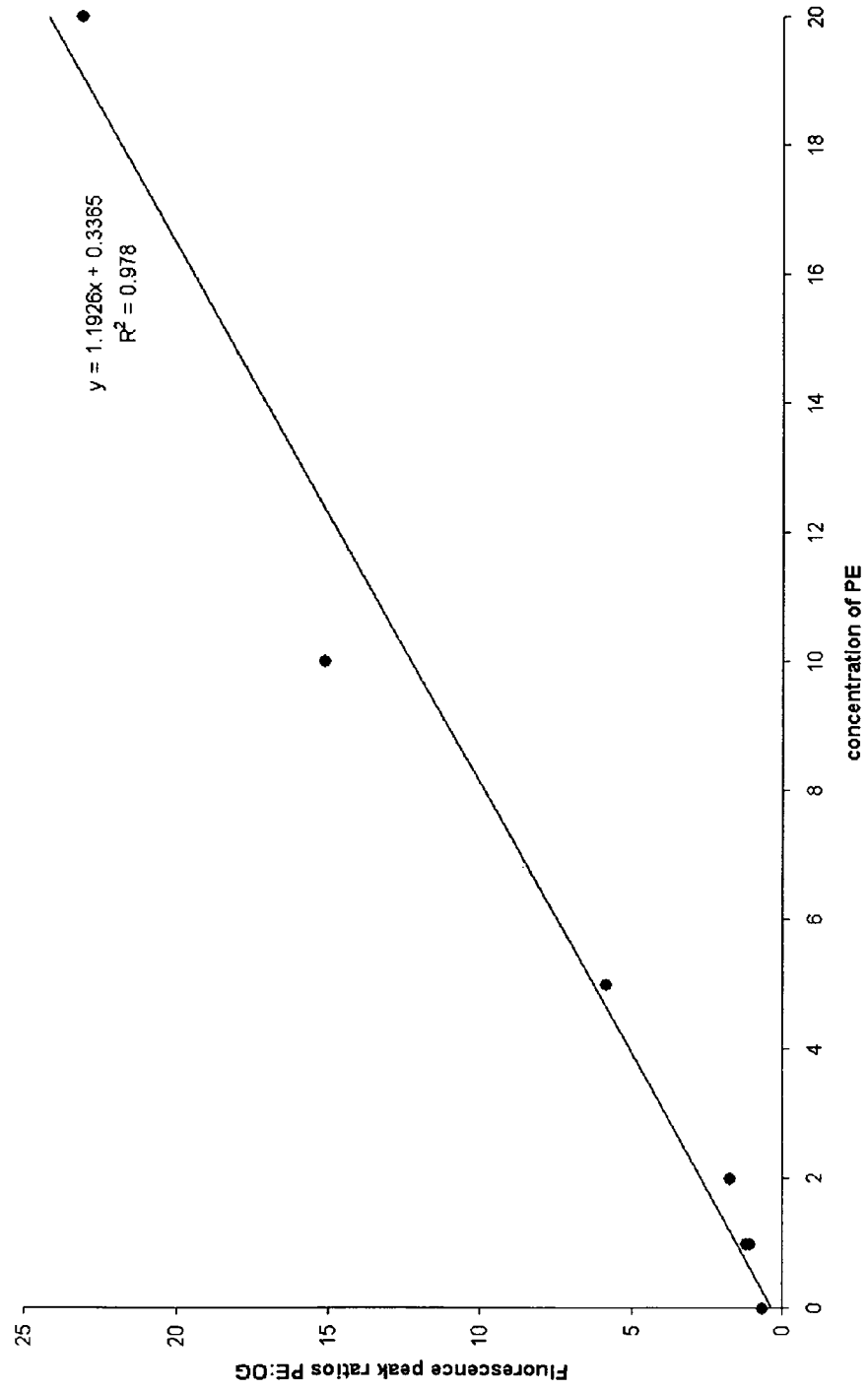
FIG. 29 shows an immunoassay to measure the percentage of fluorescent labeled biotin.

This example describes the generation of gold-capped streptavidin MagMOONs. The MagMOONs were then immersed in solutions a fixed concentration of Oregon Green labeled biotin (OG) and a varying concentration of Phycoerythrin labeled biotin (PE). A 20 µl drop of each solution was placed on a silanized glass microscope slide (silanized to keep the drop compact). A stepper motor rotated a cylindrical magnet in two orientations to orient the MagMOONs "on" and "off," while a CCD camera was used to take fluorescence of the MagMOONs in "on" and "off" states. A blue excitation source from a mercury lamp, and 4× lens on a microscope was used. The focus of the microscope was raised to particles floating in solution to avoid viewing polystyrene particles that were adhered to the silanized glass. No washing step was performed. This example demonstrates that, by rotating the MagMOONs, it is possible to separate the MagMOON fluorescence from background fluorescence due to instrument optics, contamination, and free excess biotin-labeled dyes as shown in FIG. 28. The ratio of the PE to OG peak increased linearly with increasing PE concentration (FIG. 29).

Example 3

Generation of Metal-Capped MagMOONs

Fluorescent polystyrene microspheres 4.4 µm in diameter containing ferromagnetic material (Spherotech, Libertyville Ill.) were deposited on a microscope slide and one hemisphere of the particles is coated with either vapor deposited aluminum or sputter coated gold. The metal layer prevents excitation light from entering and fluorescence from leaving the coated side of the particle. It is preferred that the metal layer is thicker than the skin depth of the excitation or emission light, although thinner layers will still allow modulation. In this example, aluminum layers 100 nm thick (skin depth on the order of 20 nm) were used. Quenching of the dye molecules by the metal is not a problem since most of the dyes are not in immediate proximity (<10 nm) to the metal. The microspheres are magnetized so that their north side is uncoated. The particles were then removed from the slide with a paint brush and suspended in solution by sonication. When in solution, the particles orient in an external magnetic field. By rotating the field, the particles are made to rotate, and appear to blink synchronously as their light emitting sides come in and out of view (FIG. 2). Since only the probes rotate, any constant background fluorescence can be separated from the probe signal.

Ovine Albumin (Egg White)

The MagMOONs were added to ovine albumin (egg white), a medium with similar makeup to cytosol. The albumin fluoresced green while the MagMOON fluoresced yellow. By rotating the MagMOONs with the computer-controlled magnet, the MagMOON fluorescence was separated from background, decreasing the reflected mercury lamp background at 800 nm by a factor of 4,000 and rendering negligible the green background fluorescence from the albumin.

Using principle components analysis, a more sophisticated signal analysis than the simple "on" minus "off," the background from the mercury lamp was decreased by a total factor of more than 10,000.

Imaging Under a Leaf

Blinking MagMOONs may also be spatially located by subtracting "on" minus "off" images. Locating MagMOONs and reading their fluorescent signals enables high sensitivity measurement of chemical concentrations in cells and tissues, high contrast molecular tags and contrast agents, and the ability to perform thousands of bioassays simultaneously in a single fluid sample by first locating the MagMOON and reading its signal, and then identifying it based on an optical encoding scheme. To demonstrate particle localization and background subtraction in images thin sections were sliced from an ivy leaf and place them on a microscope slide with a few drops of dilute aluminum-capped MagMOON solution, wetting the slide below the leaf. A magnet was rotated continuously with a motor drive. Blinking MagMOONs were easily distinguished from leaf fluorescence. FIG. 7 shows images of an aluminum-capped MagMOON floating below a brightly fluorescing leaf section. Figure shows the MagMOON magnetically oriented ON; the MagMOON magnetically oriented OFF; and ON minus OFF (which removes the background leaf fluorescence).

Continuous Modulation

Portable MagMOON immunoassays and chemical sensors may be based on simple devices containing rotating permanent magnets or solenoids, photodiodes to measure light intensity at specific wavelength regions, and electronic filters to separate MagMOON fluorescence from background. To demonstrate the principle, a magnet was rotated continuously at 10 Hz above a drop of water containing aluminum-capped MagMOONs. Fluorescence intensity from instrument autofluorescence and rotating (blinking) MagMOONs was measured using a photomultiplier tube. The signal at 10 Hz was 400 times the background signal at 15 Hz, for a total factor of 4000 signal over background increase. Harmonics at 20 Hz, 30 Hz, 40 Hz, and 50 Hz are also present in the Fourier Transform. Ten seconds of data were analyzed for this graph.

Immunoassays

Gold-capped streptavidin coated MagMOONs were generated by sputter coating gold onto one hemisphere of streptavidin coated permanent magnetic microspheres (Spherotech). These MagMOONs were then immersed in solutions with a fixed concentration of Oregon Green labeled biotin (OG) and varying concentrations of Phycoerythrin labeled biotin (PE). The biotin-streptavidin bond, a strong and highly specific biological bond used as the basis for many immunoassays, attached the fluorophores to the MagMOON. No washing step was performed since fluorescence from the excess dye is not modulated and can be subtracted off. A 20 μl drop of MagMOON and dye solution was placed on a glass microscope slide that was silanized to keep the drop compact. A blue excitation source from a mercury lamp, and 4× lens on a microscope was used. The focus of the microscope was raised to particles floating in solution to avoid viewing polystyrene particles that were adhered to the silanized glass. By rotating the MagMOONs with the computer controlled magnet, it was possible to separate the MagMOON fluorescence from background fluorescence due to instrument optics, contamination, and free excess biotin-labeled dyes. Experiments were performed with six different PE concentrations. The ratio of PE to OG spectral peaks from the MagMOONs increased linearly with concentration of PE in solution, unaffected by background fluorescence.

Example 4

Direct Measurement of Streptavidin Fluorescence on MagMOONs

Many analytes of interest fluoresce under blue or ultraviolet excitation. However, large background signals common at these excitations limits sensitivity of direct fluorescent measurements in the ultraviolet. Instead, sandwich assays and competitive assays are performed using intense visibly excited dyes. However, addition of fluorescent labels complicates the procedure (especially if unattached labels need to be removed). The intrinsic fluorescence of streptavidin can be separated from background signals using magnetic modulation of streptavidin coated metal-capped MagMOONs.

Streptavidin coated 4-5 um ferromagnetic particles (spherotech) were capped with aluminum, suspended in a solution of deionized water, and modulated by orienting them "on" and "off" in magnetic fields. A fluorescent spectrum from the weakly fluorescing Streptavidin directly linkinked to the particles was detected. This weak signal contrasted with no detectable signal from a control (similar particles without Streptavidin), and strong fluorescent signals from Streptavin that had been fluorescently labeled with biotin linked fluorophores.

Example 5

Preparation of 300 nm pH Sensing MagMOONs

Magnetic modulation of optical signals is a general technique that rejects background and increases signal to noise ratios for any dye or optical label that can be attached to or embedded within MagMOONs. In addition to improved immunoassays, MagMOONs improve intracellular measurements where autofluorescence has severely limited the range of dyes and samples that can be detected with reasonable signal to noise ratios. PEBBLE nanosensors measure concentrations of ions and small molecules within a single cell, rapidly, sensitively, with high spatial resolution, and without interference from cellular proteins. Combining them with MagMOONs allows highly sensitive detection of intracellular analytes using a broad range of dyes. Such measurements lead to a better understanding of how cells function and how cells are effected by drugs, toxins and pathogens.

Barium ferrite (BaM) crystals of 30 and 60 nm diameter were a donation from Toda Kogyo Corp. The crystals were ground for one hour in an aluminum oxide mortar and pestle. Approximately 200 mg of ground BaM were sonicated for one hour in 24 mL of an ethanol solution that contained 2M ammonia and 6M deionized water. After sonication, the suspension was centrifuged for 15 minutes at 500 RPM to remove aggregates. 24 mL of supernatant were transferred to a 100 mL round bottom flask. To the same flask was added 800 μL dextran linked SNARF pH indicator dye (5 mg dye per 1 mL deionized water). The polymerization reaction was initiated by adding 70 μL tetraethylorthosilicate (TEOS). The reaction was allowed to progress for 2 hours, after which the silica nanoparticles were removed by vacuum filtration. To prepare MagMOONs, a suspension of BaM/SNARF silica nanoparticles in deionized water was deposited on a glass microsope slide. After the water evaporated, the nanoparticles were coated with aluminum by vapor deposition. The MagMOONs were magnetized by placing the slide in a magnetic field. The MagMOONs were removed from the microscope slide by gently stroking the slide with an artist's paintbrush.

Example 6

Modification of Microwell to Allow Magnetic Modulation of MagMOONs

Copper wire was wrapped 30 times around a thin tube of plastic that could be inserted snugly into a microwell on a standard microwell plate. The plastic tube was made from a section cut out of a 1 ml pipette tip. A solution of 4-5 um MagMOONs as described above was added to the microwell. A small positive current passed through the coil created a field that oriented all metal-capped MagMOONs in a solution in the well "on." A small negative current oriented all MagMOONs in the well "off." With no current, the particles all aligned with the remnant field in the room, and were oriented in a phase of the moon closer to "on" than "off." This example demonstrates that a simple inexpensive modification of existing microwells will allow standard plate readers to read "on" and "off" signals from MagMOONs in solution without any moving parts.

A drop of highly scattering 150 nm polystyrene nanospheres was added to 200 µl of MagMOON solution in the well. The fluorescent signal was magnetically modulated in spite of the scattering from the 150 nm microspheres. This result indicates that MagMOONs can be modulated in scattering media.

Example 7

Modulating Transmittance Through Metal-Capped MagMOONs

This example describes modulated transmission through metal capped MagMOONs. More light passed through with the particles in a half-moon orientation than either full or new MOON orientation. The transmission was also modulated through a thin capillary containing chains of 1 µm magnetic microspheres and through magnetic paper with drops of oil with nickel particles free to rotate within the drops. Transmission, and FTIR signals were modulated through the magnetic paper. Signal can be modulated even after light passes through highly scattering films of polishing paper. A thin sensing film can be coated onto the magnetic paper allowing magnetic modulation of light flux passing through the coated film but without reorienting the film itself.

Example 8

Modulating Fluorescence from a pH Sensing Microdrill

A 2 mm wood screw was attached using epoxy glue to a 2×2×10 mm NdFeB magnet magnetized through the width (Dexter magnets) in order to make a magnetically driven remote drill. The drill could propel through an agarose gel.

The drill was then coated by a thin fluorescent pH sensing layer. The coating was performed by dipping the screw part of the drill in a solution of 1 ml THF (tetra hydra furan), 80 mg of 6000 Mw polystyrene, 50 µl of DOS (plasticizer) and 2 mg of the pH sensing dye CNF (carboxynaptho fluorescein). The screw was removed to allow the THF to evaporate and deposit a thin layer of pH sensing polystyrene film. Next, one section of the drill was coated with a layer of black ink applied with a Sharpie felt tip pen. The drill was driven into an agarose solution with a rotating magnetic field, and then a series of spectra were taken with the drill rotated back and forth to the "on" and "off" positions. Subtracting "On" minus "Off" spectra clearly and reproducibly removed background signals.

The aspherical property of the rectangular magnet could also be used to modulate ultrasound signals in order to accurately identify probe location, or to use the probe as a modulated ultrasound source.

Example 9

Preparation of Optically Polarized Magnetic Particles

Magnetic fluorescent particles 1-2 µm in diameter (Polysciences) were deposited on a microscope slide. The slide was placed in a ~1 mm laser beam with a linear polarizer placed in the light path for 180 minutes to bleach one polarization of fluorophores in the microspheres. Periodically during the bleaching, the fluorescence emission of the particles was measured at polarizations 0 and 90 degrees to the excitation light. During bleaching the intensity of fluorescence emission polarized parallel to the bleaching beam decreased by a factor of 5.5 while the intensity polarized perpendicular decreased by only ~20%. Five days after the bleaching was stopped, the particles remained polarized with the parallel polarization still 2.5 times less than originally and the perpendicular component ~10% less than originally.

Example 10

Moving MagMOONs Using Magnetic Tweezers and Using Movement as a Means of Modulation In some embodiments rotating magnetic fields modulate MagMOON signals, while in other embodiments, magnetic field gradients modulate signals from MagMOONs. In addition, gradients can be used to guide single MagMOONs as well as create and guide swarms of MagMOONs to places of interest. Moving particles and swarms into and out of view with magnetic tweezers provides a means of modulating their signal with field gradients and thus separating it from backgrounds.

A simple magnetic tweezers apparatus was used to move swarms of particles and single particles through a rectangular capillary. The magnetic tweezers consisted of a thin iron wire 250 µm or 75 µm in diameter (Alfa Aesar) held in a magnetic field created by either a permanent magnet or an electromagnet. The iron wire concentrated the field and made a strong field gradient near the tip that was used to pull magnetic particles. By changing the orientation of the field, individual particles were reoriented, and chain-shaped structures in swarms reoriented themselves. The wand was removed after positioning particles or swarm so that the magnetic field orientation was unperturbed by the wire. Metal-capped MagMOONs, aspherical MagMOONs, and chains of MagMOONs were moved. Particles and swarms were moved into and out of view in order to module their fluorescent signal and subtract background. In addition, acid sensitive swarms of particles were moved through a region of changing pH in a capillary. Oxygen sensing and singlet oxygen were moved through a capillary to produce "stinging swarms."

Preparation of pH Sensing Gradient Sensitive Particles and Swarms

The synthetic procedure for iron oxide and ETH 5350 (9-(Diethylamino)-5-[(2-octyldecyl)imino}benzo[a]phenoxazine) embedded particles is as follows: Stock solution of 0.64M $FeCl_2.4H_2O$ and 1.28M $FeCl_3.6H_2O$ in 0.4M HCl was prepared ($Fe^{2+}/Fe^{3+}$ mixture solution). 280 mg of 750 nm hollow organically modified silica particles (ormosil) was suspended in 100 mL of 1.5M NaOH solution. 10 mL of $Fe^{2+}/Fe^{3+}$ mixture solution was then added drop-wise into the particle suspension for 30 minutes under sonication with $N_2$ gas blowing at room temperature. The iron oxide powder formed outside the hollow particles was isolated by applying an external magnetic field and remaining turbid brown solution was taken and filtered through a 450 nm filter membrane. The particles were then further rinsed with 300 mL of 0.01 M HCl and water several times and then dried to yield iron oxide embedded hollow particles. 1 mL of ETH 5350 in THF solution (1 mg/mL) was added into 10 mg of dry iron oxide embedded particles. Just enough THF to wet the particles was added more and the solution was allowed to stand for 2 hours. Most of THF was then allowed to evaporate under the hood. The resulting particles were rinsed with 1:1 water:ethanol mixture and allowed to air-dry. The hollow ormosil particles were obtained from professor Sang-Man Koo at Hanyang University in Korea.

The particles were suspended in an acid solution and the solution was used to wet a paintbrush. The brush was pressed into a rectangular capillary (Friedrich & Dimmock, inc.) and the solution entered by capillary action. The brush was then dipped into pH 13 base solution and pressed against the capillary to fill the rest of the capillary and create a gradient between a low pH solution on one end and a high pH solution on the other. A magnetic wand concentrated a swarm of magnetic pH particles in the acid side. The swarm was moved into view while a spectrum was taken, and then moved out of view while a second background spectrum was taken. The swarm was then moved to the other end of the capillary. The swarm had decreased in size during this 3 cm voyage as the experimenter moved the wand relatively rapidly and left the slower elements of the swarm behind. A large swarm remained in the high pH solution nonetheless, and this was moved into view while a spectrum was taken, and out of view while a background spectrum was taken. The background subtraction greatly decreased background from the mercury lamp in both the acid and base regions. The dye was ratiometric, so the spectral shape indicates pH concentration: the spectrum in high pH is blue shifted from the spectrum in low pH, as expected.

Preparation of Oxygen Sensing/Singlet Oxygen Producing Stinging Swarms

The processing steps for iron oxide embedded and ruthenium dye co-doped silica nanoparticles are as follows: 1 g PEG MW 5000 monomethyl ether, 3 mg $Ru(dpp)_3Cl_2$, were dissolved in mixed solution of 3 mL ammonium hydroxide (30% w/w) and 12 mL methanol. Upon mixing, the solution became transparent; 40 mg $Fe_3O_4$ was introduced before 0.1 mL TMOS (99.9%) was added dropwise to initiate the hydrolysis reaction. The solution was then stirred vigorously at room temperature for 2 hours before the reaction was stopped. After the reaction was stopped, the majority of unreacted iron oxide was attracted to the stirring bar and removed manually. The particles were further rinsed with at least 500 ml distilled water and 200 ml ethanol to ensure that all unreacted PEG and TMOS had been removed from the silica particles. The silica particle suspension was then passed through a suction filtration system (Fisher, Pittsburgh, Pa.) with a 200 nm filter membrane to collect the particles that were then dried to yield a final product of PEGylated silica nanoparticles.

Example 11

Methods of Generating Non-Spherical Microparticles by Physically Deforming Spherical Particles This Example describes methods for the generation of aspherical microparticles from spherical microparticles.

Fluorescent polystyrene microspheres 3.4 µm in diameter were purchased from Bangs labs. Polystyrene microspheres containing ferromagnetic chromium dioxide 2 µm and 4.4 µm in diameter were purchased from Spherotech. Iron oxide nanoparticles were obtained from Magnox. Fluorescent decyl methacrylate and silica sol gel nanospheres were polymerized using standard methods. Glass microscope slides were purchased from Fisher Scientific.

Polystryene microspheres were deposited onto a microscope slide and the slide was clamped to a laser table. A second slide was placed on top to sandwich the particles. The top slide was then moved laterally while applying pressure with the fingers. With a low concentration of particles and small lateral motions, single particle rolls were formed, while with a high concentration of particles and large lateral motions, the rolls form together into multirolls. The rolling procedure was performed with microspheres that are either suspended in solution, or dry. The preferred procedure was to suspend the microspheres in ethanol and deposit them on a microscope slide to dry before rolling.

Disk-shaped microparticles were formed using a ¼" diameter glass tube with a metal pin through it to flatten deposited microspheres. This method was also used to form coupled disks and flattened rolls and multirolls.

Smaller particles were implanted into larger particles by applying the small particles to the microscope slide before the larger microspheres were added. The smaller particles were implanted into the larger particle rolls or disks during the normal rolling or flattening procedure.

The processes were found to work wet or dry, with large concentrations of particles or small concentrations, with polystyrene particles, and magnetic polystyrene particles, and in the presence of small particles for implanting.

Rolls and multirolls of magnetic polystyrene particles implanted with fluorescent polystyrene, sol gel, and decyl methacrylate were formed. FIG. 11b shows a CCD image of fluorescently breaded magnetic microspheres. Due to their magnetic shape anisotropy, these rolls align with external magnetic fields when placed in solution.

Fluorescent polystyrene pancakes were also formed, and disks were generated with implanted magnetic material. The magnetically implanted fluorescent disks align with external magnetic fields. These magnetically implanted disks were stable in water for at least five days.

Example 12

Methods of Generating Chain-Shaped Non-Spherical Nano- and Microparticles

Chains of magnetic particles form spontaneously in a magnetic field. When the field is removed, the particles disperse. The chains align with the external magnetic field. By orienting the chains horizontal "on" and vertical "off" and subtracting the average "on" from "off" signal, the particle fluorescence can be separated from background fluorescence.

To demonstrate the principle of MagMOON immunoassays, streptavidin superparamagnetic nanospheres 870 nm in diameter (Bangs Labs) were immersed in solutions with a mixture of Oregon Green labeled biocytin (OG) and Phycoerythrin labeled biotin (PE) (Molecular Probes, Oreg.). The biotin-streptavidin bond, a strong and highly specific biological bond used as the basis for many immunoassays, attached the fluorophores to the MagMOON. The OG peak serves as a reference and at the same time illustrates the principle of a competitive assay: the OG is in competition with the PE for binding sites on the particle. No washing step was performed since fluorescence from the excess dye is not modulated and can be subtracted off. A MagMOON and dye solution was added to one well in a 96 well plate, and the solution was left overnight to let the biotin labeled dyes attach to the nanospheres. By orienting the MagMOON chains with the computer-controlled magnet, MagMOON fluorescence was separated from background fluorescence due to instrument optics, dust, and free excess biotin-labeled dyes. Thirty two pairs of ON and OFF spectra were collected, and the average ON, OFF, and ON minus OFF spectra were plotted. The background mercury lamp peak at 800 nm was attenuated by a factor of 2,000.

Chains of magnetic particles can be link together permanently by heating the chains up above their glass transition temperature (e.g., 94° C. for polystyrene) in solution (e.g., within a 20 ml vial). This process is simpler, and can yield more particles than previous methods such as chemically linking magnetic chains, depositing microspheres in a groove shaped template to form chains and then melting them together in the groove, or passing microspheres through a microfluidic device where they are briefly heated.

Example 13

Preparation of Brownian MOONs

A drop of a solution containing fluorescent polystyrene nanospheres 300 nm in diameter (Bangs labs) in a water or ethanol-water mixture was spread out on a glass slide using a pipette tip, and allowed to dry to deposit a monolayer of nanospheres. The slide was then placed in an aluminum vapor deposition system and coated with approximately 100 nm of aluminum thereby capping the particles. Particles were removed with a damp paintbrush and suspended in water after 30 seconds of sonication. A small drop of the solution was placed on a slide and viewed under a microscope to confirm the yield of Brownian MOONs.

Solutions of 1-2 µm and 2 µm Brownian MOONs were prepared by the same method, only substituting 1-2 um fluorescent superparamagnetic polysyrene microspheres (Polysciences) and 2 µm green fluorescent biotin coated microspheres (Polysciences) for the 300 nm nanospheres described above.

In some cases, the micro- and nano-spheres were rinsed in water, centrifuged, and resuspended deionized water to remove excess surfactant prior to aluminum capping.

Example 14

Separating the Blinking Brownian MOON Signal from Other Signals

A dilute solution of 1-2 µm fluorescent superparamagnetic Brownian MOONs prepared as described in Example 12 was loaded into a rectangular capillary (Friedrich & Dimmock, inc.) by dipping the end of the capillary in the solution. The solution was viewed with an Olympus IMT2 epifluorescence microscope. One Brownian MOON moved into view, and a time series of 260 spectra were taken. A new spectrum in the time series was taken approximately once every 200 ms. Principle components analysis was then performed on the time series of spectra in order to separate out the different spectral components present in the spectra and to see how each component varied in time.

Figure 30:
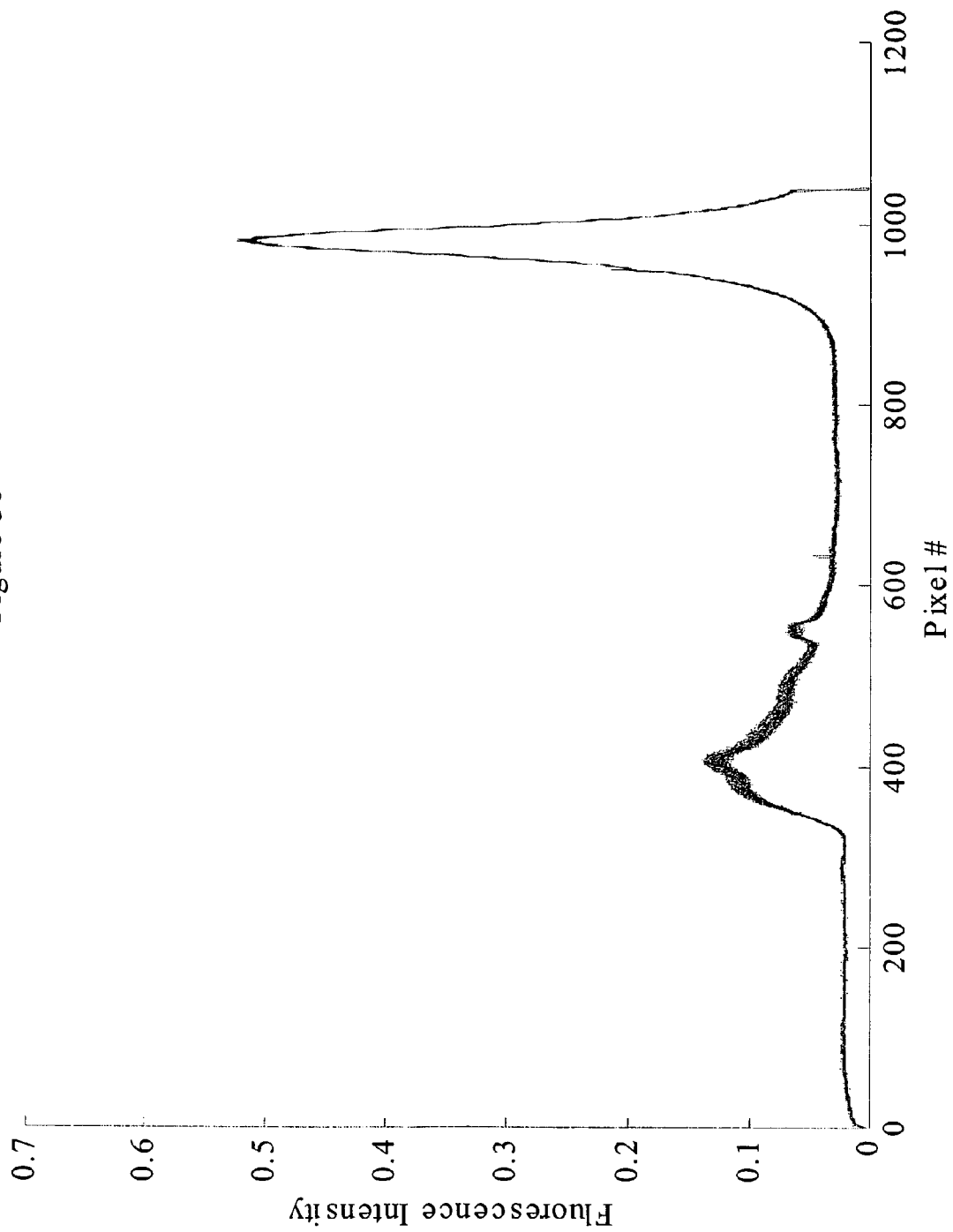
FIG. 30 shows a time series of fluorescence spectra consisting of a composite intensity at each wavelength from the following sources: intense mercury arc Lamp background, autofluorescence, room lights, fluorescent Brownian MOONs, one cosmic event or spike, and random electrical noise from the detectors readout amplifier.

FIG. 30 shows a time series of fluorescence spectra consisting of a composite intensity at each wavelength from the following sources: intense mercury arc Lamp background; autofluorescence, room lights, fluorescent Brownian MOONs, one cosmic event or spike, and random electrical noise from the detectors readout amplifier.

Figure 31:
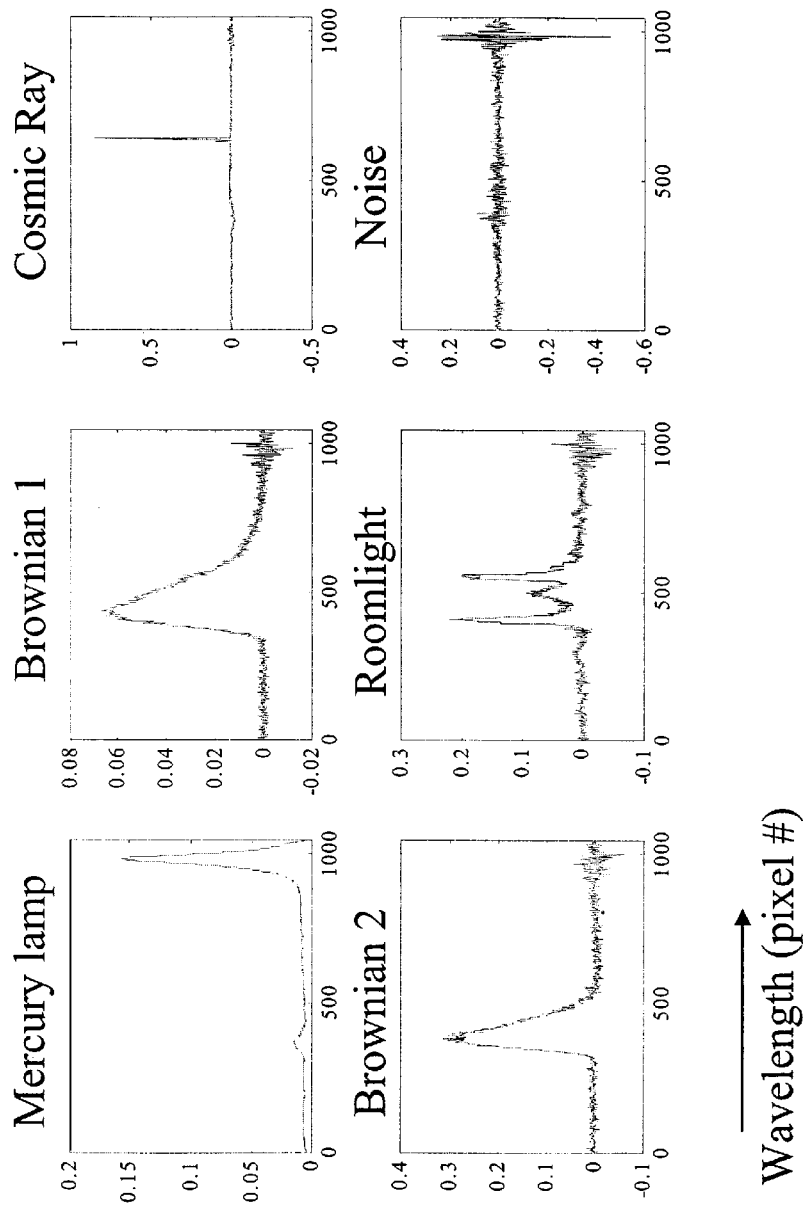
FIG. 31 illustrates that modulated particle fluorescence allows for separation of particle signal from the other sources as shown in the principal components representing the spectrum from each source: (A) Mercury lamp background and autofluorescence (B) Brownian MOON fluorescence (C) Cosmic spike (D) Brownian MOON fluorescence (E) Spectrum of room lights (F) the detector noise.

FIG. 31 illustrates that modulated particle fluorescence allows for separation of particle signal from the other sources as shown in the principal components representing the spectrum from each source: (A) Mercury lamp background and autofluorescence (B) Brownian MOON fluorescence (C) Cosmic spike (D) Brownian MOON fluorescence (E) Spectrum of room lights (F) the detector noise.

Figure 32:
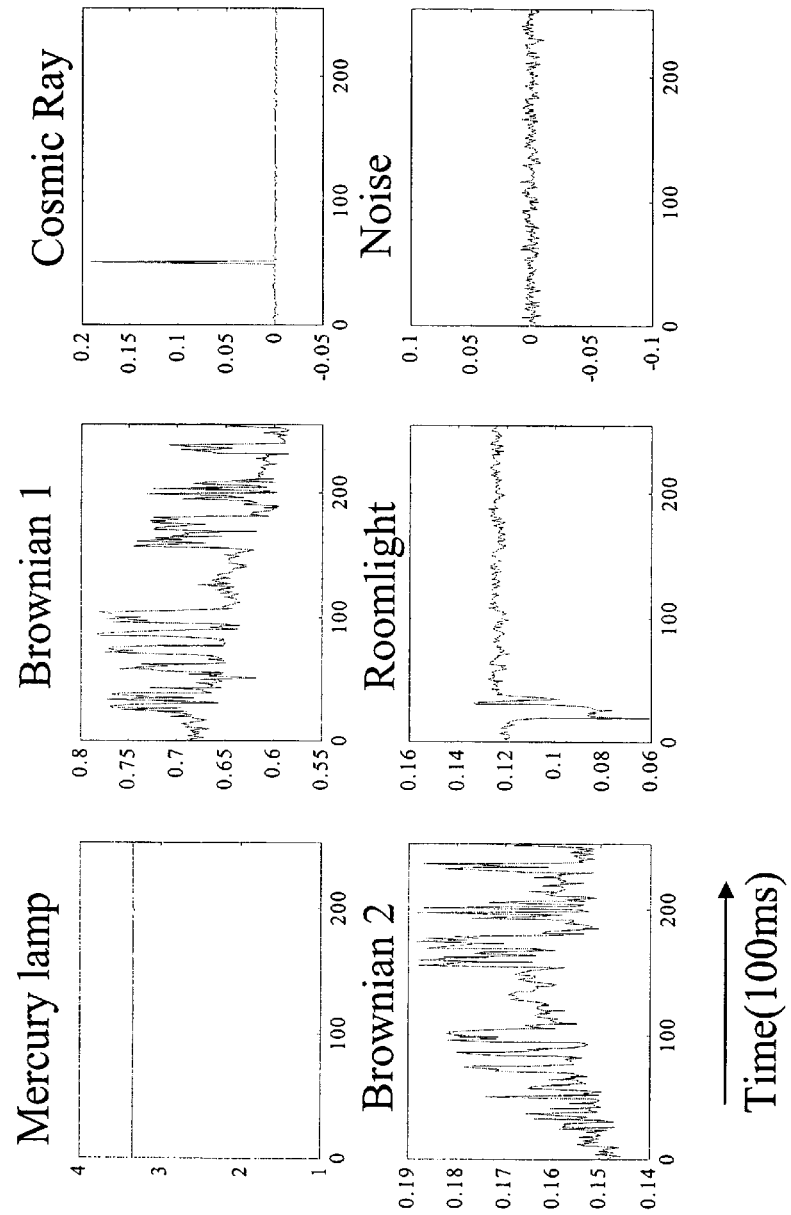
FIG. 32 shows the time signature for each of the principal components shown in FIG. 31.

FIG. 32 shows the time signature for each of the principle components. The meaningful fluorescent signal from the Brownian MOON (B) and (D) has a distinct time signature from (A) the constant mercury arc lamp background and autofluorescence (C) the cosmic spike at one instant in time (E) the decrease in roomlight entering through the door as the experimenter left the room and (F) the high frequency hum of detector noise. The two dyes in the Brownian MOON had slightly different spatial distributions on the bright side of the Brownian MOON and also bleach at different rates.

Example 15

Measuring Viscosity from Autocorrelation Times

A solution of 2 um fluorescent biotin coated fluorescent Brownian MOONs was prepared as described in Example 12. The solution was mixed with glycerol solution to provide 24% and 44% glycerol solutions that are 2 and 4 times more viscous than water. The solutions were put into a demountable 100 µm quartz sample chamber (Starna). It was clear by inspection (and video recording) that the rate of reorientation and blinking was slower for MOONs in higher viscosity solutions. A time-series of spectra were taken of single particles reorienting under Brownian motion. Principle components analysis was applied to the time-series in order to separate the Brownian MOON signal from other signals present in the spectra. An autocorrelation was performed on the times series of the Brownian MOON fluctuations in order to measure the rate of fluctuation. The autocorrelation function decayed exponentially, and half-life of the decay was used to compare the different MOONs. It was found that the decay rate increased with increasing viscosity.

Example 16

Putting MagMOONs into Macrophages

A solution of 4-5 µm MagMOONs was prepared as described in Example 3. An aliquot of the solution was added to a culture of macrophages and incubated for 24 hours. Most of the MagMOONs were engulfed into the macrophages during this time, and those that were not were washed away. Calcein dye was used to stain the cytoplasm of live cells for easy visualization under a confocal microscope. Many macrophages had one or two MagMOONs in them. One large macrophage had engulfed six MagMOONs. A permanent magnet was turned in order to rotate magnet particles within the macrophage. One MagMOON was seen to reorient slowly in a magnetic field for a few minutes.

Cells containing MagMOONs free in solution could be oriented using a magnetic field. Yeast was incubated with iron oxide nanoparticles (Sigma-Aldrich) for 24 hours. The yeast adsorbed some magnetic material in it. The yeast could be manipulated with magnetic fields.

Example 17

Reorientation of Brownian MOONs in a Macrophage

The MOONs were added to the macrophage buffer solution for 24 hours to be taken up by the macrophages. The buffer was periodically changed to remove any free MOONs that the macrophages had not engulfed. Under a fluorescence microscope, green fluorescence from the Brownian MOONs was clearly visible in most of the macrophages. Images of the Brownian MOONs in the macrophages were taken with a Nikon coolpix 995 digital camera periodically. Sequential images were used to monitor the orientation and position of the particles in time. Difference in intensity results from a difference in Brownian MOON orientation and can be visualized. Sequential images were used to monitor the orientation and position of the particles in time.

The Brownian MOONs reorient in time as shown by their blinking off and others turning on between images as well as intensity changes. In this case the reorientation rate occurred on the timescale of minutes. This slow reorientation rate of the 300 nm Brownian MOONs in macrophages suggests that there is very little fluid within the phagosomes and that the phagosomes are held rigidly in the cytoplasm. The reorientation allows the determination of active and viscous forces on the phagosomes and an assessment of change as a function of position, time, translational motion, and external stimuli. With a chemical sensing MagMOON, these physical processes can be correlated to chemical changes within the phagosomes, for instance measuring acidity changes within a phagosome using a pH sensitive MagMOON. These measurements have not been made before.

Example 18

Brownian MOONs Shot into C6 Glioma Cells

A solution of 300 nm Brownian MOONs was prepared as described in Example 12. Brownian MOONs were deposited onto a gene gun disk by applying Brownian MOON solution to the disk with a paintbrush and letting the water evaporate. The disk was placed into a gene gun assembly (Biorad). C6 glioma cells were put under slight vacuum below the gene gun for less than 1 minute. A 600 psi burst of pressure was used shoot the Brownian MOONs into C6 glioma (brain cancer) cells. The cells were then immersed in buffer and allowed to recover for 30 minutes. The cells were viewed under a fluorescence microscope. The images show Brownian MOONs within a glioma cell. The subtracted index shows intensity changes due to translational movement and reorientation of the Brownian MOONs within the cell.

Example 19

Production of Uniform Half-Shell MagMOONs with Vapor Deposited Magnetic Materials.

This example describes production of uniform half-shell MagMOONs using vapor deposition of cobalt and iron. MagMOONs were produced by coating a uniform half-shell of ferromagnetic cobalt onto nanospheres and microspheres using ultra high vacuum (UHV) vapor deposition. Uniformly sized polystyrene spheres 50 nm, 300 nm, 970 nm 2 µm, and 3.4 µm in diameter (purchased from Bangs Labs and Polysicences Inc.) were coated with cobalt. The cobalt was deposited at a rate of 1-4 Å/s, providing fine control of the layer thickness.

Figure 33:
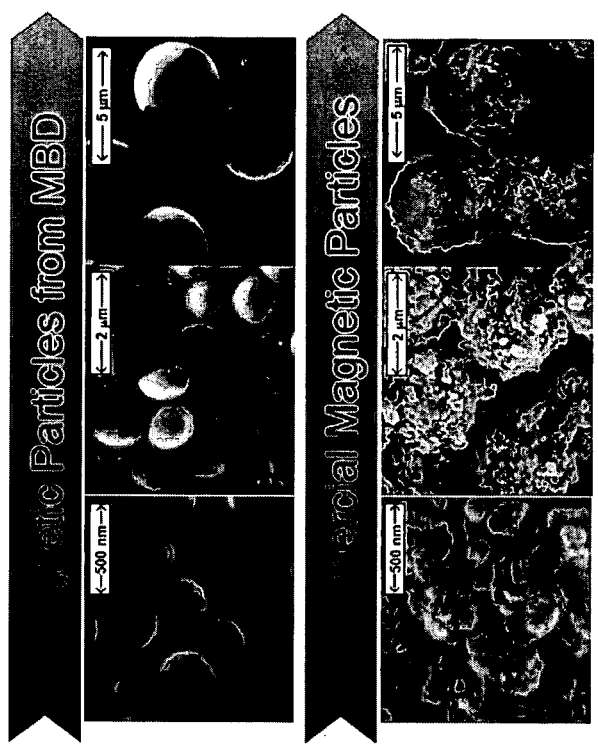
FIG. 33 shows scanning electron microscopy (SEM) images of various magnetic particles, where the arrow indicates increasing size. Top Row: Magnetic particles fabricated by coating polystyrene spheres that are 300 nm in diameter with a layer of 20 nm of cobalt; 1.0 µm in diameter spheres coated with 30 nm of cobalt; and 3.4 µm spheres coated with 20 nm of cobalt. Bottom Row: Commercially made magnetic particles that are 330 nm, 1.89 µm, and 4.4 µm in diameter (Spherotech, Inc.).

The use of top down deposition of magnetic materials solves the longstanding problem of non-uniformity in commercially made magnetic particles (usually produced using purely bottom up chemical synthesis). The control over material composition also increases the effective magnetic moment of the particles compared to iron oxide, and allows control over coercivity, and addition of protective layers of materials including metals and silica. After the spheres were coated, SEM images were taken, FIG. 33. The top row of FIG. 33 depicts magnetic half-shell particles fabricated using UHV vapor deposition, where the direction of the arrow indicates increasing size, from 300 nm to 3.4 µm. For comparison, the bottom row of FIG. 33 shows similarly sized commercially made magnetic particles. These commercially made particles appear to be rough, irregular in shape (>20% deviation from a perfect circle for 340 nm particles) and have a large variation in size, especially for smaller particles; by comparison, the cobalt coated particles are smooth, have close to spherical shape (<10% deviation from a perfect circle for 300 nm particles), and have a narrower size distribution.

Figure 34:
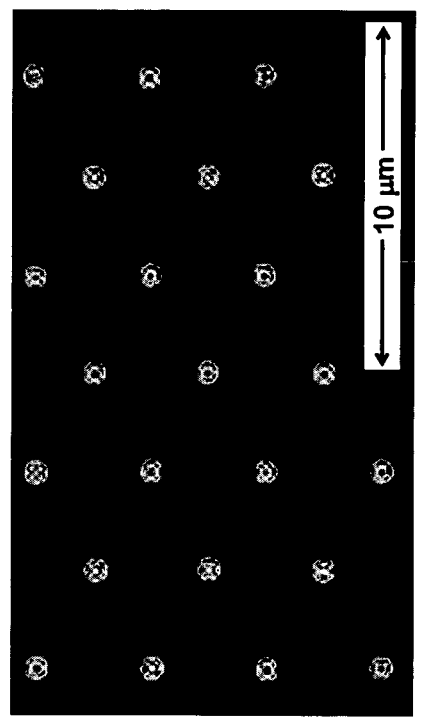
FIG. 34 shows a brightfield image of a monolayer of 3.4 µm polystyrene microspheres, coated with 30 nm of cobalt.

To investigate variations in coating uniformity from particle to particle, the 3.4 µm cobalt coated particles were imaged with bright field (transmission) microscopy. On a flat surface the 30 nm of cobalt attenuated light by 10.6%. The images, FIG. 34, revealed particles with almost identical transmission profiles and small variations in maximum transmission (6% standard deviation). Large deviations in the amount of magnetic material will affect magnetic responsiveness (Häfeli et al., European Cells and Materials 3, 34 (2002). When commercially available 4.4 µm magnetic microspheres were used for microrheology, measurements varied significantly from sphere to sphere.

Also evident from the SEM images are arch-like structures in the deposited metal of the 300 nm and the 3.4 µm cobalt-coated spheres, top row of FIG. 33. These arches are formed by two methods, either allowing the substrate temperature to exceed the glass transition temperature of polystyrene (≈95° C.), or by using an angled deposition so one particle shadows its neighbor from the cobalt atomic beam flux. If the substrate temperature was above the glass transition temperature of polystyrene, then the particles could fuse together, and when broken apart leave an arch-like structure on the surface of the sphere. The eye-shaped patterns inside the arches provides evidence for melting and sticking together for the 3.4 µm spheres, top right of FIG. 33. Alternatively, when coating occurs at a significant angle normal to the substrate, in our case ~40°, then the arches could form from shadowing effects, as observed on silica coated particles. The presence of these arches could affect the magnetic properties of the cobalt film.

Additionally, the lightning rod effect creates large electromagnetic field enhancements at the tips with applications for SERS (surface enhanced Raman spectroscopy) and for non-linear optical effects, similar to enhancements seen with prism shaped particles and nanocrescents.

To further characterize the magnetic half-shell particles fabricated by UHV vapor deposition, MOKE magnetometry in longitudinal geometry was performed on 50 nm spheres coated with a 20 nm of cobalt. The presence of these nanospheres enhanced the coercivity of the planar cobalt layer by more than a factor of three, compared to bulk values. The magnetic hysteresis curves for the 50 nm spheres with the magnetic field applied parallel to the substrate, have a square-like shape, indicating that the easy axis of magnetization is parallel with the substrate surface as well as with the nanosphere surface.

Figure 35:
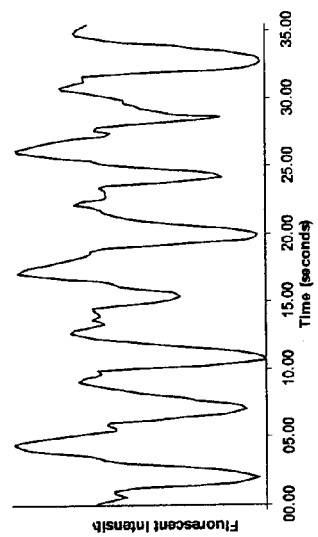
FIG. 35 shows characterization of uniform magnetic particles indicating time versus the fluorescence intensity from a 3.4 urn cobalt coated MagMOON rotated by a 0.25 Hz magnetic driving field.

In addition to forming magnetic half-shell particles on a plane, particles were removed from the glass substrate, suspended them into solution, and rotated with an external magnetic field. FIG. 35 shows the time series for a 3.4 µm fluorescent polystyrene microsphere with a cobalt layer of 20 nm, modulated in an external rotating magnetic field at a driving frequency of 0.25 Hz. Upon demodulation, by subtracting "On" minus "Off," the background can be removed, thus allowing for more sensitive fluorescence measurements. The same process can be utilized with almost any nanosphere or microsphere, thereby allowing nanosensors or microsensors to be modified into MagMOONs.

Silica nanospheres coated with a magnetic layer of iron covered with a protective layer of silver were produced. These were observed to rotate in rotating magnetic fields, and produce a modulated reflection signal.

Example 20

Rotation Rate of Different Sized Brownian MOONs

Figure 36:
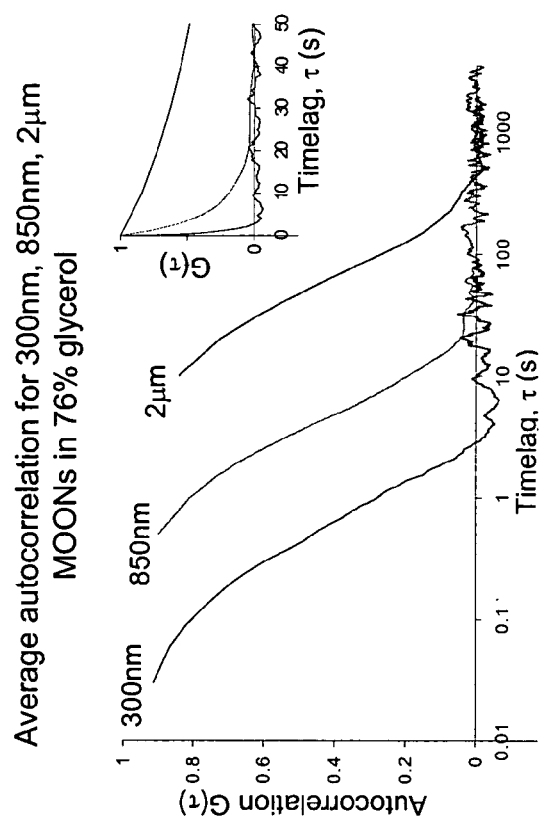
FIG. 36 shows the autocorrelation functions for 300 nm, 850 nm, and 2 micron Brownian MOONs with 50 nm Aluminum coating.

This example describes measuring the intensity autocorrelation function for various sizes of Brownian MOONs. The autocorrelation function of the angle or intensity from Brownian MOONs provides a measure of the angular diffusion rate. FIG. 36 shows the mean autocorrelation function for several replicates of 300 nm, 850 nm, and 2 μm Brownian MOONs in a 76% glycerol solution. The plot, presented on a semi-log scale, shows exponential decays with well separated time constants (time to decay to 1/e). These differences allow different sized particles to be distinguished based on rotation rate. In addition, they allow probing at different sizes.

Example 21

Detection of Particle Binding with Brownian MOONs

Figure 37:
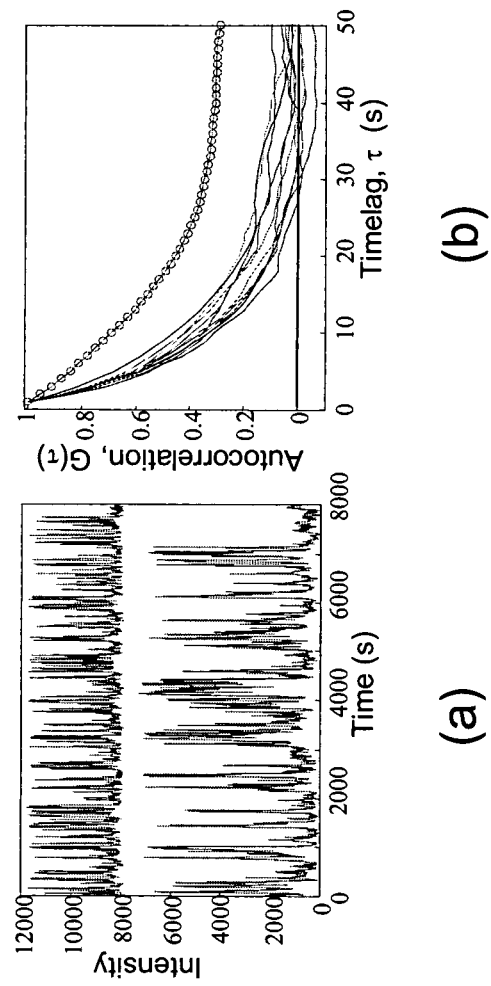
FIG. 37 shows the effect of aggregation on the intensity autocorrelation function of Brownian MOONs. (a) The Intensity time series for a single 2 µm polystyrene MOON (green) positively offset for comparison with a dimer (red). (b) Autocorrelation functions of a time series for ten single 2 µm Brownian MOONs

This example describes the use of Brownian MOONs to detect particle binding. At high particle concentrations, interactions between particles were observed. These aggregates were directly observed for 2 μm particles, and inferred from the intensity rates for all particle sizes. FIG. 37a shows the intensity fluctuations for a single 2 μm particle rotating in glycerol solution (top) and slower fluctuations for a single brighter particle (an aggregate) rotating in the same image series (bottom). FIG. 37b shows the autocorrelation function for the aggregate as well as for ten single spherical 2 μm Brownian MOONs. The decay time for the aggregate is approximately twice the average decay time for the single particles.

Figure 38:
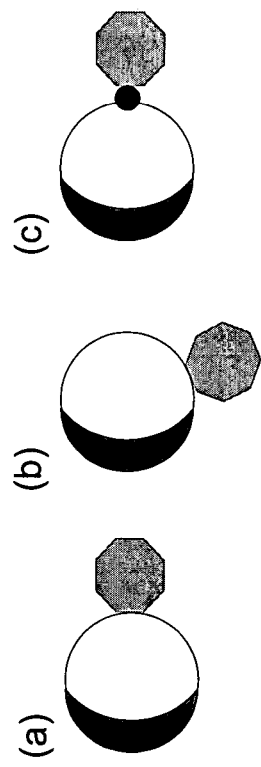
FIG. 38 shows a schematic of a particle binding to a MOON. (a) and (b) show the particle binding to different locations on the MOON relative to the capping, creating different amounts of drag around the azimuthal axis. (c) Using local breading to control location of binding target.

The ability to measure rotation rates enables the characterization of the drag on a MOON induced by binding, such as the binding of 50 nm viruses to 100 nm Brownian MOONs. Control over binding location relative to the capping material was achieved by chemically binding or physically pressing ("breading") smaller particles into large particles before metal capping (FIG. 38).

Example 22

MagMOONs Microviscometer.

This example describes MagMOONs used as microviscometers. A drop of glyercol (88% w/v) containing suspended MagMOONs was place on a microscope slide. The microscope slide was inverted so that the drop hung downwards, and MagMOONs in the solution were imaged with an inverted epifluorescence microscope. A function generator was used to precisely control the rate of rotation of a stepper motor connected to a cylindrical magnet that was magnetized through its diameter. In addition, the microscope slide was placed on a heated stage to control the temperature of the glycerol solution.

Figure 39:
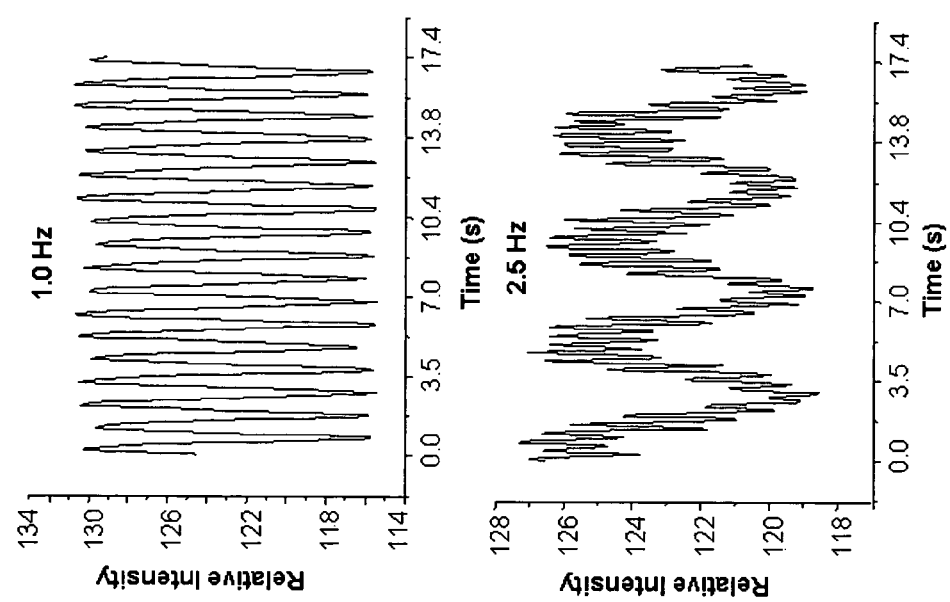
FIG. 39 shows the intensity time series from a single 4.4 µm fluorescent MagMOON in 88% glycerol.

The motor was rotated at a series of rotation rates, while the MagMOON fluorescence intensity was recorded with a CCD camera and analyzed with Metamoph Imaging software (Universal Imaging Corp.). It was found that there were two regimes for the behavior: at slow speeds, the MagMOONs rotated at the rate of the driving fields; above a maximum rotation rate, however, the MagMOONs underwent a rocking motion superimposed on a slow net rotation (FIG. 39). Near the maximum rotation rate, the net slow rotation is very sensitive to slight changes. This behavior matched well with the fit to the theoretical model for average rotation rate in a continuously rotated magnetic field:

$$\langle d\theta/dt \rangle = \begin{cases} \omega, & \omega < \omega_{max} \\ \omega - \sqrt{\omega^2 - \omega_{max}^2}, & \omega < \omega_{max} \end{cases} \quad \text{Equation 1}$$

$$\omega_{max} = MB/\eta\kappa V \quad \text{Equation 2}$$

Where $\langle d\theta/dt \rangle$ is the average rotation rate for the MagMOON, $\omega$ is the frequency of the driving field, $\omega_{max}$ is the maximum rotation rate, M is the magnitude of the MagMOON's magnetic moment (remnance magnetization after magnetizing), B is the magnitude of the external magnetic field, $\omega$ is the driving frequency of the rotating external magnetic field, $\theta$ is the angle between the external field and the MagMOON moment, $\eta$ is the medium's rotational viscosity, V is the volume of the MagMOON, and K is a shape factor (6 for a sphere). The maximum rotation rate was determined by increasing the driving field frequency until the MagMOONs were observed to get lapped by the magnet and rotate backwards.

Figure 40:
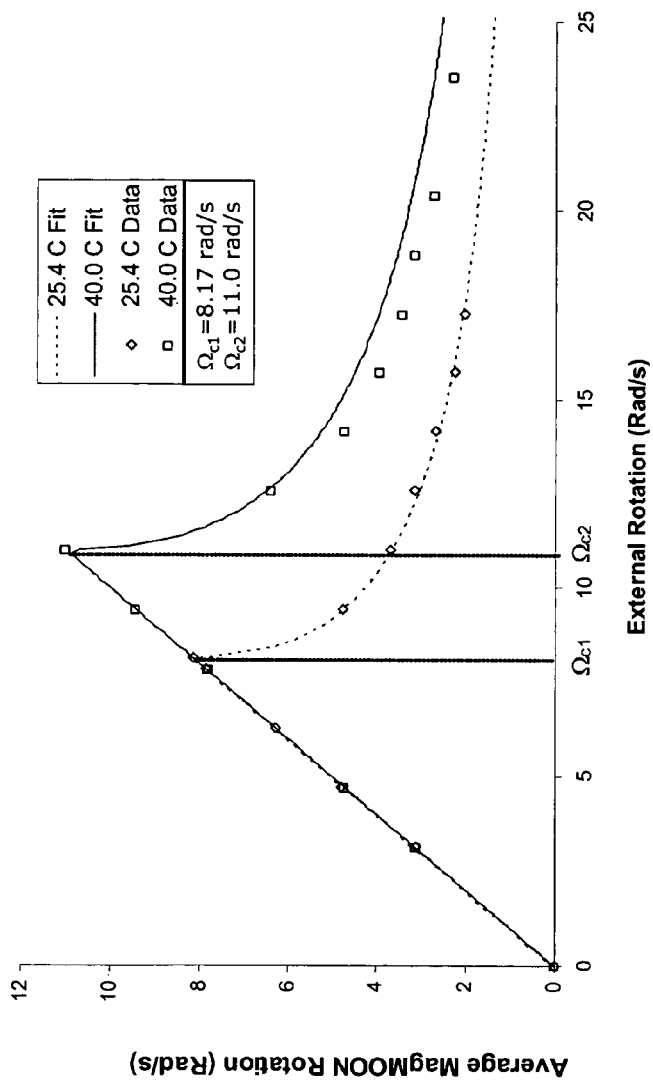
FIG. 40 shows the average rotation rate of a single MagMOON as a function of frequency for an 88% glycerol solution at 25.4° C. and 40° C.

To demonstrate that the maximum rotation rate of single MagMOONs responded to solution viscosity, the glycerol solution was heated from 25.4° C. to 40° C. The increase in viscosity and decrease in maximum rotation rate in the higher temperature glycerol is evident in FIG. 40.

Example 23

Measurement of Friction/Rolling Traction Using MagMOONs

This Example describes measurement of friction and rolling using MagMOONs. If the MagMOONs settle to a surface, they are observed to translate as they rotate around the center of pressure, rolling on the surface. For example, two ~4.5 um MagMOONs in a solution on a glass slide were rotated simultaneously with a magnetic field and observed to roll an average of 0.35 +/−0.3 particle diameters each revolution; compared to a no slip condition, where the particle would roll π diameters per revolution, this corresponds to a traction efficiency of (11+/−1)%. The rate of rolling depends on the particle size and shape, and surface interactions resulting in separation based on size and chemistry, if given sufficient distance. The rolling traction depended on position and time (varying from 4% to 36%). Observing friction and slip is a novel method for the study of surface interactions on the micro and nano-scale as a function of rotation rate, surface properties, particle surface properties (on both metal capped and uncoated sides), shape of particle, and pressure normal to the surface. In an inhomogeneous medium, the surface interactions can occur in three dimensions, and direction of rolling provides insight into the local structure of the medium around the particle.

Example 24

Observation of Vorticity with Brownian MOONs

This Example demonstrates that Brownian MOONs rotate due to vorticity in fluid flow.

A solution of 2 μm or 3.4 μm Brownian MOONs are observed to rotate and blink when the fluid flows due to evaporation in a 100 μm demountable glass cell (Starna). They are also observed to rotate in flow due to wetting of a roughened microscope slide. In the later case, the flow is irregular, and the rotation rate depends strongly on particle position. A similar method of measuring viscosity is to use microspheres encapsulating flat reflective crystals, and measure the rate of flashing from reflection off the rotating crystal (U.S. Pat. No. 4,385,830, herein incorporated by reference in its entirety). The use of MOONs allows a more continuous measurement of angle, and more uniform probes.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of detecting an analyte, the method comprising:
   a) providing
      i) a plurality of magnetic probes; and
      ii) a device configured for the detection of different fluxes of light from said magnetic probes as they rotate;
   b) contacting a sample with said magnetic probes under conditions such that analyte objects comprising non-adherent prokaryotic cells or non-adherent eukaryotic cells in the sample are able to bind to said magnetic probes;
   (c) applying a rotating magnetic field at a driving rotation rate to rotate the magnetic probes so that the non-adherent prokaryotic cells or non-adherent eukaryotic cells bound to the magnetic probes have a net rotation rate that is slower than the driving rotation rate, the magnetic probes and the bound non-adherent prokaryotic cells or the bound non-adherent eukaryotic cells are directionally free to rotate in response to the rotating magnetic field; and
   (d) while applying the rotating magnetic field, detecting said different fluxes of light with said device to generate a modulated probe signal over time, as non-adherent prokaryotic cells or non-adherent eukaryotic cells bind or swell on the magnetic probes.

2. The method of claim 1, wherein said magnetic probes further comprise a labeling particle, said labeling particle attached to said magnetic probes.

3. The method of claim 2, wherein said labeling particle is an indicator dye.

4. The method of claim 1, further comprising identifying said analyte object based on changes in said modulated probe signal.

5. The method of claim 1, wherein said sample is selected from the group consisting of a bodily fluid and a cellular homogenate.

6. The method of claim 1, wherein the magnetic probes comprise a plurality of probes each having a matrix coated with a metal half-shell.

7. The method of claim 1, further comprising detecting an increase in drag on the magnetic probe from the modulated probe signal.

8. The method of claim 1, wherein the modulated probe signal corresponds to changes in the rate of rotation of the non-adherent prokaryotic cells or non-adherent eukaryotic cells bound to the magnetic probes and represents changes in the hydrodynamic radius of the non-adherent prokaryotic cells or non-adherent eukaryotic cells bound to the magnetic probes.

9. A method of detecting analytes in a sample, the method comprising:
   contacting a sample with a plurality of magnetic probes to permit binding analyte objects within the sample to the magnetic probes, wherein the magnetic probes and bound analyte are directionally free to rotate in response to a rotating magnetic field;
   applying the rotating magnetic field at a driving rotation rate to rotate the magnetic probes so that the magnetic probes and the bound analytes have a net rotation rate that is slower than the driving rotation rate;
   optically monitoring the rotation rate of the magnetic probes and the bound analytes over time while applying the rotating magnetic field; and
   detecting an increase in drag of the magnetic probes based on a change in their rotation rate as the analyte objects bind or swell while applying the rotating magnetic field.

10. The method of claim 9, wherein contacting the sample comprises contacting the sample with the plurality of magnetic probes to permit binding of analyte objects comprising prokaryotic cells or eukaryotic cells to the magnetic probes.

11. The method of claim 9, wherein optically monitoring the rotation rate comprises measuring changes in light intensity.

12. The method of claim 9, wherein detecting an increase in drag comprises detecting a phase delay between the rotation rate of the magnetic probes compared to a driving rate of the applied rotating magnetic field.

13. A method of detecting analytes in a sample, the method comprising:
   contacting a sample with a plurality of magnetic probes to permit binding of analyte objects in the sample to the magnetic probes;
   applying a rotating magnetic field at a driving rate to rotate the analyte objects bound to the magnetic probes so that the analyte probes bound to the magnetic probes have a net rotation rate that is slower than the driving rotation rate, wherein the magnetic probes and the bound analyte objects are directionally free to rotate in response to the rotating magnetic field;
   optically monitoring the rotation rate of the analyte objects bound to the magnetic probes over time while applying the rotating magnetic field; and
   detecting different fluxes of light from said probes as they rotate while applying the rotating magnetic field.

14. The method of claim 13, wherein contacting the sample comprises contacting the sample with the plurality of magnetic probes to permit binding of an analyte comprising non-adherent prokaryotic cells or non-adherent eukaryotic cells to the magnetic probes.

15. The method of claim 13, wherein detecting different fluxes of light comprises detecting the different probe orientations as the probes rotate.

* * * * *